US007578855B2

(12) United States Patent
Fadli

(10) Patent No.: US 7,578,855 B2
(45) Date of Patent: *Aug. 25, 2009

(54) COMPOSITION FOR DYEING KERATIN FIBERS COMPRISING AT LEAST ONE CATIONIC 3-AMINO-PYRAZOLOPYRIDINE DERIVATIVE, AND METHODS OF USE THEREOF

(75) Inventor: Aziz Fadli, Chelles (FR)

(73) Assignee: L'Oréal S.A., Paris (FR)

(*) Notice: Subject to any disclaimer, the term of this patent is extended or adjusted under 35 U.S.C. 154(b) by 111 days.

This patent is subject to a terminal disclaimer.

(21) Appl. No.: 11/594,957

(22) Filed: Nov. 9, 2006

(65) Prior Publication Data

US 2007/0136959 A1    Jun. 21, 2007

Related U.S. Application Data

(60) Provisional application No. 60/737,461, filed on Nov. 17, 2005.

(30) Foreign Application Priority Data

Nov. 9, 2005    (FR) .................................. 05 53402

(51) Int. Cl.
  *A61Q 5/10*    (2006.01)
  *C07D 513/02*    (2006.01)

(52) U.S. Cl. .................. 8/405; 8/406; 8/407; 8/410; 8/411; 8/435; 8/568; 8/570; 8/571; 8/574; 8/669; 8/670; 546/121

(58) Field of Classification Search .............. 8/405, 8/406, 407, 410, 411, 435, 568, 570, 571, 8/574, 669, 670; 546/121
See application file for complete search history.

(56) References Cited

U.S. PATENT DOCUMENTS

| 2,841,584 | A | 7/1958 | Hunter et al. |
| 4,003,699 | A | 1/1977 | Rose et al. |
| 4,128,425 | A | 12/1978 | Greenwald |
| RE30,199 | E | 1/1980 | Rose et al. |
| 4,823,985 | A | 4/1989 | Grollier et al. |
| 5,061,289 | A | 10/1991 | Clausen et al. |
| 5,234,818 | A | 8/1993 | Zimmermann et al. |
| 5,380,340 | A | 1/1995 | Neunhoeffer et al. |
| 5,457,200 | A | 10/1995 | Zimmermann et al. |
| 5,534,267 | A | 7/1996 | Neunhoeffer et al. |
| 5,663,366 | A | 9/1997 | Neunhoeffer et al. |
| 5,766,576 | A | 6/1998 | Löwe et al. |
| 6,027,538 | A | 2/2000 | Vandenbossche et al. |
| 6,099,592 | A | 8/2000 | Vidal et al. |
| 6,099,593 | A | 8/2000 | Terranova et al. |
| 6,284,003 | B1 | 9/2001 | Rose et al. |
| 6,338,741 | B1 | 1/2002 | Vidal et al. |
| 6,645,258 | B2 | 11/2003 | Vidal et al. |
| 6,730,789 | B1 * | 5/2004 | Birault et al. ............ 546/121 |
| 7,091,215 | B2 | 8/2006 | Hibi et al. |
| 7,285,666 | B2 | 10/2007 | Hibi et al. |
| 2002/0032934 | A1 | 3/2002 | Kravtchenko et al. |
| 2006/0277691 | A1 | 12/2006 | Saunier |
| 2006/0277693 | A1 | 12/2006 | Saunier |
| 2007/0136959 | A1 | 6/2007 | Fadli |
| 2007/0143935 | A1 | 6/2007 | Fadli et al. |

FOREIGN PATENT DOCUMENTS

| DE | 23 59 399 | 6/1975 |
| DE | 38 43 892 | 6/1990 |
| DE | 41 33 957 | 4/1993 |
| DE | 195 43 988 | 5/1997 |
| EP | 0 433 854 | 6/1991 |
| EP | 0 770 375 | 5/1997 |
| EP | 1 155 680 | 11/2001 |
| EP | 1 233 743 | 8/2002 |
| EP | 1 389 618 | 2/2004 |
| EP | 1 586 302 | 10/2005 |
| EP | 1 733 714 | 12/2006 |
| EP | 1 702 903 | 6/2007 |
| EP | 1 792 606 | 6/2007 |
| FR | A 2 733 749 | 5/1995 |
| FR | A 2 750 048 B1 | 8/1998 |
| FR | 2 767 475 | 2/1999 |
| FR | 2 801 308 | 11/1999 |
| FR | 2 586 913 | 3/2001 |
| FR | 2 822 689 | 10/2002 |
| FR | 2 822 690 | 10/2002 |

(Continued)

OTHER PUBLICATIONS

STIC Search Report dated Apr. 9, 2008.*
Boros, E. et al. 2001. "A Convenient Synthesis of Pyrazolidine and 3-Amino-6,7-dihydro-1H,5H-pyrazolo[1,2-α]pyrazol-1-one". *J. Heterocyclic Chem.* 38: 613-616.
Cohen, S. and Zand, R. 1962. "Bicyclic, Cyclic and Acyclic Azo Compounds, 2,3-Diazabicyclo[2,2,2]-2-octene, 3,6-Dimethyl-$\Delta^1$-tetrahydropyridazine and Aziosopropane". *J. Am. Chem. Soc.* 84: 586-591.
Heyman, M. and Snyder, J. 1973. "An Efficient Synthesis of Bicyclic Hydrazines and Azo Alkanes". *Tetrahedron Letters* 14(30): 2859-2862.
Kharasch, N. and Bruice, T. 1951. "Derivatives of Sulfenic Acids V. 1-Fluorenone Sulfur Compounds". *J. Am. Chem. Soc.* 73: 3240-3244.

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to a composition for the dyeing of keratin fibers, such as the hair, comprising at least one oxidation base chosen from cationic 3-amino pyrazolo-[1,5-a]-pyridine derivatives and addition salts thereof, and a method employing this composition. The present disclosure also relates to cationic 3-amino pyrazolo-[1,5-a]-pyridine derivatives and the addition salts thereof.

22 Claims, No Drawings

FOREIGN PATENT DOCUMENTS

| | | |
|---|---|---|
| FR | 2 822 691 | 10/2002 |
| FR | 2 822 692 | 10/2002 |
| FR | 2 886 137 | 12/2006 |
| FR | 2 886 139 | 12/2006 |
| GB | 1 026 978 | 4/1966 |
| GB | 1 153 196 | 5/1969 |
| JP | 2-19576 | 1/1990 |
| JP | 05-163124 | 6/1993 |
| JP | 2526099 | 8/1996 |
| WO | WO 94/08969 | 4/1994 |
| WO | WO 94/08970 | 4/1994 |
| WO | WO 96/15765 | 5/1996 |
| WO | WO 01/35917 | 5/2001 |
| WO | WO 02/076416 | 10/2002 |
| WO | WO 02/076417 | 10/2002 |
| WO | WO 02/76418 | 10/2002 |

OTHER PUBLICATIONS

Lingens, F. and Schneider-Bernlöhr, H. 1965. "Über die Umsetzung Natülich Vorkommender Pyrimidinbasen mit Hydrazin und Methylsubstituierten Hydrazinen". *Justus Liebigs Ann. Chem.* 686: 134-145.

Magnien, E. and Baltzly, R. 1958. "A Re-examination of Limitations of the Hofmann Reaction". *J. Org. Chem.* 23: 2029-2032.

Stenzl, H. et al. 1950. "Zur Kenntnis der 3-Amino-pyrazolone-(5)". *Helvetica Chimica Acta* 33(5): 1183-1194.

Fujito, H. et al. 1977. "Reaction of Pyrisnium and Isoquinolinium N-imines with Ketenethioacetals". *Heterocycles* 6(4): 379-382.

March, J. *Advanced Organic Chemistry*, 3rd ed. Wiley-Interscience, New York, USA, 1985) pp. 1048-1051, 1093-1120.

Hudlicky, M. *Reductions in Organic Chemistry*, (Ellis Horwood Limited, Chichester, England, 1983) pp. 1-13, 22-31.

French Search Report for FR 05 53402 (French priority application for the present application) dated Aug. 29, 2006.

French Search Report for FR 05 53403 (French priority application for co-pending U.S. Appl. No. 11/594,967) dated Jul. 24, 2006.

Office Action for U.S. Appl. No. 11/594,967 (co-pending application), dated Jun. 30, 2008.

Co-pending U.S. Appl. No. 11/594,967, filed Nov. 9, 2006.

Co-pending U.S. Appl. No. 12/149,871, filed May 9, 2008.

Co-pending U.S. Appl. No. 12/149,872, filed May 9, 2008.

English language Abstract of EP 1 586 302, dated Oct. 19, 2005.

English language Abstract of WO 02/076418, dated Oct. 3, 2002.

English language Derwent Abstract of JP 2-19576, dated Jan. 23, 1990.

English language Derwent Abstract of JP 2526099, dated Aug. 21, 1996.

French Search Report for FR 07/54947, dated Dec. 17, 2007, Examiner B. Miller (French priority application for U.S. Appl. No. 12/149,872).

French Search Report for FR 07/54948, dated Dec. 13, 2007, Examiner M. Pregetter (French priority application for U.S. Appl. No. 12/149,871).

Notice of Allowance mailed Jan. 21, 2009, in co-pending U.S. Appl. No. 12/149,872, Examiner E. Elhilo.

Notice of Allowance mailed Oct. 7, 2008, in co-pending U.S. Appl. No. 12/149,872, Examiner E. Elhilo.

Office Action mailed Feb. 5, 2009, in co-pending U.S. Appl. No. 11/594,967, Examiner E. Elhilo.

Office Action mailed Feb. 6, 2009, in co-pending U.S. Appl. No. 12/149,871, Examiner E. Elhilo.

STIC Search Report dated Apr. 9, 2008, for U.S. Appl. No. 11/594,967.

STIC Search Report dated Sep. 9, 2008, for U.S. Appl. No. 12/149,872.

* cited by examiner

COMPOSITION FOR DYEING KERATIN FIBERS COMPRISING AT LEAST ONE CATIONIC 3-AMINO-PYRAZOLOPYRIDINE DERIVATIVE, AND METHODS OF USE THEREOF

This application claims benefit of U.S. Provisional Application No. 60/737,461, filed Nov. 17, 2005, the content of which is incorporated herein by reference. This application also claims benefit of priority under 35 U.S.C. §119 to French Patent Application No. FR 05 53402, filed Nov. 9, 2005, the content of which is also incorporated herein by reference.

The present disclosure relates to a composition for the dyeing of keratin fibers, for example human keratin fibers such as the hair, comprising at least one cationic 3-amino-pyrazolo-[1,5-a]-pyridine derivative or the addition salts thereof and a method employing this derivative. It also relates to cationic 3-amino-pyrazolo-[1,5-a]-pyridine derivatives or the addition salts thereof.

The dyeing of keratin fibers, for example human keratin fibers such as the hair, with dyeing compositions comprising oxidation dye precursors, such as ortho- or para-phenylenediamines, ortho- or para-aminophenols, and heterocyclic compounds generally called oxidation bases, is known. Oxidation dye precursors, or oxidation bases, are compounds that are colorless or slightly colored, which, when combined with oxidizing products, can give rise to colored or coloring compounds by a process of oxidative condensation.

It is also known that the shades obtained with these oxidation bases can be varied by combining them with couplers or dyeing modifiers, the latter being potentially chosen from the meta-phenylenediamines, the meta-aminophenols, the meta-hydroxyphenols and certain heterocyclic compounds such as, for example, derivatives of pyrazolo[1,5-b]-1,2,4-triazoles, derivatives of pyrazolo[3,2-c]-1,2,4-triazoles, derivatives of pyrazolo[1,5-a]pyrimidines, derivatives of pyridine, derivatives of pyrazol-5-one, derivatives of indoline and derivatives of indole.

The variety of molecules employed in the oxidation bases and couplers means that a rich palette of colors can be obtained.

The so-called "permanent" dyeing obtained with these oxidation dyes should be able to meet a certain number of requirements. For example, these dyes should not pose any toxicological problems, should make it possible to obtain shades of the desired intensity, and should provide good resistance to external factors such as light, weather, washing, permanent waving, sweating and rubbing.

In addition, these oxidation dyes should also provide coverage of white hair, and they should have the least possible selectivity (i.e. the slightest possible differences in coloration all the way along one and the same keratin fiber, which may in fact have different sensitivity (i.e. extent of damage) between its tip and its root). These dyes should also display good chemical stability in the formulations, and should have a good toxicological profile.

The use of oxidation bases such as the derivatives of para-phenylenediamine and para-aminophenol can make it possible to obtain quite a wide range of colors at basic pH—although without achieving shades with good chromaticity—while endowing the hair with excellent properties of color intensity, variety of shades, uniformity of color and resistance to external factors.

However, the use of these bases at neutral pH is can be ineffective for achieving a range of varied shades, such as warm shades.

European Patent Application No. EP 1 233 743 discloses dye compositions containing 3-amino-pyrazolo-[1,5-a]-pyridines as the oxidation base. Among the 3-amino-pyrazolopyridines cited in that document, particular cationic compounds are cited that are different from those described in the present disclosure. The dye compositions described in EP 1 233 743 do not make it possible to achieve good properties of chromaticity, and/or resistance to external factors such as washing and light. Moreover, the range of shades obtainable by the compositions described in EP 1 233 743 is limited.

Accordingly, one non-limiting aspect of the present disclosure is to supply novel oxidation bases for the dyeing of keratin fibers which do not have the drawbacks of the known oxidation bases. Further, one non-limiting aspect of the present disclosure is to supply novel oxidation bases which make it possible to dye keratin fibers in a variety of shades that are powerful, chromatic, aesthetic, of low selectivity, and with good resistance to the various aggressive factors to which the keratin fibers may be subjected, such as shampoos, light, sweat and permanent shaping.

In this respect, the present disclosure relates to a composition for dyeing keratin fibers comprising, in a medium that is suitable for dyeing, as oxidation dyeing base, at least one 3-amino-pyrazolo-[1,5-a]-pyridine derivative of the formula (I), as well as its salts and solvates:

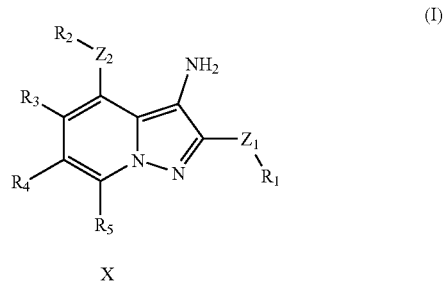

(I)

in which
  $Z_1$ and $Z_2$, which may be the same or different, are independently chosen from
    a single covalent bond,
    a divalent radical chosen from
      an oxygen atom;
      a radical —$NR_6(R_7)_p$—, with p=0 or 1, wherein:
        when p is equal to 0, $R_6$ is chosen from a hydrogen atom and $C_1$-$C_6$ alkyl radicals, or $R_6$ together with at least one of $R_1$ and $R_2$ form, together with the nitrogen atom to which they are attached, a substituted or unsubstituted, saturated or unsaturated, aromatic or non-aromatic heterocycle comprising 5 to 8 ring members, wherein said heterocycle may contain at least one heteroatom chosen from N, O, S, $SO_2$, and —CO—, and may be cationic and/or substituted with a cationic or non-cationic radical;
        When p is equal to 1, —$NR_6R_7$— is a cationic radical in which $R_6$ and $R_7$, may be the same or different, and are independently chosen from alkyl radicals; and
      when $R_1$ is a methyl radical, $Z_1$ may also be chosen from a divalent radical —S—, —SO— and —$SO_2$—;
with the proviso that at least one of $Z_1$ and $Z_2$ is not a single covalent bond;

$R_1$ and $R_2$, which may be the same or different, are indepently chosen from:
- a hydrogen atom;
- a $C_1$-$C_{10}$ alkyl radical, optionally substituted and optionally interrupted by a heteroatom or a group chosen from O, N, Si, S, SO and $SO_2$;
- a $C_1$-$C_{10}$ alkyl radical substituted and/or interrupted by a cationic radical;
- a halogen atom;
- an $SO_3H$ radical;
- a ring with 5 to 8 ring members, wherein said ring may be substituted or unsubstituted, saturated, unsaturated or aromatic, and may contain at least one heteroatom or group chosen from N, O, S, $SO_2$, —CO—, and said ring may be cationic and/or substituted with a cationic radical; and when at least one of $Z_1$ or $Z_2$ is a covalent bond, then $R_1$ or $R_2$ respectively may be also be a radical chosen from:
- optionally substituted $C_1$-$C_6$ alkylcarbonyls; and
- —O—CO—R, —CO—O—R, NR—CO—R' and —CO—NRR' in which R and R' may be the same or different, and are independently chosen from a hydrogen atom and optionally substituted $C_1$-$C_6$ alkyl radicals;

$R_3$, $R_4$ and $R_5$, which may be the same or different, are independently chosen from:
- a hydrogen atom;
- a hydroxyl radical;
- a $C_1$-$C_6$ alkoxy radical;
- a $C_1$-$C_6$ alkylthio radical;
- an amino radical;
- a monoalkylamino radical;
- a $C_1$-$C_6$ dialkylamino radical, in which the alkyl radicals can form, together with the nitrogen atom to which they are attached, a heterocycle with 5 to 8 ring members, wherein said heterocylce may be saturated or unsaturated, aromatic or non-aromatic, and may contain at least one heteroatom or groups chosen from N, O, S, $SO_2$, CO, and said heterocycle may be cationic and/or substituted with a cationic radical;
- an optionally substituted $C_1$-$C_6$ alkylcarbonyl radical;
- a radical chosen from —O—CO—R, —CO—O—R, NR—CO—R' and —CO—NRR' radicals, in which R and R' may be the same or different, and are independently chosen from a hydrogen atom and optionally substituted $C_1$-$C_6$ alkyl radicals;
- a halogen atom;
- a radical —$NHSO_3H$;
- an optionally substituted $C_1$-$C_4$ alkyl radical;
- an optionally substituted, saturated, unsaturated or aromatic carbon ring; and
- any two of $R_3$, $R_4$ and $R_5$ can form a saturated or unsaturated ring;

X is chosen from at least one anion that can ensure electronegativity of the derivative of formula (I), with the proviso that at least one of $Z_1$, $R_1$, $Z_2$ and $R_2$ represents a cationic radical.

The compositions of the present disclosure make it possible to obtain color-fast dyeing of keratin fibers, wherein said dyeing is resistant to light and to washing.

Another non-limiting aspect of the present disclosure is a method for dyeing keratin fibers employing the compositions of the present disclosure, as well as the use of these compositions for the dyeing of keratin fibers.

In a non-limiting embodiment, the present disclosure relates to novel pyrazolopyridine derivatives as well as the corresponding nitro or nitroso derivatives.

As used in the present disclosure, the term, "alkyl radical" means linear or branched alkyl radicals, which may be substituted or unsubstituted with any conventional substituent in the field of dyeing and which does not change the properties of the compounds of formula (I) as oxidation base.

The following substituents may be mentioned as non-limiting examples of substituents of these alkyl radicals: halo; hydroxy; alkoxy; amino; thio, alkylthio, $C_1$-$C_6$ alkylamino; $C_1$-$C_6$ dialkylamino in which the alkyl radicals can form, together with the nitrogen atom to which they are attached, a heterocycle with 5 to 8 ring members, saturated, unsaturated, aromatic or non-aromatic, cationic or non-cationic, and which may contain at least one heteroatom or group selected from N, O, S, $SO_2$, CO, and the heterocycle may be substituted; alkyl($C_1$-$C_6$)carbonyl; —O—CO—R; —CO—O—R; NR—CO—R' or —CO—NRR' in which R and R' are as defined previously; and a quaternary ammonium radical as defined previously.

This applies to the alkyl radicals present in any one of the radicals defined in formula (I), for example, the alkoxy (alkyl-O—) or alkylthio radicals.

As examples of substituents of the rings or heterocycles, non-limiting mention is made of alkyl radicals, substituted alkyl radicals, hydroxy, alkoxy, amino, alkylamino, and dialkylamino radicals.

As used herein, the term "cationic radical," means any linear or branched radical bearing a quaternary ammonium, this quaternary ammonium being of the type —$N^+R_{17}R_{18}R_{19}$, $R_{17}$, $R_{18}$, $R_{19}$, in which $R_{17}$-$R_{19}$ may be the same or different, and are chosen from $C_1$-$C_6$ alkyl radicals which may be substituted with a hydroxy.

As used herein, a cationic ring or heterocycle refers to a ring containing a quaternary ammonium.

As examples of radicals of the type —$N^+R_{17}R_{18}R_{19}$ which may be utilized in the present disclosure, non-limiting mention is made of trimethylammonium, triethylammonium, dimethyl-ethyl ammonium, diethyl-methylammonium, diisopropylmethylammonium, diethyl-propyl ammonium, hydroxyethyl diethyl ammonium, di-beta-hydroxyethylmethylammonium and tri-beta-hydroxyethylammonium radicals.

As non-limiting examples of cationic heterocycles that may be utilized in the present disclosure, mention is made of the imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, triazoliums and benzoxazoliums.

The compounds of formula (I) may optionally be salified by strong mineral acids, including, for example, HCl, HBr, HI, $H_2SO_4$ and $H_3PO_4$, or by organic acids such as, for example, acetic, lactic, tartaric, citric or succinic, benzenesulphonic, para-toluenesulphonic, formic and methanesulphonic acid.

The compounds of formula (I) may also be in the form of solvates, for example a hydrate or a solvate of a linear or branched alcohol such as ethanol or isopropanol. Of course, other solvents may also be utilized.

As used herein, the term "derivative" of formula (I) means all mesomeric or isomeric forms.

As non-limiting examples of derivatives of formula (I), mention is made of the following compounds, in which $X^-$ is as defined previously:

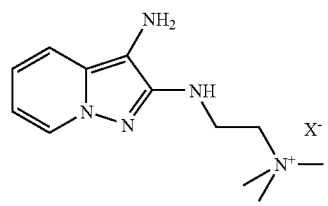

[2-(3-Amino-pyrazolo[1,5-a]pyridin-2-ylamino)-ethyl]-trimethyl-ammonium

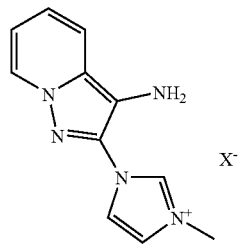

3-(3-Amino-pyrazolo[1,5-a]pyridin-2-yl)-1-methyl-3H-imidazol-1-ium

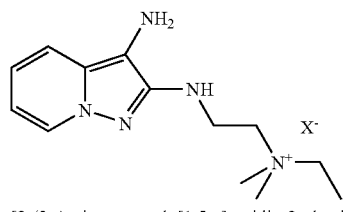

[2-(3-Amino-pyrazolo[1,5-a]pyridin-2-ylamino)-ethyl]-ethyl-dimethyl-ammonium

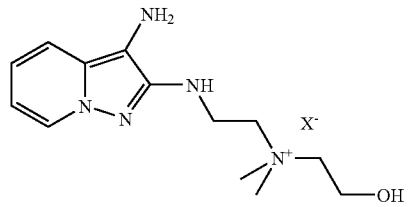

[2-(3-Amino-pyrazolo[1,5-a]pyridin-2-ylamino)-ethyl]-(2-hydroxy-ethyl)-dimethyl-ammonium

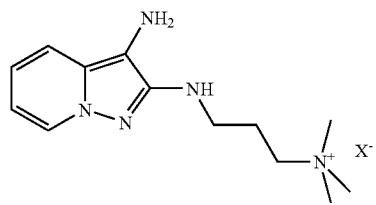

[3-(3-Amino-pyrazolo[1,5-a]pyridin-2-ylamino)-propyl]-trimethyl-ammonium

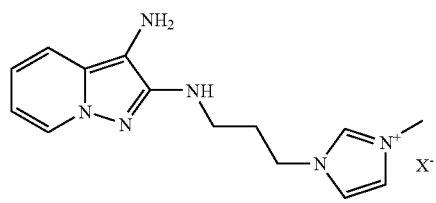

3-[3-(3-Amino-pyrazolo[1,5-a]pyridin-2-ylamino)-propyl]-1-methyl-3H-imidazol-1-ium

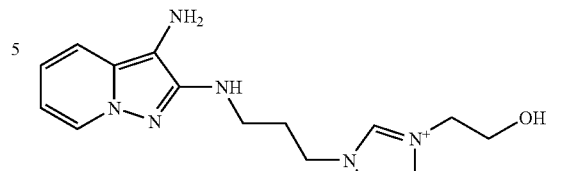

3-[3-(3-Amino-pyrazolo[1,5-a]pyridin-2-ylamino)-propyl]-1-(2-hydroxy-ethyl)-3H-imidazol-1-ium

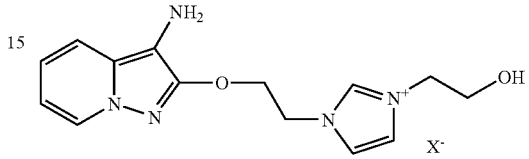

3-[2-(3-Amino-pyrazolo[1,5-a]pyridin-2-yloxy)-ethyl]-1-(2-hydroxy-ethyl)-3H-imidazol-1-ium

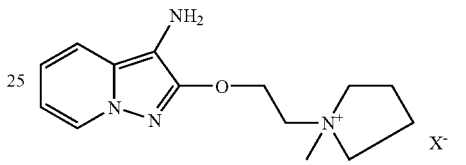

1-{2-[(3-aminopyrazolo[1,5-a]pyridin-2-yl)oxy]ethyl}-1-methylpyrrolidinium

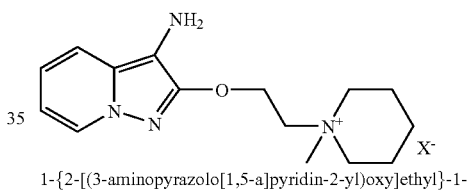

1-{2-[(3-aminopyrazolo[1,5-a]pyridin-2-yl)oxy]ethyl}-1-methylpiperidinium

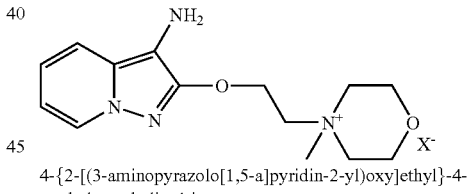

4-{2-[(3-aminopyrazolo[1,5-a]pyridin-2-yl)oxy]ethyl}-4-methylmorpholin-4-ium

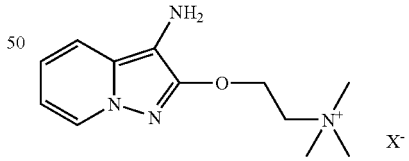

2-[(3-aminopyrazolo[1,5-a]pyridin-2-yl)oxy]-N,N,N-trimethylethanaminium

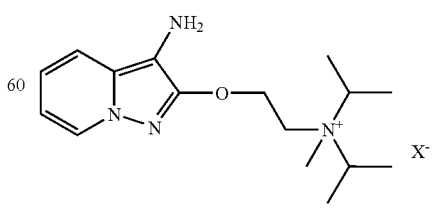

N-{2-[(3-aminopyrazolo[1,5-a]pyridin-2-yl)oxy]ehtyl}-N-isopropyl-N-methylpropan-2-aminium

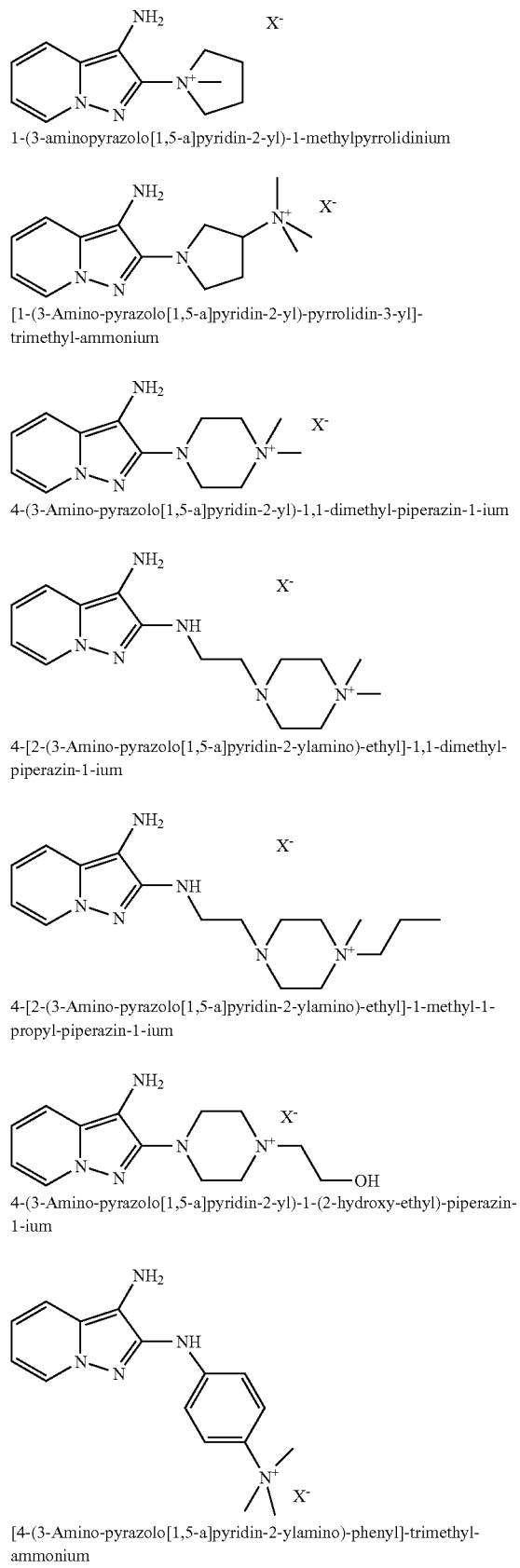
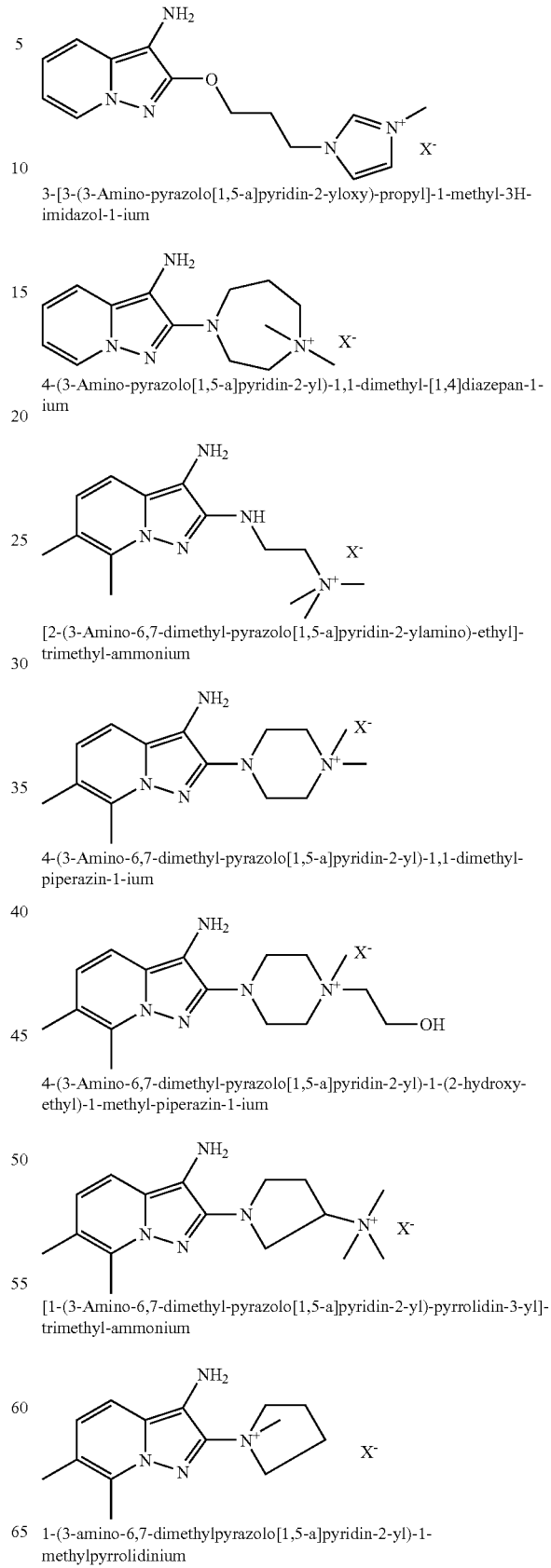

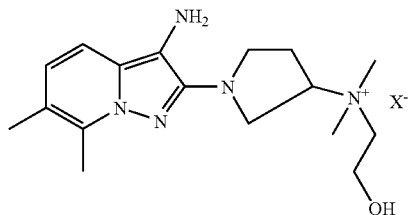

[1-(3-Amino-6,7-dimethyl-pyrazolo[1,5-a]pyridin-2-yl)-pyrrolidin-3-yl]-(2-hydroxy-ethyl)-dimethyl-ammonium

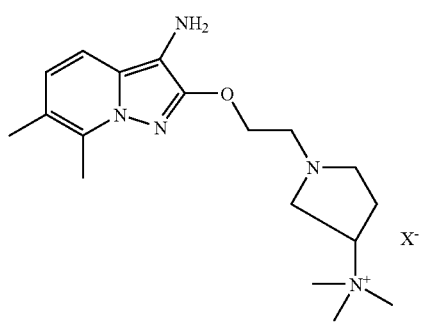

{1-[2-(3-Amino-6,7-dimethyl-pyrazolo[1,5-a]pyridin-2-yloxy)-ethyl]-pyrrolidin-3-yl}-trimethyl-ammonium

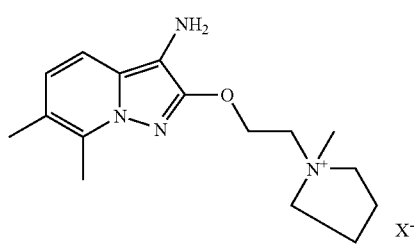

1-{2-[(3-amino-6,7-dimethylpyrazolo[1,5-a]pyridin-2-yl)oxy]ethyl}-1-methylpyrrolidinium

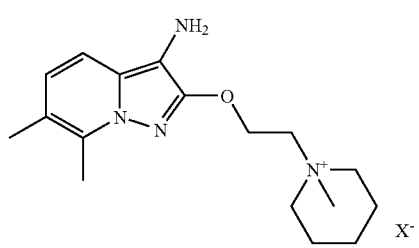

1-{2-[(3-amino-6,7-dimethylpyrazolo[1,5-a]pyridin-2-yl)oxy]ethyl}-1-methylpiperidinium

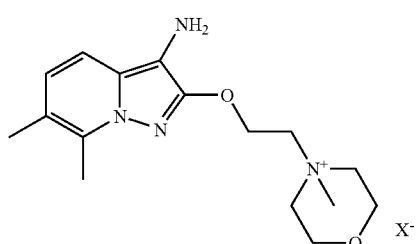

4-{2-[(3-amino-6,7-dimethylpyrazolo[1,5-a]pyridin-2-yl)oxy]ethyl}-4-methylmorpholin-4-ium

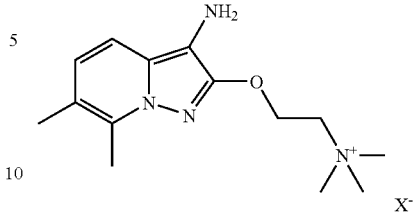

2-[(3-amino-6,7-dimethylpyrazolo[1,5-a]pyridin-2-yl)oxy]-N,N,N-trimethylethanaminium

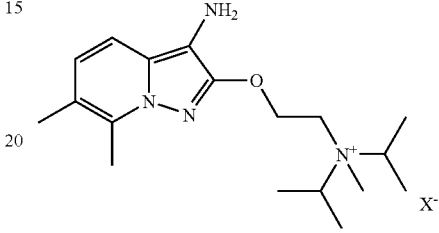

N-{2-[(3-amino-6,7-dimethylpyrazolo[1,5-a]pyridin-2-yl)oxy]ethyl}-N-isopropyl-N-methylpropan-2-aminium

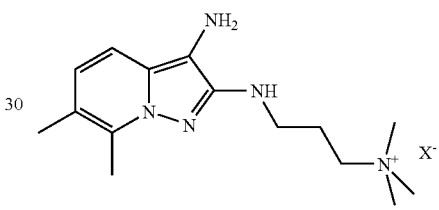

[3-(3-Amino-6,7-dimethyl-pyrazolo[1,5-a]pyridin-2-ylamino)-propyl]-trimethyl-ammonium

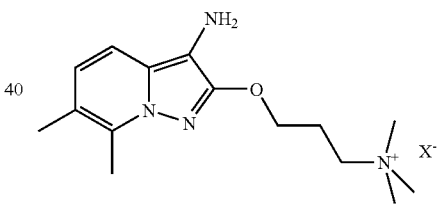

[3-(3-Amino-6,7-dimethyl-pyrazolo[1,5-a]pyridin-2-yloxy)-propyl]-trimethyl-ammonium

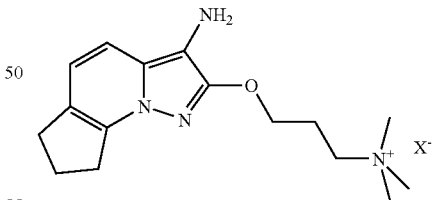

2-[(3-amino-7,8-dihydro-6H-cyclopenta[e]pyrazolo[1,5-a]pyridin-2-yl)oxy]-N,N,N-trimethylethanaminium

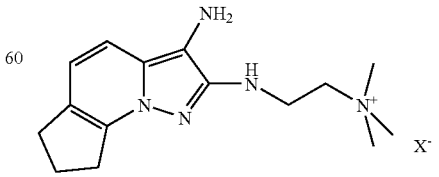

2-[(3-amino-7,8-dihydro-6H-cyclopenta[e]pyrazolo[1,5-a]pyridin-2-yl)amino]-N,N,N-trimethylethanaminium -continued

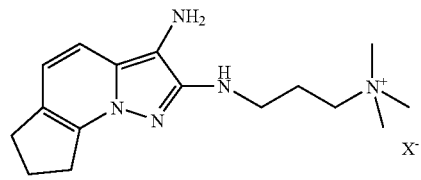

3-[(3-amino-7,8-dihydro-6H-cyclopenta[e]pyrazolo[1,5-a]pyridin-2-yl)amino]-N,N,N-trimethylpropan-1-aminium

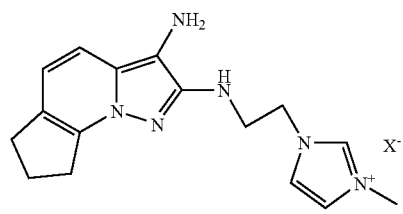

1-{2-[(3-amino-7,8-dihydro-6H-cyclopenta[e]pyrazolo[1,5-a]pyridin-2-yl)amino]ethyl}-3-methyl-1H-imidazol-3-ium

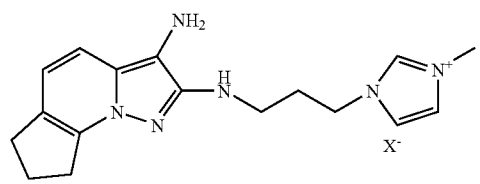

1-{3-[(3-amino-7,8-dihydro-6H-cyclopenta[e]pyrazolo[1,5-a]pyridin-2-yl)amino]propyl}-3-methy-1H-imidazol-3-ium

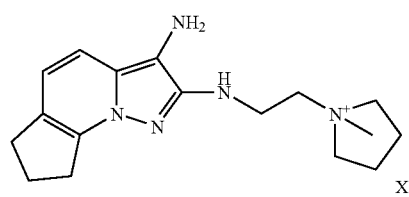

1-{2-[(3-amino-7,8-dihydro-6H-cyclopenta[e]pyrazolo[1,5-a]pyridin-2-yl)amino]ethyl}-1-methylpyrrolidinium

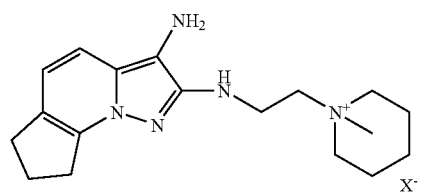

1-{2-[(3-amino-7,8-dihydro-6H-cyclopenta[e]pyrazolo[1,5-a]pyridin-2-yl)amino]ethyl}-1-methylpiperidinium

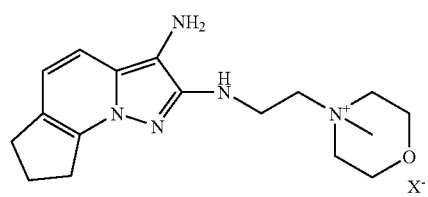

4-{2-[(3-amino-7,8-dihydro-6H-cyclopenta[e]pyrazolo[1,5-a]pyridin-2-yl)amino]ethyl}-4-methylmorpholin-4-ium -continued

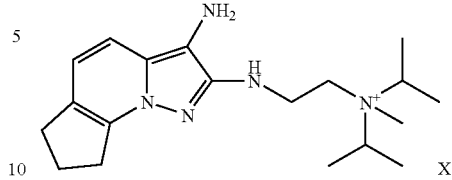

N-{2-[(3-amino-7,8-dihydro-6H-cyclopenta[e]pyrazolo[1,5-a]pyridin-2-yl)amino]ethyl}-N-isopropyl-N-methylpropan-2-aminium

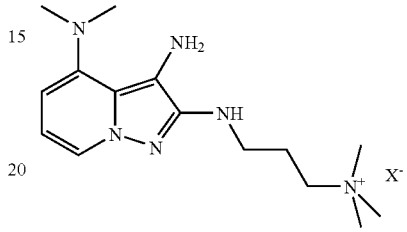

[3-(3-Amino-4-dimethylamino-pyrazolo[1,5-a]pyridin-2-ylamino)-propyl]-trimethyl-ammonium

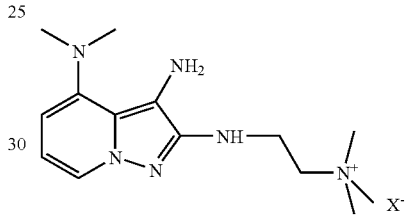

[2-(3-Amino-4-dimethylamino-pyrazolo[1,5-a]pyridin-2-ylamino)-ethyl]-trimethyl-ammonium

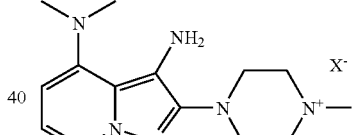

4-(3-Amino-4-dimethylamino-pyrazolo[1,5-a]pyridin-2-yl)-1-methyl-piperazin-1-ium

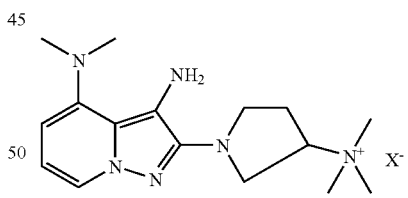

[1-(3-Amino-4-dimethylamino-pyrazolo[1,5-a]pyridin-2-yl)-pyrrolidin-3-yl]-trimethyl-ammonium

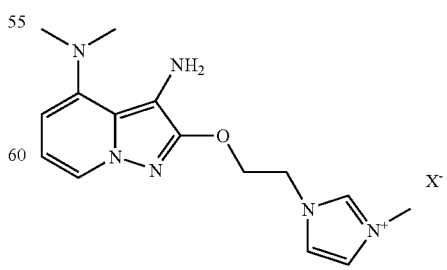

3-[2-(3-Amino-4-dimethylamino-pyrazolo[1,5-a]pyridin-2-yloxy)-ethyl]-1-methyl-3H-imidazol-1-ium -continued

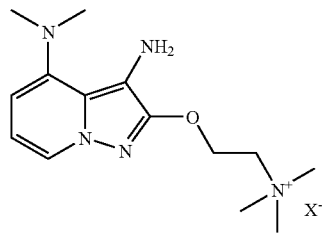

[2-(3-Amino-4-dimethylamino-pyrazolo[1,5-a]pyridin-2-yloxy)-ethyl]-trimethyl-ammonium

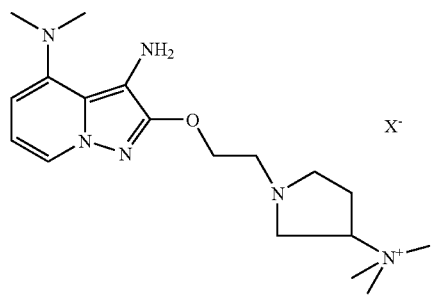

{1-[2-(3-Amino-4-dimethylamino-pyrazolo[1,5-a]pyridin-2-yloxy)-ethyl]-pyrrolidin-3-yl}-trimethyl-ammonium

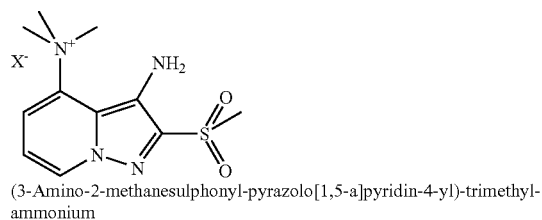

(3-Amino-2-methanesulphonyl-pyrazolo[1,5-a]pyridin-4-yl)-trimethyl-ammonium

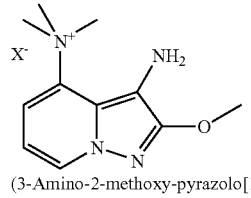

(3-Amino-2-methoxy-pyrazolo[1,5-a]pyridin-4-yl)-trimethyl-ammonium

In a non-limiting embodiment of the present disclosure, $Z_1$ and/or $Z_2$ are chosen from a single bond, a radical —O—, a radical —NR$_6$— in which R$_6$ is chosen from a hydrogen atom, an alkyl radical, or R$_6$ forms, together with at least one of R$_1$ and R$_2$, a heterocycle that is cationic and/or is substituted with a cationic radical.

In another non-limiting embodiment of the present disclosure, R$_6$ together with at least one of R$_1$ and R$_2$, forms a cationic heterocycle or a heterocylcle substituted with a cationic radical. Non-limiting examples of such heterocycles include imidazoles substituted with a quaternary ammonium radical or imidazoliums, piperazines substituted with a quaternary ammonium radical or the piperaziniums, pyrrolidines substituted with a quaternary ammonium radical or the pyrrolidiniums and diazepanes substituted with a quaternary ammonium radical or the diazepaniums.

In a further non-limiting embodiment of the present disclosure, R$_1$ and R$_2$, which may be the same or different, are independently chosen from a hydrogen atom, an alkyl radical which may be interrupted or substituted with a cationic radical, such as, for example, alkylammonium, hydroxyalkylammonium, imidazolium, piperazinium, pyrrolidinium, diazepanium, imidazolyl substituted with a cationic radical, piperazinyl substituted with a cationic radical, pyrrolidinyl substituted with a cationic radical and pyridinyl substituted with a cationic radical.

The radicals R$_3$, R$_4$ and R$_5$, which may be the same or different, are independently chosen from a hydrogen atom and optionally substituted C$_1$-C$_4$ alkyl radicals, such as, for example, methyl, ethyl, hydroxyethyl, aminoethyl, propyl and butyl radicals. In a non-limiting embodiment of the present disclosure, R$_3$, R$_4$ and R$_5$ represent independently a hydrogen atom, and/or a C$_1$-C$_4$ alkyl radical.

According to another non-limiting embodiment of the present disclosure R$_4$ and R$_5$ together form an optionally substituted, saturated or unsaturated ring with 5 to 8 ring members, such as a cyclopentane or cyclohexane.

According to another non-limiting embodiment of the present disclosure, the compounds of formula (I) correspond to those of formula (I'):

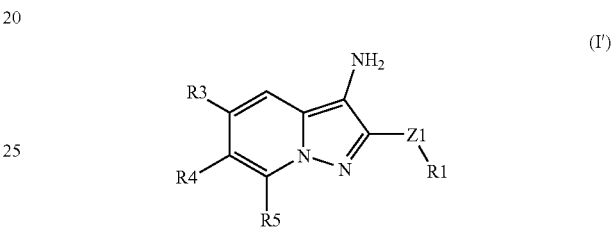

(I')

in which $Z_1$, R$_1$, R$_3$, R$_4$ and R$_5$ are as defined previously.

According to a yet another non-limiting embodiment, in formula (I'), $Z_1$ is chosen from —NH— or NR$_6$, in which R$_6$ forms a heterocycle with R$_1$, said heterocylcle being cationic or substituted with a cationic radical.

As non-limiting examples of these compounds, mention is made of:
2-[(3-aminopyrazolo[1,5-a]pyridin-2-yl)amino]-N,N,N-trimethylethanaminium chloride hydrochloride;
3-[(3-aminopyrazolo[1,5-a]pyridin-2-yl)amino]-N,N,N-trimethylpropan-1-aminium chloride hydrochloride;
2-[(3-aminopyrazolo[1,5-a]pyridin-2-yl)amino]-N,N-diethyl-N-methylethanaminium chloride hydrochloride;
N-{2-[(3-aminopyrazolo[1,5-a]pyridin-2-yl)amino]ethyl}-N-isopropyl-N-methylpropan-2-aminium chloride hydrochloride;
1-{2-[(3-aminopyrazolo[1,5-a]pyridin-2-yl)amino]ethyl}-3-methyl-1H-imidazol-3-ium chloride hydrochloride;
1-{2-[(3-aminopyrazolo[1,5-a]pyridin-2-yl)amino]ethyl}-3-methyl-1H-imidazol-3-ium chloride hydrochloride;
1-{2-[(3-aminopyrazolo[1,5-a]pyridin-2-yl)amino]ethyl}-1-methylpyrrolidinium chloride hydrochloride;
1-{2-[(3-aminopyrazolo[1,5-a]pyridin-2-yl)amino]ethyl}-1-methylpiperidinium chloride hydrochloride;
4-{2-[(3-aminopyrazolo[1,5-a]pyridin-2-yl)amino]ethyl}-4-methylmorpholin-4-ium chloride hydrochloride;
1-{2-[(3-aminopyrazolo[1,5-a]pyridin-2-yl)amino]ethyl}-N,N,N,-trimethylpyrrolidin-3-aminium chloride hydrochloride;
2-[(3-aminopyrazolo[1,5-a]pyridin-2-yl)oxy]-N,N,N-trimethylethanaminium chloride hydrochloride;
2-{2-[(3-aminopyrazolo[1,5-a]pyridin-2-yl)amino]ethyl}-1-methylpyridinium chloride hydrochloride;
3-{2-[(3-aminopyrazolo[1,5-a]pyridin-2-yl)amino]ethyl}-1-methylpyridinium chloride hydrochloride;
4-{2-[(3-aminopyrazolo[1,5-a]pyridin-2-yl)amino]ethyl}-1-methylpyridinium chloride hydrochloride;

1-{2-[(3-aminopyrazolo[1,5-a]pyridin-2-yl)oxy]ethyl}-1-methylpyrrolidinium chloride hydrochloride;

1-{2-[(3-aminopyrazolo[1,5-a]pyridin-2-yl)oxy]ethyl}-1-methylpiperidinium chloride hydrochloride;

N-{2-[(3-aminopyrazolo[1,5-a]pyridin-2-yl)oxy]ethyl}-N-isopropyl-N-methylpropan-2-aminium chloride hydrochloride;

4-{2-[(3-aminopyrazolo[1,5-a]pyridin-2-yl)oxy]ethyl}-4-methylmorpholin-4-ium chloride hydrochloride;

2-{2-[(3-aminopyrazolo[1,5-a]pyridin-2-yl)oxy]ethyl}-1-methylpyridinium chloride hydrochloride;

3-{2-[(3-aminopyrazolo[1,5-a]pyridin-2-yl)oxy]ethyl}-1-methylpyridinium chloride hydrochloride;

4-{2-[(3-aminopyrazolo[1,5-a]pyridin-2-yl)oxy]ethyl}-1-methylpyridinium chloride hydrochloride;

2-[(3-amino-6,7-dimethylpyrazolo[1,5-a]pyridin-2-yl)amino]-N,N,N-trimethylethanaminium chloride hydrochloride;

N-{2-[(3-amino-6,7-dimethylpyrazolo[1,5-a]pyridin-2-yl)amino]ethyl}-N-isopropyl-N-methylpropan-2-aminium chloride hydrochloride;

1-{2-[(3-amino-6,7-dimethylpyrazolo[1,5-a]pyridin-2-yl)amino]ethyl}-1-methylpyrrolidinium chloride hydrochloride;

1-{2-[(3-amino-6,7-dimethylpyrazolo[1,5-a]pyridin-2-yl)amino]ethyl}-1-methylpiperidium chloride hydrochloride;

4-{2-[(3-amino-6,7-dimethylpyrazolo[1,5-a]pyridin-2-yl)amino]ethyl}-4-methylmorpholin-4-ium chloride hydrochloride;

2-{2-[(3-amino-6,7-dimethylpyrazolo[1,5-a]pyridin-2-yl)amino]ethyl}-1-methylpyridinium chloride hydrochloride;

3-{2-[(3-amino-6,7-dimethylpyrazolo[1,5-a]pyridin-2-yl)amino]ethyl}-1-methylpyridinium chloride hydrochloride;

4-{2-[(3-amino-6,7-dimethylpyrazolo[1,5-a]pyridin-2-yl)amino]ethyl}-1-methylpyridinium chloride hydrochloride;

2-[(3-amino-6,7-dimethylpyrazolo[1,5-a]pyridin-2-yl)oxy]-N,N,N-trimethylethanaminium chloride hydrochloride;

1-{2-[(3-amino-6,7-dimethylpyrazolo[1,5-a]pyridin-2-yl)oxy]ethyl}-1-methylpyrrolidinium chloride hydrochloride;

1-{2-[(3-amino-6,7-dimethylpyrazolo[1,5-a]pyridin-2-yl)oxy]ethyl}-1-methylpiperidium chloride hydrochloride;

4-{2-[(3-amino-6,7-dimethylpyrazolo[1,5-a]pyridin-2-yl)oxy]ethyl}-4-methylmorpholin-4-ium chloride hydrochloride;

2-{2-[(3-amino-6,7-dimethylpyrazolo[1,5-a]pyridin-2-yl)oxy]ethyl}-1-methylpyridinium chloride hydrochloride;

3-{2-[(3-amino-6,7-dimethylpyrazolo[1,5-a]pyridin-2-yl)oxy]ethyl}-1-methylpyridinium chloride hydrochloride;

4-{2-[(3-amino-6,7-dimethylpyrazolo[1,5-a]pyridin-2-yl)oxy]ethyl}-1-methylpyridinium chloride hydrochloride;

2-[(3-amino-7,8-dihydro-6H-cyclopenta[e]pyrazolo[1,5-a]pyridin-2-yl)amino]-N,N,N-trimethylethanaminium chloride hydrochloride;

N-{2-[(3-amino-7,8-dihydro-6H-cyclopenta[e]pyrazolo[1,5-a]pyridin-2-yl)amino]ethyl}-N-isopropyl-N-methylpropan-2-aminium chloride hydrochloride;

1-{2-[(3-amino-7,8-dihydro-6H-cyclopenta[e]pyrazolo[1,5-a]pyridin-2-yl)amino]ethyl}-1-methylpyrrolidinium chloride hydrochloride;

1-{2-[(3-amino-7,8-dihydro-6H-cyclopenta[e]pyrazolo[1,5-a]pyridin-2-yl)amino]ethyl}-1-methylpiperidinium chloride hydrochloride;

4-{2-[(3-amino-7,8-dihydro-6H-cyclopenta[e]pyrazolo[1,5-a]pyridin-2-yl)amino]ethyl}-4-methylmorpholin-4-ium chloride hydrochloride;

2-{2-[(3-amino-7,8-dihydro-6H-cyclopenta[e]pyrazolo[1,5-a]pyridin-2-yl)amino]ethyl}-1-methylpyridinium chloride hydrochloride;

3-{2-[(3-amino-7,8-dihydro-6H-cyclopenta[e]pyrazolo[1,5-a]pyridin-2-yl)amino]ethyl}-1-methylpyridinium chloride hydrochloride;

4-{2-[(3-amino-7,8-dihydro-6H-cyclopenta[e]pyrazolo[1,5-a]pyridin-2-yl)amino]ethyl}-1-methylpyridinium chloride hydrochloride;

2-[(3-amino-7,8-dihydro-6H-cyclopenta[e]pyrazolo[1,5-a]pyridin-2-yl)oxy]-N,N,N-trimethylethanaminium chloride hydrochloride;

N-{2-[(3-amino-7,8-dihydro-6H-cyclopenta[e]pyrazolo[1,5-a]pyridin-2-yl)oxy]ethyl}-N-isopropyl-N-methylpropan-2-aminium chloride hydrochloride;

3-{2-[(3-amino-7,8-dihydro-6H-cyclopenta[e]pyrazolo[1,5-a]pyridin-2-yl)oxy]ethyl}-1-methylpyridinium chloride hydrochloride;

2-{2-[(3-amino-7,8-dihydro-6H-cyclopenta[e]pyrazolo[1,5-a]pyridin-2-yl)oxy]ethyl}-1-methylpyridinium chloride hydrochloride;

4-{2-[(3-amino-7,8-dihydro-6H-cyclopenta[e]pyrazolo[1,5-a]pyridin-2-yl)oxy]ethyl}-1-methylpyridinium chloride hydrochloride;

1-{2-[(3-amino-7,8-dihydro-6H-cyclopenta[e]pyrazolo[1,5-a]pyridin-2-yl)oxy]ethyl}-1-methylpyrrolidinium chloride hydrochloride;

1-{2-[(3-amino-7,8-dihydro-6H-cyclopenta[e]pyrazolo[1,5-a]pyridin-2-yl)oxy]ethyl}-1-methylpiperidinium chloride hydrochloride;

4-{2-[(3-amino-7,8-dihydro-6H-cyclopenta[e]pyrazolo[1,5-a]pyridin-2-yl)oxy]ethyl}-4-methylmorpholin-4-ium chloride hydrochloride;

2-{2-[(3-amino-7,8-dihydro-6H-cyclopenta[e]pyrazolo[1,5-a]pyridin-2-yl)oxy]ethyl}-1-methylpyridinium chloride hydrochloride;

3-{2-[(3-amino-7,8-dihydro-6H-cyclopenta[e]pyrazolo[1,5-a]pyridin-2-yl)oxy]ethyl}-1-methylpyridinium chloride hydrochloride; and 4-{2-[(3-amino-7,8-dihydro-6H-cyclopenta[e]pyrazolo[1,5-a]pyridin-2-yl)oxy]ethyl}-1-methylpyridinium chloride hydrochloride;

In another non-limiting embodiment of the present disclosure, the derivative of formula (I) is such that $Z_1$ is NH and $R_1$ is a cationic radical, or $Z_1$ is —O— and $R_1$ is a cationic radical. The oxidation base or bases of the present disclosure may each be present, for example in an amount ranging from 0.001% to 10%% by weight, such as from 0.005% to 6% by weight, relative to the total weight of the dyeing composition.

The dyeing composition of the present disclosure may contain at least one coupler conventionally used for the dyeing of keratin fibers. As non-limiting examples of such couplers, mention is made of meta-phenylenediamines, meta-aminophenols, meta-diphenols, naphthalenic couplers, heterocyclic couplers and the addition salts thereof.

Further non-limiting examples of couplers that may be utilized in the present disclosure include 2-methyl 5-aminophenol, 5-N-(β-hydroxyethyl)amino 2-methyl phenol, 6-chloro-2-methyl-5-aminophenol, 3-amino phenol, 1,3-dihydroxy benzene, 1,3-dihydroxy 2-methyl benzene, 4-chloro 1,3-dihydroxy benzene, 2,4-diamino 1-(β-hydroxyethyloxy) benzene, 2-amino 4-(β-hydroxyethylamino) 1-methoxybenzene, 1,3-diamino benzene, 1,3-bis-(2,4-diaminophenoxy) propane, 3-ureido aniline, 3-ureido 1-dimethylamino benzene, sesamol, 1-β-hydroxyethylamino-3,4-methylene-dioxybenzene, α-naphthol, 2 methyl-1-naphthol, 6-hydroxy indole, 4-hydroxy indole, 4-hydroxy N-methyl indole, 2-amino-3-hydroxy pyridine, 6-hydroxy benzomorpholine 3,5-diamino-2,6-dimethoxypyridine, 1-N-(β-hydroxyethyl) amino-3,4-methylene dioxybenzene, 2,6-bis-(β-hydroxy-ethylamino)toluene and the acid addition salts thereof.

In a non-limiting embodiment of the present disclosure, the at least one coupler can be present in the composition in an amount ranging from about 0.001% to 10% by weight, relative to the total weight of the dyeing composition, such as ranging from 0.005% to 6% by weight.

In addition, the compositions of the present disclosure may contain at least one additional oxidation base conventionally used in oxidation dyeing other than those described previously. As non-limiting examples of such oxidation bases, mention may be made of: para-phenylenediamines, bis-phenylalkylenediamines, para-aminophenols, bis-para-aminophenols, ortho-aminophenols, ortho-phenylenediamines, heterocyclic bases different from the derivatives of formula (I) as defined previously and the addition salts thereof.

As non-limiting examples of para-phenylenediamines that may be utilized in the present disclosure, mention is made of: para-phenylenediamine, para-toluylenediamine, 2-chloro para-phenylenediamine, 2,3-dimethyl para-phenylenediamine, 2,6-dimethyl para-phenylenediamine, 2,6-diethyl para-phenylenediamine, 2,5-dimethyl para-phenylenediamine, N,N-dimethyl para-phenylenediamine, N,N-diethyl para-phenylenediamine, N,N-dipropyl para-phenylenediamine, 4-amino N,N-diethyl 3-methyl aniline, N,N-bis-(β-hydroxyethyl) para-phenylenediamine, 4-N,N-bis-(β-hydroxyethyl)amino 2-methyl aniline, 4-N,N-bis-(β-hydroxyethyl)amino 2-chloro aniline, 2-β-hydroxyethyl para-phenylenediamine, 2-fluoro para-phenylenediamine, 2-isopropyl para-phenylenediamine, N-(β-hydroxypropyl) para-phenylenediamine, 2-hydroxymethyl para-phenylenediamine, N,N-dimethyl 3-methyl para-phenylenediamine, N,N-(ethyl, β-hydroxyethyl) para-phenylenediamine, N-(β, γ-dihydroxypropyl) para-phenylenediamine, N-(4'-aminophenyl) para-phenylenediamine, N-phenyl para-phenylenediamine, 2-β-hydroxyethyloxy para-phenylenediamine, 2-β-acetylaminoethyloxy para-phenylenediamine, N-(β-methoxyethyl) para-phenylenediamine, 4-aminophenylpyrrolidine, 2-thienyl para-phenylenediamine, 2-β hydroxyethylamino 5-amino-toluene, 3-hydroxy 1-(4'-aminophenyl)pyrrolidine and the acid addition salts thereof.

Among the para-phenylenediamines mentioned above, further non-limiting mention is made of para-phenylenediamine, para-toluylenediamine, 2-isopropyl para-phenylenediamine, 2-β-hydroxyethyl para-phenylenediamine, 2-β-hydroxyethyloxy para-phenylenediamine, 2,6-dimethyl para-phenylenediamine, 2,6-diethyl para-phenylenediamine, 2,3-dimethyl para-phenylenediamine, N,N-bis-(β-hydroxyethyl) para-phenylenediamine, 2-chloro para-phenylenediamine, 2-β-acetylaminoethyloxy para-phenylenediamine, and the acid addition salts thereof.

As non-limiting examples of bis-phenylalkylenediamines that may be utilized in the present disclosure, non-limiting mention is made of: N,N'-bis-(β-hydroxyethyl) N,N'-bis-(4'-aminophenyl) 1,3-diamino propanol, N,N'-bis-(β-hydroxyethyl) N,N'-bis-(4'-aminophenyl) ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl) tetramethylenediamine, N,N'-bis-(ethyl) N,N'-bis-(4'-amino, 3'-methylphenyl) ethylenediamine, 1,8-bis-(2,5-diamino phenoxy)-3,6-dioxaoctane, and the acid addition salts thereof.

As non-limiting examples of para-aminophenols that may be utilized in the present disclosure, mention is made of: para-aminophenol, 4-amino 3-methylphenol, 4-amino 3-fluorophenol, 4-amino 3-hydroxymethylphenol, 4-amino 2-methylphenol, 4-amino 2-hydroxymethylphenol, 4-amino 2-methoxymethylphenol, 4-amino 2-aminomethylphenol, 4-amino 2-(β-hydroxyethyl aminomethyl)phenol, 4-amino 2-fluorophenol, and the acid addition salts thereof.

As non-limiting examples of ortho-aminophenols that may be utilized in the present disclosure, mention is made of: 2-aminophenol, 2-amino 5-methylphenol, 2-amino 6-methylphenol, 5-acetamido 2-aminophenol, and the acid addition salts thereof.

As non-limiting examples of heterocyclic bases that may be utilized in the present disclosure, mention is made of: the pyridine derivatives, the pyrimidine derivatives and the pyrazole derivatives.

As non-limiting examples of the aforesaid pyridine derivatives, mention is made of the compounds described, for example, in British Patent Nos. GB 1 026 978 and GB 1 153 196, such as 2,5-diaminopyridine, 2-(4-methoxyphenyl) amino 3-aminopyridine, 2,3-diamino 6-methoxypyridine, 2-(β-methoxyethyl)amino 3-amino 6-methoxypyridine, 3,4-diaminopyridine, and the acid addition salts thereof.

Non-limiting examples of other additional pyridine oxidation bases different from the oxidation bases of formula (I) that may be used in the present disclosure include the 3-aminopyrazolo-[1,5-a]-pyridine oxidation bases and their addition salts, as described, for example in French Patent Application No. FR 2 801 308. Further non-limiting examples of such pyridine oxidation bases include: pyrazolo[1,5-a]pyridin-3-ylamine; 2-acetylamino pyrazolo-[1,5-a]pyridin-3-ylamine; 2-morpholin-4-yl-pyrazolo[1,5-a]pyridin-3-ylamine; 3-amino-pyrazolo[1,5-a]pyridin-2-carboxylic acid; 2-methoxy-pyrazolo[1,5-a]pyridin-3-ylamino; (3-amino-pyrazolo[1,5-a]pyridin-7-yl)-methanol; 2-(3-amino-pyrazolo[1,5-a]pyridin-5-yl)-ethanol; 2-(3-amino-pyrazolo[1,5-a]pyridin-7-yl)-ethanol; (3-amino-pyrazolo[1,5-a]pyridin-2-yl)-methanol; 3,6-diamino-pyrazolo[1,5-a]pyridine; 3,4-diamino-pyrazolo[1,5-a]pyridine; pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)-amino]-ethanol; 2-[(3-amino-pyrazolo[1,5-a]pyridin-7-yl)-(2-hydroxyethyl)-amino]-ethanol; 3-amino-pyrazolo[1,5-a]pyridine-5-ol; 3-amino-pyrazolo[1,5-a]pyridine-4-ol; 3-amino-pyrazolo[1,5-a]pyridine-6-ol; 3-amino-pyrazolo[1,5-a]pyridine-7-ol; and the acid or alkaline addition salts thereof.

As non-limiting examples of pyrimidine derivatives that may be utilized in the present disclosure, mention is made of the compounds described in patents DE 23 59 399; JP 88-169571; JP 05-63124; EP 0 770 375 or the patent application WO 96/15765, such as 2,4,5,6-tetra-aminopyrimidine, 4-hydroxy 2,5,6-triaminopyrimidine, 2-hydroxy 4,5,6-triaminopyrimidine, 2,4-dihydroxy 5,6-diaminopyrimidine, 2,5,6-triaminopyrimidine, and pyrazolopyrimidine derivatives such as those mentioned in patent application FR-A-2 750 048 and among which non-limiting mention may be made of pyrazolo-[1,5-a]-pyrimidine-3,7-diamine; 2,5-dimethyl pyrazolo-[1,5-a]-pyrimidine-3,7-diamine; pyrazolo-[1, 5-a]-pyrimidine-3,5-diamine; 2,7-dimethyl pyrazolo-[1,5-a]-pyrimidine-3,5-diamine; 3-amino pyrazolo-[1,5-a]-pyrimidin-7-ol; 3-amino pyrazolo-[1,5-a]-pyrimidin-5-ol; 2-(3-amino pyrazolo-[1,5-a]-pyrimidin-7-ylamino)-ethanol, 2-(7-amino pyrazolo-[1,5-a]-pyrimidin-3-ylamino)-ethanol, 2-[(3-amino-pyrazolo[1,5-a]pyrimidin-7-yl)-(2-hydroxy-ethyl)-amino]-ethanol, 2-[(7-amino-pyrazolo[1,5-a]pyrimidin-3-yl)-(2-hydroxy-ethyl)-amino]-ethanol, 5,6-dimethyl pyrazolo-[1,5-a]-pyrimidine-3,7-diamine, 2,6-dimethyl pyrazolo-[1,5-a]-pyrimidine-3,7-diamine, 2,5, N 7, N 7-tetramethyl pyrazolo-[1,5-a]-pyrimidine-3,7-diamine, 3-amino-5-methyl-7-imidazolylpropylamino pyrazolo-[1,5-a]-pyrimidine, the acid addition salts thereof, and the tautomeric forms thereof, when a tautomeric equilibrium exists.

As non-limiting examples of pyrazole derivatives that may be utilized in the present disclosure, mention is made of the compounds described in patents DE 38 43 892, DE 41 33 957 and patent applications WO 94/08969, WO 94/08970, FR-A-2 733 749 and DE 195 43 988 such as 4,5-diamino 1-methyl pyrazole, 4,5-diamino 1-(β-hydroxyethyl) pyrazole, 3,4-diamino pyrazole, 4,5-diamino 1-(4'-chlorobenzyl) pyrazole, 4,5-diamino 1,3-dimethyl pyrazole, 4,5-diamino 3-methyl 1-phenyl pyrazole, 4,5-diamino 1-methyl 3-phenyl pyrazole, 4-amino 1,3-dimethyl 5-hydrazino pyrazole, 1-benzyl 4,5-diamino 3-methyl pyrazole, 4,5-diamino 3-tert-butyl 1-methyl pyrazole, 4,5-diamino 1-tert-butyl 3-methyl pyrazole, 4,5-diamino 1-(β-hydroxyethyl) 3-methyl pyrazole, 4,5-diamino 1-ethyl 3-methyl pyrazole, 4,5-diamino 1-ethyl 3-(4'-methoxyphenyl) pyrazole, 4,5-diamino 1-ethyl 3-hydroxymethyl pyrazole, 4,5-diamino 3-hydroxymethyl 1-methyl pyrazole, 4,5-diamino 3-hydroxymethyl 1-isopropyl pyrazole, 4,5-diamino 3-methyl 1-isopropyl pyrazole, 4-amino 5-(2'-aminoethyl)amino 1,3-dimethyl pyrazole, 3,4,5-triamino pyrazole, 1-methyl 3,4,5-triamino pyrazole, 3,5-diamino 1-methyl 4-methylamino pyrazole, 3,5-diamino 4-(β-hydroxyethyl)amino 1-methyl pyrazole, and the acid addition salts thereof.

In a non-limiting embodiment of the present disclosure, the at least one additional oxidation base in the composition of the present disclosure may each be present in the dyeing composition in an amount ranging from 0.001 to 10 wt. %, such as from 0.005 to 6 wt. %, relative to the total weight of the dyeing composition.

As non-limiting examples of the addition salts of the aforementioned at least one additional oxidation base and/or at least one additional coupler that can be used in the present disclosure, mention is made of the acid addition salts with an acid such as the hydrochlorides, hydrobromides, sulphates, citrates, succinates, tartrates, lactates, tosylates, benzenesulphonates, phosphates and acetates and the alkaline addition salts with a base such as sodium hydroxide, potassium hydroxide, ammonia, amines or alkanolamines.

In addition, the dyeing composition according to the present disclosure can also contain at least one direct dye, which may be chosen from, for example, the nitro dyes of the benzene series, the azo direct dyes, and the methine direct dyes. These direct dyes can be of a non-ionic, anionic or cationic nature.

As used herein, the suitable medium for dyeing, also called dyeing support, is a cosmetic medium that may comprise water, or a mixture of water and at least one organic solvent for dissolving the compounds that would not be sufficiently soluble in water. Non-limiting examples of such organic solvents include the $C_1$-$C_4$ lower alkanols such as ethanol and isopropanol; polyols and polyol ethers such as 2-butoxyethanol, propylene glycol, monomethyl ether of propylene glycol, the monoethyl ether and monomethyl ether of diethylene glycol, as well as the aromatic alcohols such as benzyl alcohol or phenoxyethanol, and mixtures thereof.

In a non-limiting embodiment of the present disclosure, the solvents are present in an amount ranging from 1% to 40% by weight, such as from 5 to 30% by weight, relative to the total weight of the dyeing composition.

The dyeing composition according to the present disclosure may also contain at least one additive conventionally used in compositions for dyeing the hair, including, but not limited to anionic, cationic, non-ionic, amphoteric, zwitterionic surfactants or mixtures thereof; anionic, cationic, non-ionic, amphoteric, zwitterionic polymers or mixtures thereof, inorganic or organic thickeners, including anionic, cationic, non-ionic and amphoteric associative polymeric thickeners; antioxidants, penetrants, sequestering agents, perfumes, buffers, dispersants, conditioning agents such as volatile or non-volatile, modified or unmodified silicones; film-forming agents, ceramides, preservatives, and opacifiers.

In a non-limiting embodiment of the present disclosure, the at least one additive may each be present in the dyeing composition in an amount ranging from 0.01% to 20% by weight, relative to the total weight of the dyeing composition.

A person skilled in the art will of course make sure that any additional compound or compounds are selected in such a way that the beneficial properties intrinsic to the oxidation dyeing composition according to the present disclosure are not adversely affected, or are not substantially adversely affected, by the addition or additions envisaged.

In a non-limiting embodiment of the present disclosure, the pH of the dyeing composition ranges from 3 to 12, such as from 5 to 11. The pH can be adjusted to the desired value by means of acidifying or alkalizing agents usually employed in the dyeing of keratin fibers or alternatively by means of conventional buffering systems.

As non-limiting examples of acidifying agents that may be utilized according to the present disclosure, mention is made of: mineral or organic acids such as hydrochloric acid, orthophosphoric acid, sulphuric acid, and carboxylic acids such as acetic acid, tartaric acid, citric acid, lactic acid, and sulphonic acids.

As non-limiting examples of alkalizing agents that may be utilized according to the present disclosure, mention is made of: ammonia, alkali metal carbonates, alkanolamines such as the mono-, di- and tri-ethanolamines and derivatives thereof, the hydroxides of sodium or potassium and the compounds of formula (II):

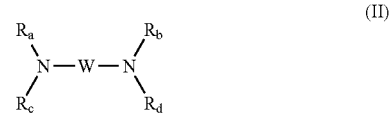

(II)

in which W is a propylene residue optionally substituted with a hydroxyl group or a $C_1$-$C_4$ alkyl radical; and $R_a$, $R_b$, $R_c$ and $R_d$, which may be the same or different, are independently chosen from a hydrogen atom, $C_1$-$C_4$ alkyl radicals and $C_1$-$C_4$ hydroxyalkyl radicals.

The dyeing composition according to the present disclosure can be in various forms, such as in the form of liquids, creams, gels, or in any other form that is suitable for carrying out dyeing of keratin fibers, such as human hair.

The method of the present disclosure is a method in which the composition according to the present disclosure as defined previously is applied to the fibers, and the color is developed by means of at least one oxidizing agent. The color can be developed at acid, neutral or alkaline pH and the at least one oxidizing agent can be added to the composition of the present disclosure right at the moment of use or it can be used as part of an oxidizing composition containing it, applied simultaneously with or sequentially to the composition of the present disclosure.

According to another embodiment, the composition according to the present disclosure is mixed, such as at the moment of use, with a composition comprising, in a medium suitable for dyeing, at least one oxidizing agent, said at least one oxidizing agent being present in an amount sufficient for developing a coloration. The mixture obtained is then applied to the keratin fibers. After a waiting time ranging from 3 to 50 minutes, such as from 5 to 30 minutes, the keratin fibers are rinsed, washed with shampoo, rinsed again and then dried.

Non-limiting examples of oxidizing agents which may be utilized according to the present disclosure include, for example, hydrogen peroxide, urea peroxide, alkali metal bromates, per-salts such as perborates and persulphates, peracids and the oxidase enzymes of which we may mention the peroxidases, 2-electron oxidoreductases such as uricases and 4-electron oxygenases such as laccases. In a further non-limiting embodiment, hydrogen peroxide is utilized as the oxidizing agent.

The oxidizing composition may also contain at least one additional additive conventionally used in compositions for dyeing the hair, such as those described previously.

In a non-limiting embodiment of the present disclosure, the pH of the oxidizing composition comprising the at least one oxidizing agent is such that after mixing with the dyeing composition, the pH of the resultant composition applied to the keratin fibers ranges from 3 to 12, such as from 5 to 11. The pH of the oxidizing compositions may be adjusted to the desired value by means of acidifying or alkalizing agents, such as those described previously.

The ready-to-use composition which is finally applied to the keratin fibers may be in various forms, such as in the form of a liquid, cream, gel or in any other form suitable for carrying out dyeing of keratin fibers, such as human hair.

The present disclosure also relates to a dyeing "kit" with several compartments, in which at least one first compartment comprises the dyeing composition of the present disclosure discussed above and at least one second compartment contains at least one oxidizing composition. This kit may be equipped with an applicator for delivering the desired mixture onto the hair, such as the kits described in French Patent No. FR-2 586 913.

In a non-limiting embodiment of the present disclosure, this kit is utilized to dye keratin fibers by a method that comprises mixing a dyeing composition comprising at least one oxidation base of formula (I) with at least one oxidizing agent, and applying the resultant mixture to keratin fibers for a period of time that is sufficient to develop the desired coloration.

In another non-limiting embodiment, the present disclosure relates to the use of a pyrazolopyridine derivative of formula (I) or of one of its salts of addition as previously discussed for the oxidation dyeing of keratin fibers, for example human keratin fibers such as the hair.

The compounds of formula (I) may, for example, be obtained from intermediates and by synthetic routes described in the literature, including, for example, the following documents: J. Het. Chem., 2001, 38(3), 613-616; Helvetica Chimica Acta, 1950, 33, 1183-1194; J. Org. Chem., 23, 2029 (1958); J. Am. Chem. Soc., 73, 3240 (1951); J. Am. Chem. Soc., 84, 590 (1962); Justus Liebig Ann. Chem., 686, 134 (1965); Tetrahedron Lett., 31, 2859-2862 (1973), U.S. Pat. Nos. 4,128,425 and 2,841,584 and the references cited therein.

According to a non-limiting embodiment, the compounds of formula (I) may be synthesized according to the following scheme:

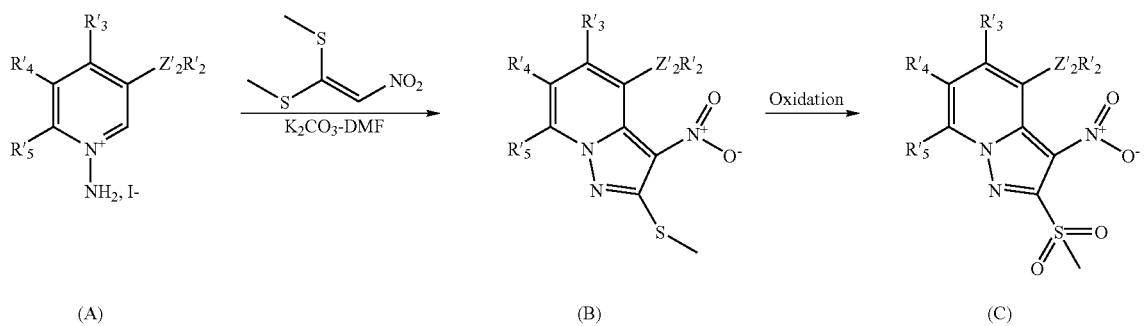

-continued

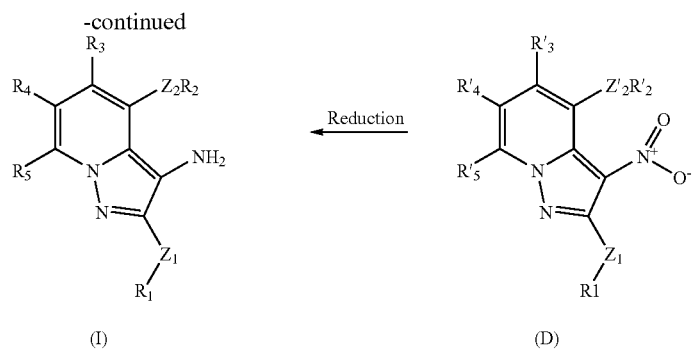

in which $Z_1$, $R_1$, $Z'_2$, $R'_2$, $R'_3$, $R'_4$ and $R'_5$ have the same meanings as $Z_2$, $R_2$, $R_3$, $R_4$ and $R_5$ as defined above, or are precursors thereof, permitting the compounds of the formula to be obtained.

The manner in which compound (B) may be obtained from compound (A) can be carried out, for example, according to the conditions described in HETEROCYCLES, Vol. 6, N° 4, 1977.

Mention may be made, by way of non-limiting example, of the following synthesis:

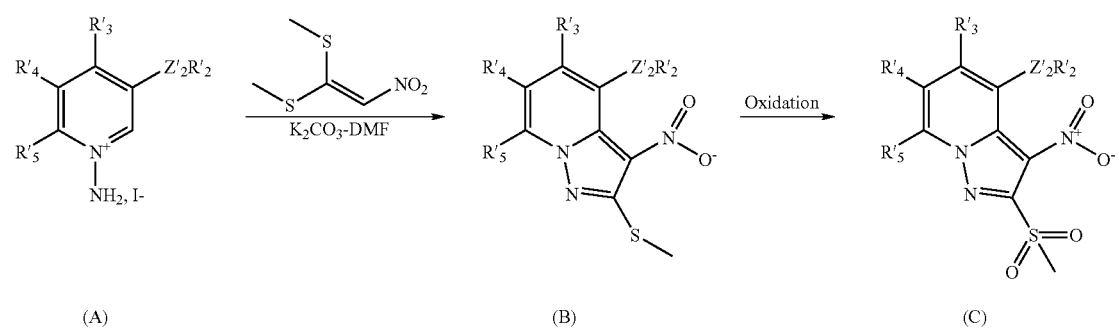

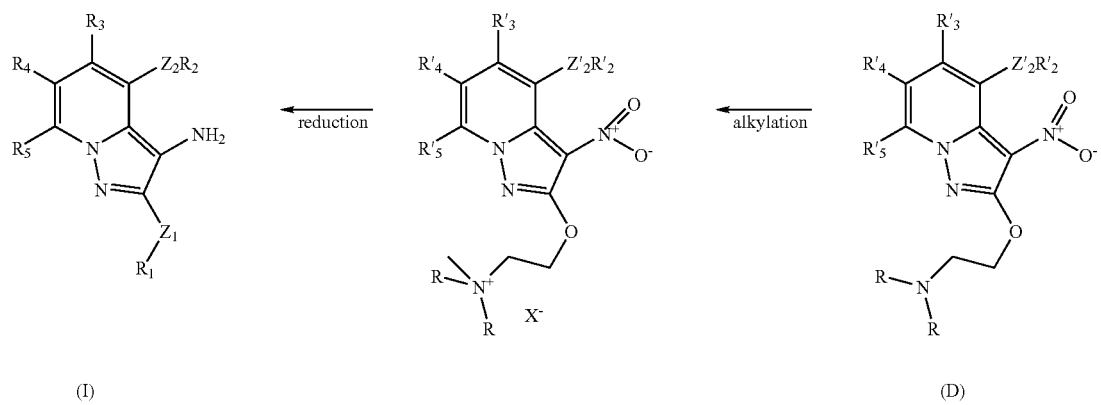

Another non-limiting example of a possible synthetic route is:

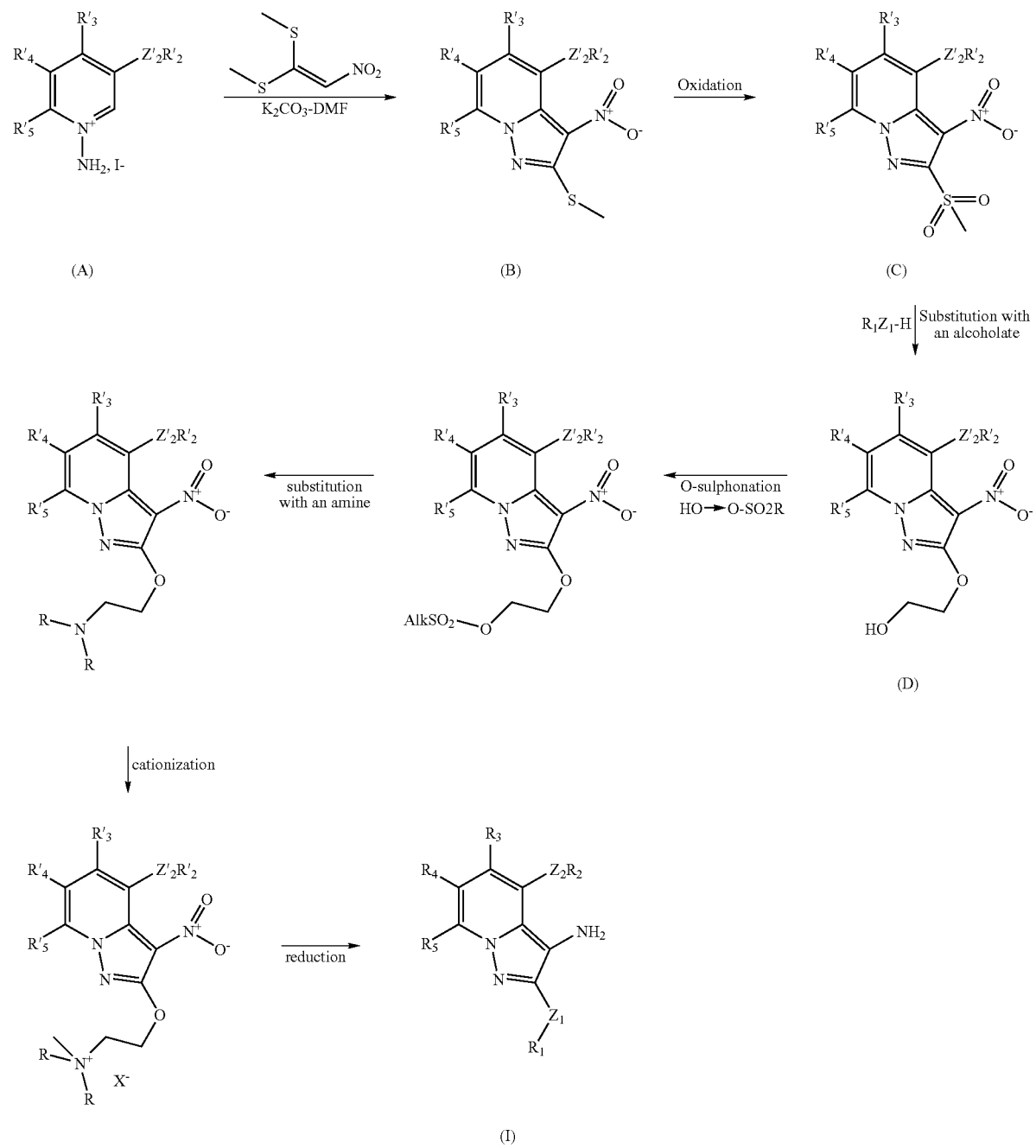

In the above syntheses, the last stage is always a reduction, by which (I) is obtained from compounds (D) for example, by carrying out a hydrogenation reaction by heterogeneous catalysis in the presence of Pd/C, Pd(II)/C, Ni/Ra, etc., or alternatively by carrying out a reaction of reduction by a metal, for example by zinc, iron, tin, etc. (see Advanced Organic Chemistry, 3rd edition, J. March, 1985, Willey Interscience, and Reduction in Organic Chemistry, M. Hudlicky, 1983, Ellis Horwood Series Chemical Science).

The present disclosure also relates to the intermediates of formulae (A) and (B) as defined above, with the exception of the iodide compound of 1-amino-3-methylpyridinium and 4-methyl-2-(methylsulphanyl)-3-nitropyrazolo[1,5-a]pyridine.

The present disclosure further relates to the intermediates of formulae (C) and (D) as defined above as well as the any products between (D) and formula (I).

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, the numerical values set forth in the specific example are reported as precisely as possible. Any numerical value, however, inherently contain certain errors necessarily resulting from the standard deviation found in their respective testing measurements.

The examples below are non-limiting illustrations of the present disclosure. All of the amounts indicated percentage by weight, unless otherwise indicated.

EXAMPLES

Example 1

Stage 1

Synthesis of 2-methylsulphanyl-3-nitro-pyrazolo[1,5-a]pyridine

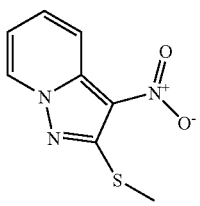

2-Methylsulphanyl-3-nitro-pyrazolo[1,5-a]pyridine

A solution of 111 g of 1-N-aminopyridinium (0.5 mol) in DMF (500 ml) was prepared in a 2-liter three-necked flask equipped with a mechanical stirrer and an internal temperature sensor and maintained under a stream of nitrogen.

Potassium carbonate (207.3, 3 eq.) was then added in one go, followed by 1,1-bis(methylthio)-2-nitroethylene (165.2 g, 2 eq.), also in one go. The mass of the reaction mixture increased. 500 ml of DMF was added in order to make the reaction mixture more fluid.

The resultant mixture was stirred for 48 hours at room temperature, after which it was poured into 4 liters of ice water. The precipitate that formed was filtered and washed with plenty of water (5 liters), and then dried at 80° C. under vacuum.

The excess 1,1-bis(methylthio)-2-nitroethylene (30 mol. % determined by $^1$H-NMR) was removed from the solid thus obtained by re-pasting in ethyl acetate. After draining and drying, 72 g of a yellowish beige solid corresponding to the expected product was obtained.

$^1$H-NMR (300 MHz, DMSO-$d_6$): 8.98 (1H, d); 8.20 (1H, d), 7.89 (1H, m), 7.36 (1H, m), 2.63 (3H, s).

Stage 2

Synthesis of 2-methanesulphonyl-3-nitro-pyrazolo[1,5-a]pyridine

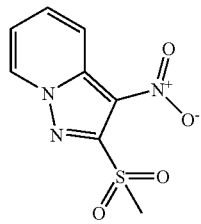

2-Methanesulphonyl-3-nitro-pyrazolo[1,5-a]pyridine 880 g of Oxone (5 eq.), 2 liters of water and 60 g of 2-methylsulphonyl-3-nitro-pyrazolo[1,5-a]pyridine (0.287 eq.) obtained previously were loaded successively in a 4-liter three-necked flask equipped with a mechanical stirrer and an internal temperature sensor. The whole mixture was then stirred at room temperature.

To complete the reaction, Oxone (120 g, 0.7 eq.) was added, and after stirring for 4 hours at room temperature, the reaction ended.

The solid that formed was drained and washed with plenty of water until a filtrate is obtained that no longer contains peroxide. The solid was then placed under vacuum at 40° C. over $P_2O_5$.

59 g of the expected product was obtained in the form of a yellow-beige powder.

NMR analyses ($^1$H 400 MHz and $^{13}$C 100.61 MHz DMSO $d_6$) were consistent with the expected structure.

Stage 3

Synthesis of N-N-dimethyl-N'(3-nitro-pyrazolo[1,5-a]pyridin-2-yl)-ethane-1-2-diamine

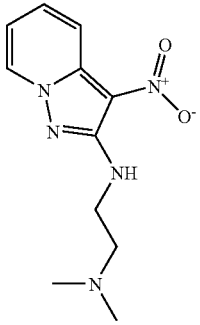

N,N-Dimethyl-N'-(3-nitro-pyrazolo[1,5-a]pyridin-2-yl)-ethane-1,2-diamine 34.5 g (0.143 mol) 2-methanesulphanyl-3-nitro-pyrazolo [1,5-a]pyridine and 71 g (0.805 mol) of dimethyl-ethylene-diamine were put in a 500-ml three-necked flask equipped with a bulb condenser, a thermometer and a magnetic stirrer. While stirring, the mixture was heated to 80° C. on an oil bath for 5 hours, while being monitored by TLC (eluent: 98:2 dichloromethane/methanol).

The reaction mixture was cooled to room temperature, and the yellow compound that was precipitated in the mixture was drained on a No. 4 frit and then washed several times with water. The washed mixture was then dried at 40° C. under vacuum in the presence of $P_2O_5$, and 35 g of a yellow solid corresponding to the expected compound was recovered.

NMR analyses ($^1$H 400 MHz and $^{13}$C 100.61 MHz DMSO $d_6$) were consistent with the expected structure.

The mass of the expected compound $C_{11}H_{11}N_5O_2$ was determined by mass spectrometry.

Stage 4

Synthesis of N,N,N-trimethyl-2-[(3-nitropyrazolo[1, 5-a]pyridin-2-yl)amino]ethanaminium, methosulphate

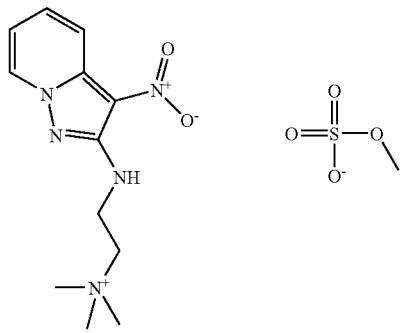

N,N,N-trimethyl-2-[(3-nitropyrazolo[1,5-a]pyridin-2-yl)amino]
ethanaminium, methosulphate 35 g (0.140 mol) of N-N-dimethyl-N'(3-nitro-pyrazolo[1, 5-a]pyridin-2-yl)-ethane-1,2-diamine was put in a 500-ml three-necked flask that was equipped with a bulb condenser, a thermometer and a 50-ml dropping funnel, and contained 200 ml of THF, while stirring with a magnetic stirrer. The mixture was heated in an oil bath to 50° C. and dimethylsulphate was dropwise added, resulting in the formation of a yellow precipitate. The reaction was monitored by TLC (eluent: dichloromethane/methanol 98:2), until the starting product disappeared. The solid that formed was drained and then washed several times with THF. The solid was then dried under vacuum in the presence of $P_2O_5$. 50.8 g of yellow powder was recovered.

NMR analyses ($^1$H 400 MHz and $^{13}$C 100.61 MHz DMSO $d_6$) were consistent with the expected structure.

The expected cation, $C_{12}H_{14}N_5O_2+$, was mainly detected at m/z=264 in ES+.

Stage 5

Synthesis of [2-(3-amino-pyrazolo[1,5-a]pyridin-2-ylamino)ethyl]-trimethyl-ammonium

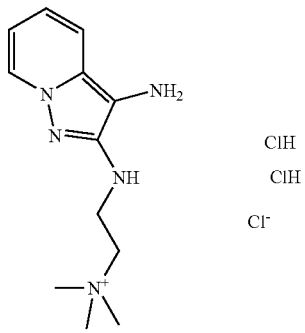

Dichlorhydrate de chlorure de [2-(3-Amino-pyrazolo[1,5-a]
pyridin-2-ylamino)-ethyl]-trimethyl-ammonium 120 g of zinc and 2.2 liters of ethanol were put a 4-liter round-bottomed flask equipped with a condenser, a thermometer and a mechanical stirrer.

At 40° C., 17 g of ammonium chloride solution and 220 ml of water were added and the resultant mixture was brought to to reflux. The reflux was self-maintained by adding 30 g of N,N,N-trimethyl-2-[(3-nitropyrazoio[1,5-a]pyridin-2-yl) amino]ethanaminium, methosulphate using a solid-feed funnel.

To ensure that the reaction went to completion, 5 ml of acetic acid was added.

At the end of reduction, zinc was removed by filtration on Celite, the combined liquors were washed with ethanol and acidified by adding hydrochloric isopropanol that was previously cooled in a bath of dry ice. Precipitation of a blue solid was then observed.

The solid was drained on a No. 3 frit and dried under vacuum in the presence of $P_2O_5$. 35.9 g of a yellow powder corresponding to the expected compound was recovered.

The quasi-molecular ions (MH)$^+$, (MNa)$^+$ and (M–H)$^-$ of the expected molecule, $C_9H_{12}N_4O$, were mainly detected.

NMR analyses ($^1$H 400 MHz and $^{13}$C 100.61 MHz DMSO $d_6$) were consistent with the expected structure.

Example 2

Stage 1

Synthesis of 2-imidazol-1-yl-3-nitro-pyrazolo[1,5-a]pyridine

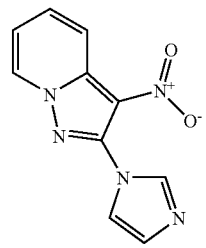

2-Imidazol-1-yl-3-nitro-pyrazolo[1,5-a]pyridine 5 g of 2-methanesulphanyl-3-nitro-pyrazolo[1,5-a]pyridine, 20 ml of N-methylpyrrolidinone and 7 g of imidazole were loaded, successively in a 100-ml three-necked flask equipped with a magnetic stirrer, a thermometer and a condenser.

This reaction mixture was heated at 100° C. for 30 minutes and then cooled, whereby the 2-imidazol-1-yl-3-nitro-pyrazolo[1,5-a]pyridine was precipitated in 5 volumes of water.

The precipitate was drained and dried under vacuum in the presence of phosphorus pentoxide. 4.23 g of a yellow solid was recovered.

NMR analyses ($^1$H 400 MHz and $^{13}$C 100.61 MHz DMSO $d_6$) were consistent with the expected structure.

The mass of the expected compound $C_{10}H_7N_5O_2$ was determined by mass spectrometry.

Stage 2

Synthesis of 1-methyl-3-(3-nitro-pyrazolo[1,5-a]pyridin-2-yl)-3H-imidazol-1-ium methosulphate

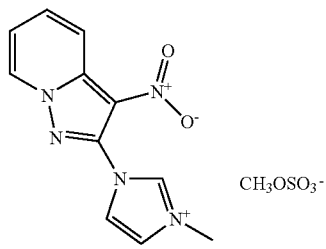

1-Methyl-3-(3-nitro-pyrazolo[1,5-a]pyridin-2-yl)-3H-imidazol-1-ium methosulphate 2.11 g of 2-imidazol-1-yl-3-nitro-pyrazolo[1,5-a]pyridine and 55 ml of THF were loaded, successively in a 100-ml three-necked flask equipped with a magnetic stirrer, a thermometer, a condenser and a dropping funnel.

To homogenize this reaction mixture, the mixture was heated at a temperature of 60° C., and then 2 ml of dimethylsulphate was added dropwise in 1 hour.

The solid that formed was drained on a No. 4 frit and then dried under vacuum in the presence of phosphorus pentoxide. After drying, a mass of 3 g of yellow powder was recovered.

NMR analyses ($^1$H 400 MHz and $^{13}$C 100.61 MHz DMSO $d_6$) were consistent with the expected structure.

The expected cation, $C_{11}H_{10}N_5O_2+$, was mainly detected at m/z=244 in ES+.

Stage 3

Synthesis of 3-(3-Amino-pyrazolo[1,5-a]pyridin-2-yl)-1-methyl-3H-imidazol-1-ium chloride dihydrochloride

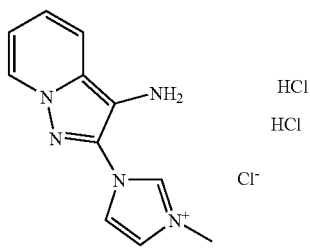

3-(3-Amino-pyrazolo[1,5-a]pyridin-2-yl)-1-methyl-3H-imidazol-1-ium chloride dihydrochloride 200 ml of water and 20 ml of conc. hydrochloric acid were loaded, successively in a 500-ml three-necked flask equipped with a magnetic stirrer, a thermometer and a condenser, and the mixture was heated to 60° C. Using a solid-feed funnel, a mixture of 5 g of zinc and 3 g of 2-imidazol-1-yl-3-nitro-pyrazolo[1,5-a]pyridine was added in 2 hours.

At the end of addition, reflux was maintained for 30 minutes and zinc was removed by filtration on a bed of Celite. The liquor was acidified with hydrochloric isopropanol.

The liquor was concentrated to one third and the solid was precipitated by means of isopropyl ether.

The solid that formed was drained on a No. 4 frit and then dried under vacuum in the presence of phosphorus pentoxide. After drying, a mass of 2.8 g was recovered.

The expected cation, $C_{11}H_{12}N_5+$, was mainly detected at m/z=214 in ES+.

NMR analyses ($^1$H 400 MHz and $^{13}$C 100.61 MHz DMSO $d_6$) were consistent with the expected structure.

Example 3

Synthesis of 3-nitro-N-(2-piperidin-1-ylethyl)pyrazolo[1,5-a]pyridin-2-amine

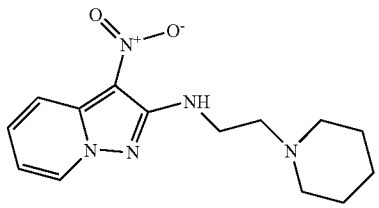

100 ml of NMP, 20 g (0.0711 mol) 2-methanesulphanyl-3-nitro-pyrazolo[1,5-a]pyridine and 20.3 ml (0.142 mol) of 2-piperidin-1-ylethanamine were put in a 250-ml three-necked flask equipped with a bulb condenser, a thermometer and a magnetic stirrer. While stirring, the mixture was heated to 70° C. on an oil bath for 4 hours, and was monitored by TLC (eluent: 95:5 dichloromethane/methanol).

The reaction mixture was cooled to room temperature and poured onto 400 g of an ice-water mixture. A beige compound was drained and crystallized on a No. 4 frit and then washed several times with water. The compound was dried at 35° C. under vacuum in the presence of $P_2O_5$. 20.43 g of a yellow solid corresponding to the expected compound was recovered.

NMR analyses ($^1$H 400 MHz and $^{13}$C 100.61 MHz DMSO $d_6$) were consistent with the expected structure.

$^1$H-NMR (DMSO-$d_6$): ☐ 1.4 (m, 2H), 1.51 (m, 4H), 2.45 (m, 4H), 2.56 (t, 2H), 3.47 (q, 2H), 7.26 (m, 1H), 7.32 (t, 1H), 7.76 (m, 1H), 8.04 (m, 2H), 8.75 (m, 1H).

The mass of the expected compound $C_{14}H_{19}N_5O_2$ was detected in mass spectrometry.

The quasi-molecular ions [M+H]$^+$, [M+Na]$^+$, [M+Na+CH$_3$OH]$^+$ of the expected molecule $C_{14}H_{19}N_5O_2$ were mainly detected.

Synthesis of 1-methyl-1-{2-[(3-nitropyrazolo[1,5-a]pyridin-2-yl)amino]ethyl}piperidinium methylsulphate

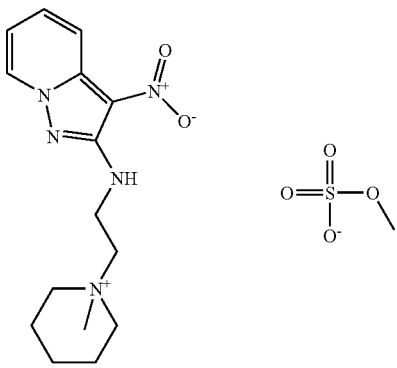

120 of THF, 17 g (0.05875 mol) of 3-nitro-N-(2-piperidin-1-ylethyl)pyrazolo[1,5-a]pyridin-2-amine and 11.12 ml (0.1175 mol) of dimethylsulphate were put in a 250-ml round-bottomed flask equipped with a bubbler and a magnetic stirrer, and the mixture was stirred for 24 hours at room temperature.

The insoluble product that formed was drained on a No. 3 frit and then washed with 3×100 ml of isopropyl ether under argon. The product was then dried at 35° C. under vacuum in the presence of $P_2O_5$.

23.84 g of a yellow solid corresponding to the expected compound was recovered.

NMR analyses ($^1$H 400 MHz and $^{13}$C 100.61 MHz DMSO $d_6$) were consistent with the expected structure.

The expected cation $[C_{15}H_{22}N_5O_2]^+$ was mainly detected at m/z, ESP+=304.

Synthesis of 1-{2-[(3-aminopyrazolo[1,5-a]pyridin-2-yl)amino]ethyl}-1-methylpiperidinium chloride dihydrochloride

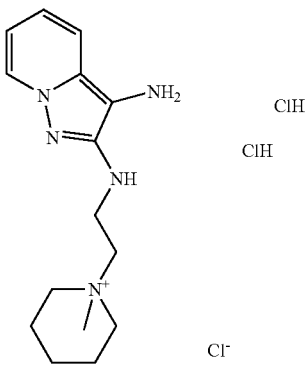

300 ml of ethanol and 10 g of zinc powder was put in a 500-ml three-necked flask equipped with a bulb condenser, a thermometer and a magnetic stirrer, and brought to reflux.

0.5 ml of acetic acid was then added dropwise, after which a solution comprising 20 ml of ethanol, 8 ml of water, 5 ml of acetic acid and 10 g of 1-methyl-1-{2-[(3-nitropyrazolo[1,5-a]pyridin-2-yl)amino]ethyl}piperidinium methylsulphate was added in 15 minutes, and reflux was maintained for 20 minutes.

At the end of reduction, zinc was removed by filtration under argon on a bed of Celite and the liquor was collected in a flask containing 100 ml of hydrochloric isopropanol, and washed with ethanol. The combined liquors were acidified with previously cooled 6N hydrochloric isopropanol.

Precipitation of a blue solid was then observed. The precipitate was drained on a No. 3 frit and washed with 2×15 ml of ethanol and 2×50 ml of isopropyl ether. The precipitate was then dried under vacuum in the presence of $P_2O_5$ and soda tablets. 9.1 g of a blue powder corresponding to the expected compound was obtained.

The expected cation $[C_{15}H_{24}N_5]^+$ as well as the fragment ions $[C_{14}H_{21}N_5]^+$, $[C_9H_{11}N_4]^+$, $[C_6H_{14}N]^+$ (detected respectively at m/z,ESP+=274, 259, 175, 100) and the adduct $[M+2Cl]^-$ were mainly detected.

NMR analyses ($^1$H 400 MHz and $^{13}$C 100.61 MHz DMSO $d_6$) were consistent with the expected structure.

Example 4

Synthesis of 3-nitro-N-(2-pyrrolidin-1-ylethyl)pyrazolo[1,5-a]pyridin-2-amine

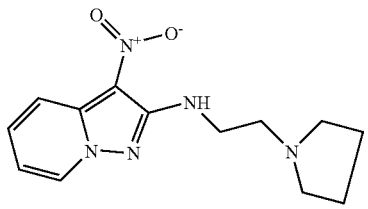

20 ml of NMP,15 g (0.062 mol) 2-methanesulphanyl-3-nitro-pyrazolo[1,5-a]pyridine and 16 ml of 2,3-aminoethylpyrrolidine were put in a 100-ml three-necked flask equipped with a bulb condenser, a thermometer and a magnetic stirrer. While stirring, the mixture was heated to 80° C. on an oil bath for 1 hour, and monitored by TLC (eluent: 90:5 ethyl acetate/methanol).

The reaction mixture was cooled to room temperature and then poured onto 400 g of an ice-water mixture. A yellowish beige precipitate formed, and was drained on a No. 4 frit and then washed several times with water. The precipitate was then dried at 35° C. under vacuum in the presence of $P_2O_5$. 15.2 g of a yellow solid corresponding to the expected compound was recovered.

NMR analyses ($^1$H 400 MHz and $^{13}$C 100.61 MHz DMSO $d_6$) and mass spectrometry were consistent with the expected structure.

Synthesis of 1-methyl-1-{2-[(3-nitropyrazolo[1,5-a]pyridin-2-yl)amino]ethyl}pyrrolidinium methylsulphate

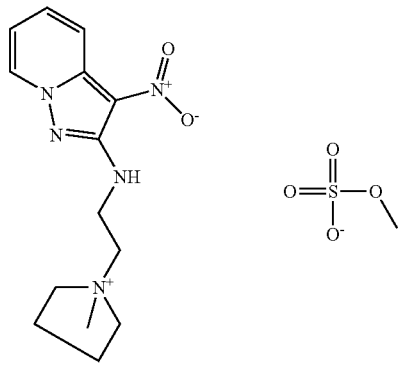

100 ml of THF, 10 g (0.0363 mol) of 3-nitro-N-(2-pyrrolidin-1-ylethyl)pyrazolo[1,5-a]pyridin-2-amine and 6.7 ml (0.0726 mol) of dimethyisuiphate were put in a 250-ml round-bottomed flask equipped with a bubbler and a magnetic stirrer, and brought to reflux while stirring for 2 hours.

The insoluble product that formed after cooling to room temperature was drained on a No. 3 frit and then washed with 3×20 of THF then 3×100 ml of petroleum ether under argon, and dried under vacuum in the presence of $P_2O_5$.

13.1 g of a yellow solid corresponding to the expected compound was recovered.

NMR analyses ($^1$H 400 MHz and $^{13}$C 100.61 MHz DMSO $d_6$) and mass spectrometry were consistent with the expected structure.

Synthesis of 1-{2-[(3-aminopyrazolo[1,5-a]pyridin-2-yl)amino]ethyl}-1-methylpyrrolidinium chloride hydrochloride

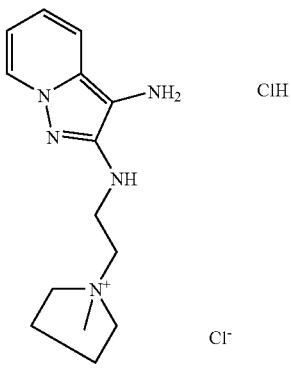

250 ml of ethanol and 10 g of zinc powder were put in a 500-ml three-necked flask equipped with a bulb condenser, a thermometer and a magnetic stirrer, and brought to reflux.

2 ml of acetic acid and then a solution of 5 ml water and 5 g of 1-methyl-1-{2-[(3-nitropyrazolo[1,5-a]pyridin-2-yl) amino]ethyl}pyrrolidinium methylsulphate were added dropwise.

At the end of discharge, 1 ml of acetic acid was added dropwise and reflux was maintained for 2 hours.

At the end of reduction, zinc was removed by filtration under argon on a bed of Celite and the liquor was collected in a flask containing 50 ml of previously cooled 6N hydrochloric isopropanol.

Precipitation of a grey-blue solid was observed. This precipitate was drained on a No. 3 frit and then washed with 2×15 ml of ethanol and 2×50 ml of isopropyl ether. The precipitate was then dried under vacuum in the presence of $P_2O_5$ and soda tablets. 4 g of a grey-blue powder corresponding to the expected compound was recovered.

NMR analyses ($^1$H 400 MHz and $^{13}$C 100.61 MHz DMSO $d_6$) were consistent with the expected structure.

The expected cation $[C_{14}H_{22}N_5]^+$ was mainly detected at m/z,ESP+=260.

Example 5

Synthesis of N-(2-morpholin-4-ylethyl)-3-nitropyrazolo[1,5-a]pyridin-2-amine

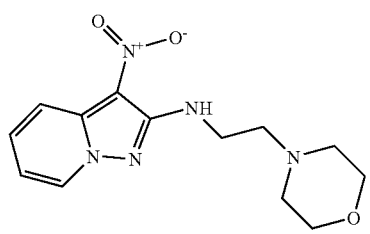

15 ml of NMP, 10 g (0.0415 mol) of 2-methanesulphanyl-3-nitro-pyrazolo[1,5-a]pyridine and 11 ml of 2-aminoethyl-morpholine was put in a 100-ml three-necked flask equipped with a bulb condenser, a thermometer and a magnetic stirrer. While stirring, the mixture was heated to 80° C. on an oil bath for 1 hour, and monitored by TLC (eluent: 90:5 ethyl acetate/methanol).

The reaction mixture was cooled to room temperature and poured onto 400 g of an ice-water mixture. The yellowish beige precipitate that formed was drained on a No. 4 frit and then washed several times with water. The precipitate was then dried at 35° C. under vacuum in the presence of $P_2O_5$. 10.4 g of a yellow solid corresponding to the expected compound was recovered.

NMR analyses ($^1$H 400 MHz and $^{13}$C 100.61 MHz DMSO $d_6$) and mass spectrometry were consistent with the expected structure.

Synthesis of 4-methyl-4-{2-[(3-nitropyrazolo[1,5-a]pyridin-2-yl)amino]ethyl}morpholin-4-ium methylsulphate

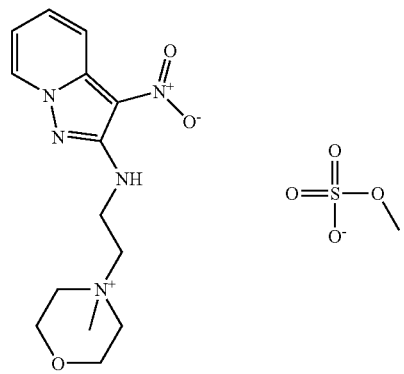

100 ml of THF, 10 g (0.03433 mol) of N-(2-morpholin-4-yl-ethyl)-3-nitropyrazolo[1,5-a]pyridin-2-amine and 6.7 ml (0.0726 mol) of dimethylsulphate were put in a 250-ml round-bottomed flask equipped with a bubbler and a magnetic stirrer, and the mixture was stirred and refluxed for 2 hours.

The insoluble product that formed after cooling to room temperature was drained on a No. 3 frit and then washed with 3×20 ml of THF and then 3×100 ml of petroleum ether under argon, and was dried under vacuum in the presence of $P_2O_5$.

13.9 g of a yellow solid corresponding to the expected compound was recovered.

NMR analyses ($^1$H 400 MHz and $^{13}$C 100.61 MHz DMSO $d_6$) and mass spectrometry were consistent with the expected structure.

Synthesis of 4-{2-[(3-aminopyrazolo[1,5-a]pyridin-2-yl)amino]ethyl}-4-methylmorpholin-4-ium chloride hydrochloride

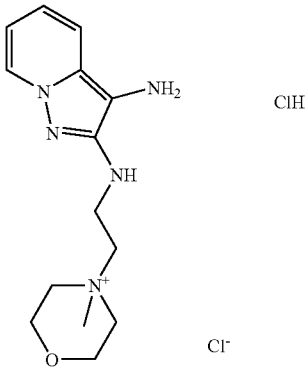

250 ml of ethanol and 10 g of zinc powder were put in a 500-ml three-necked flask equipped with a bulb condenser, a thermometer and a magnetic stirrer, and brought to reflux.

2 ml of acetic acid, and a solution of 5 ml of water and 5 g of 1-methyl-1-{2-[(3-nitropyrazolo[1,5-a]pyridin-2-yl)amino]ethyl}pyrrolidinium methylsulphate were then added dropwise.

At the end of discharge, 1 ml of acetic acid was then added dropwise, and reflux was maintained for 1.5 hours.

At the end of reduction, zinc was removed by filtration under argon on a bed of Celite and the liquor was collected in a flask containing 50 ml of previously cooled 6N hydrochloric isopropanol.

Precipitation of a solid was observed. This solid was drained on a No. 3 frit and then washed with 2×15 ml of ethanol and 2×50 ml of isopropyl ether. The solid was then dried under vacuum in the presence of $P_2O_5$ and soda tablets. 3.8 g of a grey-blue powder corresponding to the expected compound was recovered.

NMR analyses ($^1$H 400 MHz and $^{13}$C 100.61 MHz DMSO $d_6$) were consistent with the expected structure.

The expected cation $[C_{14}H_{22}N_5O]^+$ was mainly detected.

Example 6

Synthesis of N,N-diisopropyl-N'-(3-nitropyrazolo[1,5-a]pyridin-2-yl)ethane-1,2-diamine

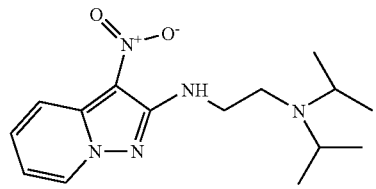

20 ml of NMP, 10 g (0.0414 mol) 2-methanesulphanyl-3-nitro-pyrazolo[1,5-a]pyridine and 14.4 ml (0.082 mol) of N,N-diisopropylethane-1,2-diamine were put in a 100-ml three-necked flask equipped with a bulb condenser, a thermometer and a magnetic stirrer. While stirring, the mixture was heated to 70° C. on an oil bath for 1 hour, and monitored by TLC (eluent: 95:5 dichloromethane/methanol).

The reaction mixture was cooled to room temperature and poured onto a mixture of 100 g of ice and water. The yellow precipitate that forms was drained on a No. 3 frit and then washed with water and then with 3×100 ml of petroleum ether. The precipitate was then dried at 35° C. under vacuum in the presence of $P_2O_5$. 11.88 g of a yellow solid corresponding to the expected compound was recovered.

NMR analyses ($^1$H 400 MHz and $^{13}$C 100.61 MHz DMSO $d_6$) were consistent with the expected structure.

The quasi-molecular ions $[M+H]^+$, $[M+Na]^+$, $[M+Na+CH_3OH]^+$ of the expected molecule $C_{15}H_{23}N_5O_2$ were mainly detected.

Synthesis of N-isopropyl-N-methyl-N-{2-[(3-nitropyrazolo[1,5-a]pyridin-2-yl)amino]ethyl}propan-2-aminium methylsulphate

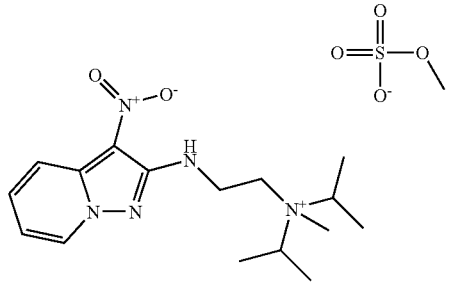

45 ml of THF, 6.4 g (0.02095 mol) of N-diisopropyl-N'-(3-nitropyrazolo[1,5-a]pyridin-2-yl)ethane-1,2-diamine and 3.96 ml (0.04191 mol) of dimethylsulphate was put in a 10-ml round-bottomed flask equipped with a bubbler and a magnetic stirrer, and the mixture was stirred at 65° C. for 5 hours.

The insoluble product that formed was drained at room temperature on a No. 3 frit and then washed with 15 ml of THF and then 3×25 ml of dichloromethane THF and 3×15 ml of isopropyl ether under argon. The product was then dried at 35° C. under vacuum in the presence of $P_2O_5$.

4.85 g of a yellow solid corresponding to the expected compound was recovered.

NMR analyses ($^1$H 400 MHz and $^{13}$C 100.61 MHz DMSO $d_6$) and mass spectrometry were consistent with the expected structure.

Synthesis of N-{2-[(3-aminopyrazolo[1,5-a]pyridin-2-yl)amino]ethyl}-N-isopropyl-N-methylpropan-2-aminium chloride dihydrochloride

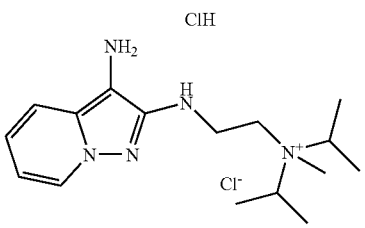

150 ml of ethanol and 3 g of zinc powder were put in a 250-ml three-necked flask equipped with a bulb condenser, a thermometer and a magnetic stirrer, brought to reflux, and 0.2 ml of acetic acid was added dropwise.

A solution containing 8 ml of ethanol, 4 ml of water, 3 ml of acetic acid and 3 g of N,N-diethyl-N-methyl-2-[(3-nitropyrazolo[1,5-a]pyridin-2-yl)amino]ethanaminium methylsulphate was then added in 15 minutes, and reflux was maintained for 15 minutes.

At the end of reduction, zinc was removed by filtration under argon on a bed of Celite and the liquor was collected in a flask containing 25 ml of previously cooled 6N hydrochloric isopropanol.

The liquor was then concentrated down to 40 ml and a grey-blue solid started to crystallize.

This solid was drained on a No. 3 frit, washed with 2×60 ml of isopropyl ether and dried under vacuum in the presence of $P_2O_5$. 3.27 of a grey-blue solid corresponding to the expected compound was recovered.

NMR analyses ($^1H$ 400 MHz and $^{13}C$ 100.61 MHz DMSO $d_6$) and mass spectrometry were consistent with the expected structure.

Example 7

Synthesis of N,N-diethyl-N'-(3-nitropyrazolo[1,5-a]pyridin-2-yl)ethane-1,2-diamine

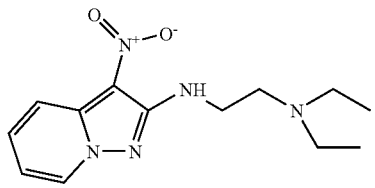

100 ml of NMP, 10 g (0.0414 mol) 2-methanesulphanyl-3-nitro-pyrazolo[1,5-a]pyridine and 11.65 ml (0.0829 mol) of N,N-diethylenediamine were put in a 100-ml three-necked flask equipped with a bulb condenser, a thermometer and a magnetic stirrer. While stirring, the mixture was heated to 70° C. on an oil bath for 4 hours, and monitored by TLC (eluent: 95:5 dichloromethane/methanol).

The reaction mixture was cooled to room temperature and poured onto a mixture of 100 g of ice and water. The yellow compound which crystallizes was drained on a No. 3 frit and then washed with 3×100 ml of petroleum ether. The compound was then dried at 35° C. under vacuum in the presence of $P_2O_5$. 9.80 g of a yellow solid corresponding to the expected compound was recovered.

NMR analyses ($^1H$ 400 MHz and $^{13}C$ 100.61 MHz DMSO $d_6$) were consistent with the expected structure.

The quasi-molecular ions $[M+H]^+$, $[M+Na]^+$, $[M+Na+CH_3OH]^+$ of the expected molecule $C_{13}H_{19}N_5O_2$ were mainly detected.

Synthesis of N,N-diethyl-N-methyl-2-[(3-nitropyrazolo[1,5-a]pyridin-2-yl)amino]ethanaminium methylsulphate

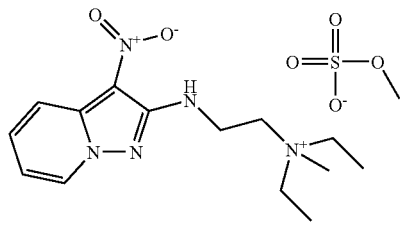

20 ml of THF, 4 g (0.01658 mol) of N,N-diethyl-N'-(3-nitropyrazolo[1,5-a]pyridin-2-yl)ethane-1,2-diamine and 3.13 ml (0.03316 mol) of dimethylsulphate were put in a 50-ml single-necked flask equipped with a bubbler and a magnetic stirrer, and the mixture was stirred for 24 hours at room temperature.

The insoluble product that formed was drained on a No. 3 frit and then washed with 3×15 ml of THF and 3×15 ml of isopropyl ether under argon. The product was then dryied at 35° C. under vacuum in the presence of $P_2O_5$.

5.48 g of a yellow solid corresponding to the expected compound was recovered.

NMR analyses ($^1H$ 400 MHz and $^{13}C$ 100.61 MHz DMSO $d_6$) were consistent with the expected structure.

The expected cation $[C_{14}H_{22}N_5O_2]^+$ was mainly detected at m/z,ESP+=292.

Synthesis of 2-[(3-aminopyrazolo[1,5-a]pyridin-2-yl)amino]-N,N-diethyl-N-methylethanaminium chloride hydrochloride

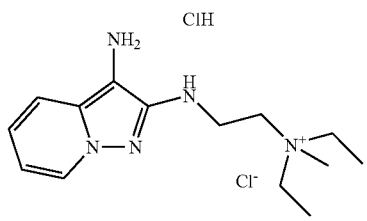

150 ml of ethanol and 3 g of zinc powder were put in a 250-ml three-necked flask equipped with a bulb condenser, a thermometer and a magnetic stirrer, and brought to reflux.

0.5 ml of acetic acid was then added dropwise. A solution comprising 10 ml of ethanol, 2 ml of water, 3 ml of acetic acid and 3 g N-isopropyl-N-methyl-N-{2-[(3-nitropyrazolo[1,5-a]pyridin-2-yl)amino]ethyl}propan-2-aminium methylsulphate was then added in 15 minutes, and reflux was maintained for 15 minutes.

At the end of reduction, zinc was removed by filtration under argon on a bed of Celite and the liquor was recovered in a flask containing 25 ml of previously cooled 6N hydrochloric isopropanol.

Then the liquor was concentrated until a milky solution was obtained and crystallization began.

The solid that formed was drained on a No. 3 frit, and washed with of 3×40 ml of isopropyl ether. The solid was then dried under vacuum in the presence of $P_2O_5$ and soda tablets.

2.25 g of a blue-green solid corresponding to the expected compound was recovered.

NMR analyses ($^1H$ 400 MHz and $^{13}C$ 100.61 MHz DMSO $d_6$) and mass spectrometry were consistent with the expected structure.

Example 8

Synthesis of 3-nitro-N-(2-pyridin-3-ylethyl)pyrazolo[1,5-a]pyridin-2-amine

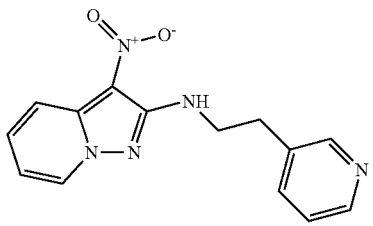

10 ml of NMP, 4.93 g (0.02046 mol) 2-methanesulphanyl-3-nitro-pyrazolo[1,5-a]pyridine and 5 g ml (0.04092 mol) of 3-(2-aminoethyl)-pyridine were put in a 100-ml three-necked flask equipped with a bulb condenser, a thermometer and a magnetic stirrer. While stirring, the mixture was heated to 70° C. on an oil bath for 1 hour, and monitored by TLC (eluent: 95:5 dichloromethane/methanol).

The reaction mixture was cooled to room temperature and then poured onto a mixture of 100 g of ice and water. The yellow compound which crystallized was drained on a No. 3 frit, washed with water and then with 3×100 ml of petroleum ether. The compound was then dried at 35° C. under vacuum in the presence of $P_2O_5$. 5.61 g of a yellow solid corresponding to the expected compound was recovered.

NMR analyses ($^1$H 400 MHz and $^{13}$C 100.61 MHz DMSO $d_6$) were consistent with the expected structure.

The quasi-molecular ions $[M+H]^+$, $[M+Na]^+$, $[M+Na+CH_3OH]^+$, $[2M+H]^+$, $[2M+Na]^+$ of the expected molecule $C_{14}H_{13}N_5O_2$ were mainly detected.

Synthesis of 1-methyl-3-{2-[(3-nitropyrazolo[1,5-a]pyridin-2-yl)amino]ethyl}pyridinium methylsulphate

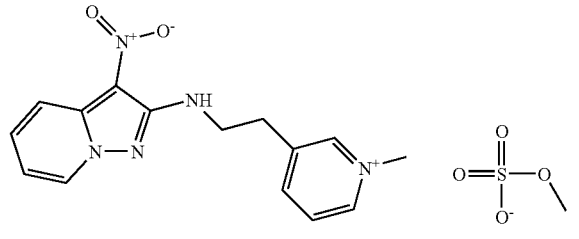

50 ml of THF, 3 g ( 0.01058 mol) of 3-nitro-N-(2-pyridin-3-ylethyl)pyrazolo[1,5-a]pyridin-2-amine and 2 ml (0.02117 mol) of dimethylsulphate was put in a 50-ml round-bottomed flask equipped with a bubbler and a magnetic stirrer. The mixture was stirred for 18 hours at room temperature.

The insoluble product that formed was drained on a No. 3 frit and then washed with 3×15 ml of THF and 3×15 ml of isopropyl ether under argon, and then dried at 35° C. under vacuum in the presence of $P_2O_5$.

4.07 g of a yellow solid corresponding to the expected compound was recovered.

NMR analyses ($^1$H 400 MHz and $^{13}$C 100.61 MHz DMSO $d_6$) were consistent with the expected structure. The expected cation $[C_{15}H_{16}N_5O_2]^+$ is mainly detected at m/z,ESP+=298

Synthesis of 3-{2-[(3-aminopyrazolo[1,5-a]pyridin-2-yl)amino]ethyl}-1-methylpyridinium chloride hydrochloride

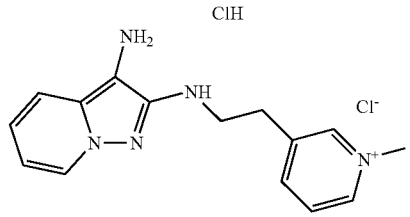

150 ml of ethanol and 3 g of zinc powder was put in a 250-ml three-necked flask equipped with a bulb condenser, a thermometer and a magnetic stirrer, and brought to reflux.

0.2 ml of acetic acid was then added dropewise. A solution comprising 8 ml of ethanol, 4 ml of water, 2 ml of acetic acid and 3 g of 1-methyl-3-{2-[(3-nitropyrazolo[1,5-a]pyridin-2-yl)amino]ethyl}pyridinium methylsulphate was then added in 15 minutes, and reflux was maintained for 15 minutes.

At the end of reduction, the zinc was removed by filtration under argon on a bed of Celite and the liquor was recovered in a flask containing 25 ml of previously cooled 6N hydrochloric isopropanol.

Then the liquor was concentrated until crystallization began, and then cooled to zero degrees.

The solid that formed was drained on a No. 3 frit, wash with of 3×40 ml of isopropyl ether and dried under vacuum in the presence of $P_2O_5$ and soda tablets. 3.39 g of a green solid corresponding to the expected compound was recovered.

NMR analyses ($^1$H 400 MHz and $^{13}$C 100.61 MHz DMSO $d_6$) and mass spectrometry were consistent with the expected structure.

Example 9

Synthesis of 3-nitro-N-(2-pyridin-4-ylethyl)pyrazolo[1,5-a]pyridin-2-amine

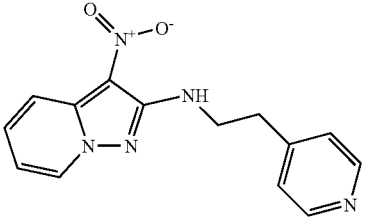

50 ml of NMP, 10 g (0.03555 mol) 2-methanesulphanyl-3-nitro-pyrazolo[1,5-a]pyridine and 8.68 g (0.07110 mol) of 4-(2-aminoethyl) were put in a 100-ml three-necked flask equipped with a bulb condenser, a thermometer and a magnetic stirrer. While stirring, the mixture was heated to 70° C. on an oil bath for 4 hours, and monitored by TLC (eluent: 95:5 dichloromethane/methanol).

The reaction mixture was cooled to room temperature and poured onto 200 g of an ice-water mixture. The yellow compound that crystallized was drained on a No. 3 frit, washed with water and then with 3×100 ml of petroleum ether, and dried at 35° C. under vacuum in the presence of $P_2O_5$ for 12 hours. 10.81 g (product not completely dry) of a yellow solid corresponding to the expected compound was recovered.

NMR analyses ($^1$H 400 MHz and $^{13}$C 100.61 MHz DMSO $d_6$) and mass spectrometry were consistent with the expected structure.

Synthesis of 1-methyl-4-{2-[(3-nitropyrazolo[1,5-a]pyridin-2-yl)amino]ethyl}pyridinium methylsulphate

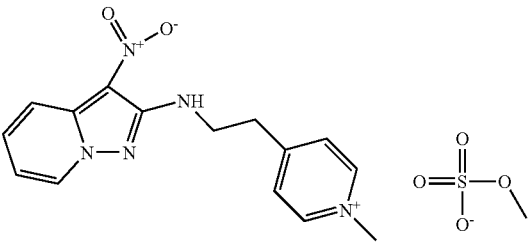

50 ml of THF and 8 g (0.01058 mol) of 3-nitro-N-(2-pyridin-4-ylethyl)pyrazolo[1,5-a]pyridin-2-amine and 5.34 ml (0.05648 mol) of dimethylsulphate were put in a 100-ml round-bottomed flask equipped with a bubbler and a magnetic stirrer, and the mixture was stirred for 24 hours at room temperature.

The insoluble product that formed was drained on a No. 3 frit and then washed with 3×50 ml of THF and 3×50 ml of isopropyl ether under argon and dried at 35° C. under vacuum in the presence of $P_2O_5$.

11.06 g of a yellow solid corresponding to the expected compound was recovered.

NMR analyses ($^1$H 400 MHz and $^{13}$C 100.61 MHz DMSO $d_6$) and mass spectrometry were consistent with the expected structure.

Synthesis of 3-{2-[(3-aminopyrazolo[1,5-a]pyridin-2-yl)amino]ethyl}-1-methylpyridinium chloride hydrochloride

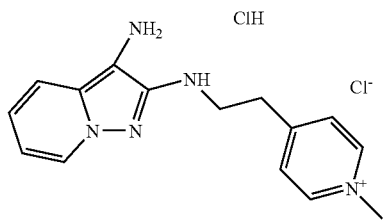

150 ml of ethanol and 3 g of zinc powder were put in a 250-ml three-necked flask equipped with a bulb condenser, a thermometer and a magnetic stirrer, and brought to reflux.

0.2 ml of acetic acid was then added dropwise. A solution comprising 8 ml of ethanol, 3 ml of water, 2 ml of acetic acid and 3 g 1-methyl-4-{2-[(3-nitropyrazolo[1,5-a]pyridin-2-yl)amino]ethyl}pyridinium methylsulphate was then added in 15 minutes, and reflux was maintained for 15 minutes.

At the end of reduction, the zinc was removed by filtration under argon on a bed of Celite and the liquor was recovered in a flask containing 25 ml of previously ice-cooled 6N hydrochloric isopropanol.

The liquor was then concentrated until crystallization began, and then cooled to zero degrees.

The solid that formed was drained on a No. 3 frit, washed with 3×40 ml of isopropyl ether and dried under vacuum in the presence of $P_2O_5$ and soda tablets. 1.42 g of a green solid corresponding to the expected compound was recovered.

NMR analyses ($^1$H 400 MHz and $^{13}$C 100.61 MHz DMSO $d_6$) and mass spectrometry were consistent with the expected structure.

Example 10

The example was obtained on the basis of the following general scheme:

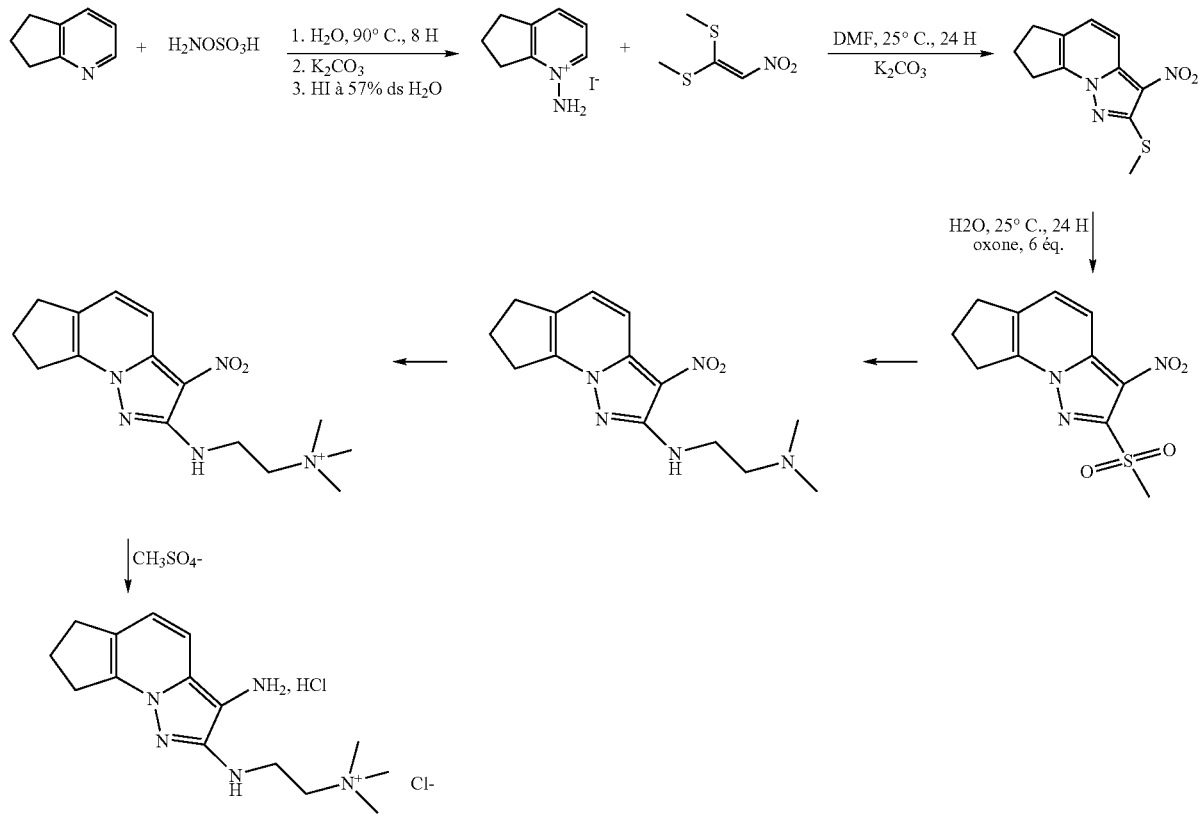

Synthesis of 1-amino-6,7-dihydro-5H-cyclopenta[b]pyridinium iodide

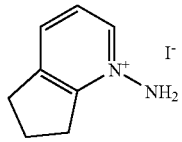

400 ml of water and 123 g (1.032 mol) 2,3-cyclopentenopyridine was put in a 1000-ml three-necked flask equipped with a bubbler, a thermometer and a mechanical stirrer. 46.6 g (0.413 mol) of hydroxylamine-o-sulphonic acid was then added in small portions, and the mixture was refluxed for 18 hours.

The reaction mixture was cooled to room temperature and 74.2 g (0.537 mol) of potassium carbonate was gently added. The resultant mixture was stirred for 30 minutes.

The aqueous phase was washed with 4×200 ml of ethyl acetate, and the aqueous phase was co-evaporated with 2-propanol to obtain a chestnut-brown solid, which was taken up in 400 ml of ethanol to remove the salts.

The brown ethanol solution was put in a 2-liter three-necked flask equipped with an isobaric funnel; while stirring, at −70° C. 67.5 ml (0.516 mol) of hydriodic acid was added dropwise.

At the end of discharge, the temperature was allowed to return to zero degrees and the insoluble beige product was drained on a No. 3 frit. This solid was washed with 3×150 ml of isopropyl ether and dried under vacuum in the presence of $P_2O_5$ for 12 hours. 27.7 g of a beige solid corresponding to the expected compound was recovered.

NMR analyses ($^1H$ 400 MHz and $^{13}C$ 100.61 MHz DMSO $d_6$) and mass spectrometry were consistent with the expected structure.

The expected cation $[C_8H_{11}N_2]^+$ was mainly detected at m/z,ESP+=135. Detection of $I^-$ ions in electrospray was negative.

Synthesis of 2-(methylsulphanyl)-3-nitro-7,8-dihydro-6H-cyclopenta[e]pyrazolo[1,5-a]pyridine

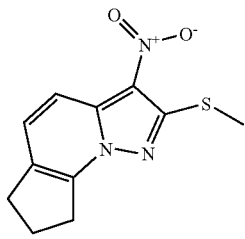

500 ml of NMP and 65.56 g (0.025 mol) of 1-amino-6,7-dihydro-5H-cyclopenta[b]pyridinium iodide were put in a 2-liter three-necked flask equipped with a bubbler, a condenser and a mechanical stirrer. While stirring, 103.65 g of potassium carbonate was then gently added in 15 minutes. 41.33 g (0.25 mol) of 1,1-bis(methythio)-2-nitroethylene was then added in one go.

Stirring was continued for 48 hours at room temperature, after which the liquor was poured onto 2.5 liters of an ice-water mixture.

The dark green insoluble product that formed was drained on a No. 3 frit and then washed with plenty of water, 3×200 ml of ethyl acetate and then 3×200 ml of isopropyl ether.

The precipitate was then dried under vacuum in the presence of $P_2O_5$. 36.77 g of a dark green solid corresponding to the expected compound was recovered.

NMR analyses ($^1H$ 400 MHz and $^{13}C$ 100.61 MHz DMSO $d_6$) and mass spectrometry were consistent with the expected structure.

The quasi-molecular ions $[M+H]^+$, $[M+Na]^+$, $[2M+Na]^+$ of the expected molecule $C_{11}H_{11}N_3O_2S$ were mainly detected.

Synthesis of 2-(methylsulphonyl)-3-nitro-7,8-dihydro-6H-cyclopenta[e]pyrazolo[1,5-a]pyridine

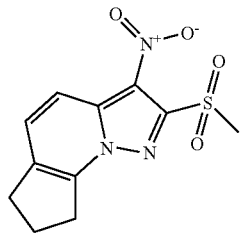

267.6 g of Oxone (3 eq.), 800 ml of water and 36.17 g of 2-(methylsulphanyl)-3-nitro-7,8-dihydro-6H-cyclopenta[e]pyrazolo[1,5-a]pyridine (0.145 mol) obtained previously were loaded successively in a 3-liter three-necked flask equipped with a mechanical stirrer and an internal temperature sensor. The mixture was stirred at room temperature.

Oxone (89.2 g, 1 eq.) was added to complete the reaciton, and the reaction ended after stirring for 4 hours at room temperature.

The solid that formed was drained and washed with plenty of water until a filtrate was obtained that no longer contained peroxides. The filtrate was then placed under vacuum at 40° C. over $P_2O_5$.

35.31 g of the expected product was obtained (yellow solid).

NMR analyses ($^1H$ 400 MHz and $^{13}C$ 100.61 MHz DMSO $d_6$) and mass spectrometry were consistent with the expected structure.

$^1H$-NMR (DMSO-$d_6$): 2.31 (m, 2H), 3.13(t,2H), 3.38 (t, 2H), 3.59 (s, 3H), 8.01 (d, 1H), 8.21 (d, 1H).

The quasi-molecular ions $[M-H]^-$, $[M+H]^+$, $[M+Na]^+$, $[M+NA+CH_3OH]^+$, $[2M+Na]^+$ of the expected molecule $C_{11}H_{11}N_3O_4S$ were mainly detected.

Synthesis of N,N-dimethyl-N'-(3-nitro-7,8-dihydro-6H-cyclopenta[e]pyrazolo[5-a]pyridin-2-yl)ethane-1,2-diamine

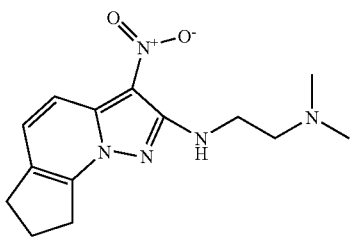

50 ml of NMP, 10 g (0.03555 mol) 2-(methylsulphonyl)-3-nitro-7,8-dihydro-6H-cyclopenta[e]pyrazolo[1,5-a]pyridine and 7.8 ml of N.N-dimethylethylene diamine were put in a 250-ml three-necked flask equipped with a bulb condenser, a thermometer and a magnetic stirrer. The mixture was heated to 70° C. on an oil bath for 4 hours, and monitored by TLC (eluent: 95:5 dichloromethane/methanol).

The reaction mixture was cooled to room temperature and then poured onto 200 g of an ice-water mixture. The yellow compound which crystallized was drained on a No. 3 frit, washed with water 2×100 ml and then with 3×100 ml of isopropyl ether. The compound was then dried at 35° C. under vacuum in the presence of $P_2O_5$ for 12 hours. 8.32 g of a green solid corresponding to the expected compound was recovered.

NMR analyses ($^1$H 400 MHz and $^{13}$C 100.61 MHz DMSO $d_6$) and mass spectrometry were consistent with the expected structure.

$^1$H-NMR (DMSO-$d_6$): 2.21 (m+s, 2H), 3.01 (t,2H), 3.20 (t, 2H), 3.48 (q, 2H), 7.27 (t, 1H), 7.66 (d, 1H), 7.83 (d, 1H).

The quasi-molecular ions of the expected molecule $C_{14}H_{19}N_5O_2$ were mainly detected.

Synthesis of N,N,N-trimethyl-2-r(3-nitro-7.8-dihydro-6H-cyclopenta[e]pyrazolo[1,5-a]pyridin-2-yl) amino]ethanaminium methylsulphate

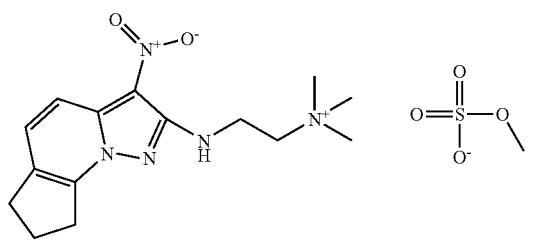

45 ml of THF, 6.3 g (0.02177 mol) of N,N-dimethyl-N'-(3-nitro-7,8-dihydro-6H-cyclopenta[e]pyrazolo[1,5-a]pyridin-2-yl)ethane-1,2-diamine and 4.12 ml (0.04354 mol) of dimethylsulphate were put in a 100-ml round-bottomed flask equipped with a bubbler and a magnetic stirrer. The mixture was stirred for 24 hours at room temperature.

The insoluble product that formed was drained on a No. 3 frit and then washed with 3×50 ml of THF and 3×50 ml of isopropyl ether under argon and dried at 35° C. under vacuum in the presence of $P_2O_5$.

8.73 g of a yellow solid corresponding to the expected compound was recovered.

NMR analyses ($^1$H 400 MHz and $^{13}$C 100.61 MHz DMSO $d_6$) and mass spectrometry were consistent with the expected structure.

The expected cation $[C_{15}H_{22}N_5O_2]^+$ was mainly detected. $CH_3OSO_3$— was also detected in negative electrospray.

Synthesis of 3-[(3-amino-7,8-dihydro-6H-cyclopenta [e]pyrazolo[1,5-a]pyridin-2-yl)amino]-N,N,N-trimethylpropan-1-aminium chloride hydrochloride

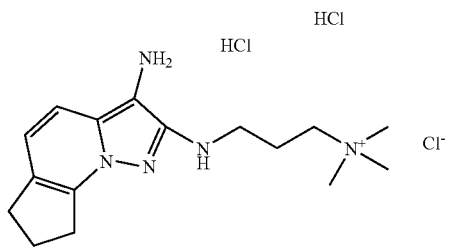

100 ml of ethanol and 2 g of zinc powder were put in a 250-ml three-necked flask equipped with a bulb condenser, a thermometer, a dropping funnel and a magnetic stirrer, and brought to reflux.

0.5 ml of acetic acid and then a solution comprising 8 ml of ethanol, 3 ml of water, 2 ml of acetic acid and 2 g of N,N,N-trimethyl-2-[(3-nitro-7,8-dihydro-6H-cyclopenta[e]pyrazolo[1,5-a]pyridin-2-yl)amino]ethanaminium methylsulphate were then added dropwise. Reflux was maintained for 90 minutes.

At the end of reduction, zinc was removed by filtration under argon on a bed of Celite and the filtrate was collected in a flask containing 25 ml of previously cooled 6N hydrochloric isopropanol.

The light blue solid that formed was drained on a No. 3 frit, washed with 2×60 ml of isopropyl ether and dried under vacuum in the presence of $P_2O_5$ and soda tablets. 2.64 g of blue-green solid corresponding to the expected compound was recovered.

NMR analyses ($^1$H 400 MHz and $^{13}$C 100.61 MHz DMSO $d_6$) and mass spectrometry were consistent with the expected structure.

Example 11

Synthesis of 2-[(3-amino-6,7-dimethylpyrazolo[1,5-a]pyridin-2-yl)amino]-N,N,N-trimethylethanaminium chloride dihydrochloride

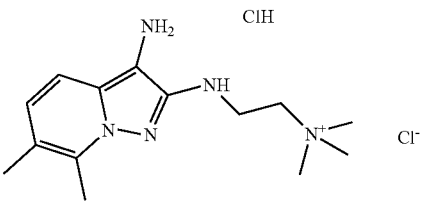

250 ml of ethanol and 10 g of zinc powder were put in a 500-ml three-necked flask equipped with a bulb condenser, a thermometer and a magnetic stirrer, and brought to reflux.

2 ml of acetic acid and then a solution comprising 5 ml of water and 5 g of 2-[(6,7-dimethyl-3-nitropyrazolo[1,5-a]pyridin-2-yl)amino]-N,N,N-trimethylethanaminium methylsulphate were then added dropwise.

At the end of discharge, 1 ml of acetic acid was added dropwise, and reflux was maintained for 1.5 hours.

At the end of reduction, zinc was removed by filtration under argon on a bed of Celite and the filtrate was collected in a flask containing 50 ml of previously cooled 6N hydrochloric isopropanol.

Precipitation of a solid was observed. This precipitate was drained on a No. 3 frit, washed with 2×15 ml of ethanol and 2×50 ml of isopropyl ether, and dried under vacuum in the presence of $P_2O_5$ and soda tablets. 3.8 g of a grey-blue powder corresponding to the expected compound was recovered.

NMR analyses ($^1$H 400 MHz and $^{13}$C 100.61 MHz DMSO $d_6$) were consistent with the expected structure.

The expected cation $[C_{14}H_{24}N_5]^+$ was detected at m/z, ESP+=262 and 131 (corresponding respectively to $[M]^+$ and $[M+H]^{2+}$).

Example 12

Synthesis of N-[3-(1H-imidazol-1-yl)propyl]-3-nitropyrazolo[1,5-a]pyridin-2-amine

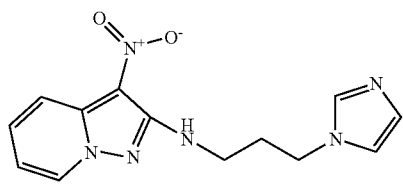

50 ml of NMP, 5 g (0.021 mol) of 2-methanesulphanyl-3-nitro-pyrazolo[1,5-a]pyridine and 26 g of 3-(1H-imidazol-1-yl)propan-1-amine were put in a 100-ml three-necked flask equipped with a bulb condenser, a thermometer and a magnetic stirrer, and stirred for 6 hours, monitored by TLC (eluent: 95:5 dichloromethane/methanol).

The reaction mixture was poured onto 200 g of an ice-water mixture. The yellow compound which crystallized was drained on a No. 3 frit, washed with water 2×100 ml and then 3×100 ml of isopropyl ether, and then dried at 35° C. under vacuum in the presence of $P_2O_5$ for 12 hours. 5 g of a green solid corresponding to the expected compound was recovered.

NMR analyses ($^1$H 400 MHz and $^{13}$C 100.61 MHz DMSO $d_6$) and mass spectrometry were consistent with the expected structure.

The quasi-molecular ions $[M+H]^+$, $[2M+H]^+$ of the expected molecule $C_{13}H_{14}N_6O_2$ were mainly detected.

Synthesis of 3-methyl-1-{3-[(3-nitropyrazolo[1,5-a]pyridin-2-yl)amino]propyl}-1H-imidazol-3-ium methylsulphate

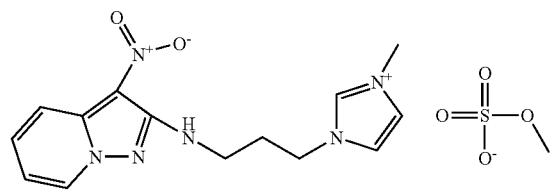

50 ml of THF and 2.7 g (0.0095 mol) of N-[3-(1H-imidazol-1-yl)propyl]-3-nitropyrazolo[1,5-a]pyridin-2-amine were put in a 100-ml three-necked flask equipped with a bulb condenser, a thermometer and a magnetic stirrer, and 1.8 ml (0.019 mol) of dimethylsulphate was added dropwise with reflux of the THF.

The reaction was monitored by TLC (eluent: 95:5 dichloromethane/methanol).

The reaction mixture was allowed to return to room temperature and the yellow solid that formed was drained on a No. 3 frit, washed with 2×100 ml of THF and then with 3×100 ml of isopropyl ether, and then dried at 35° C. under vacuum in the presence of $P_2O_5$ for 12 hours. 3.91 g of a yellow solid corresponding to the expected structure was recovered.

NMR analyses ($^1$H 400 MHz and $^{13}$C 100.61 MHz DMSO $d_6$) and mass spectrometry complied.

Synthesis of 1-{3-[(3-aminopyrazolo[1,5-a]pyridin-2-yl)amino]propyl}-3-methyl-1H-imidazol-3-ium chloride dihydrochloride

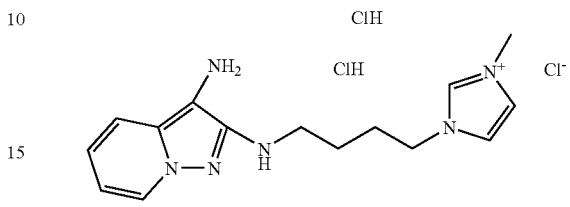

80 ml of propanol-2 and 6 g of zinc powder were put in a 250-ml three-necked flask equipped with a bulb condenser, a thermometer, a dropping funnel and a magnetic stirrer, and brought to reflux.

1 ml of 10 N hydrochloric acid was added dropwise, followed by, in portions, 2.5 g of 3-methyl-1-{3-[(3-nitropyrazolo[1,5-a]pyridin-2-yl)amino]propyl}-1H-imidazol-3-ium methylsulphate in 10 minutes.

At the end of addition, 1 ml of hydrochloric acid was added dropwise and reflux was maintained for 2 hours.

At the end of reduction, zinc was removed by filtration under argon on a bed of Celite and the filtrate was recovered in a flask containing 25 ml of previously cooled 6N hydrochloric isopropanol.

This solution was concentrated and cooled with ice. A light blue solid crystallized.

This light blue solid was drained on a No. 3 frit, washed with of 2×60 ml of isopropyl ether, and dried under vacuum in the presence of $P_2O_5$ and soda tablets. 1.8 g of a light blue solid corresponding to the expected compound was recovered.

NMR analyses ($^1$H 400 MHz and $^{13}$C 100.61 MHz DMSO $d_6$) and mass spectrometry were consistent with the expected structure.

The expected cation $C_{14}H_{19}N_6^+$ was mainly detected at m/z=271.

Example 13

Synthesis of N,N-dimethyl-N'-(3-nitropyrazolo[1,5-a]pyridin-2-yl)propane-1,3-diamine

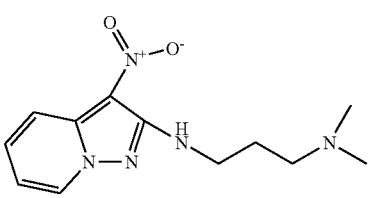

5 ml of NMP, 3 g of 2-(methylsulphonyl)-3-nitropyrazolo[1,5-a]pyridine and 3.78 ml of N,N-dimethyl-1,3-propanediamine were put in a 100-ml three-necked flask equipped with a bulb condenser, a thermometer and a magnetic stirrer, and heated to 80° C. for one hour.

The reaction mixture was poured onto 200 g of an ice-water mixture. The yellow compound which crystallized was drained on a No. 3 frit, washed with water 2×100 ml and then with 3×100 ml of isopropyl ether, and dried at 35° C. under vacuum in the presence of $P_2O_5$ for 12 hours. 2.69 g of a green solid corresponding to the expected compound was recovered.

NMR analyses ($^1$H 400 MHz and $^{13}$C 100.61 MHz DMSO $d_6$) and mass spectrometry were consistent with the expected structure.

Synthesis of N,N,N-trimethyl-3-[(3-nitropyrazolo[1,5-a]pyridin-2-yl)amino]propan-1-aminium methylsulphate

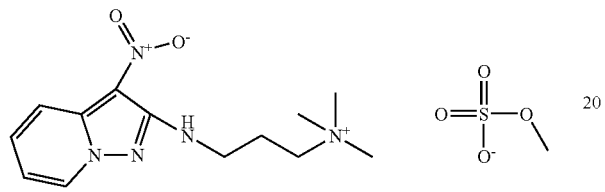

25 ml of THF, 2.63 g (0.01 mol) of N,N-dimethyl-N'-(3-nitropyrazolo[1,5-a]pyridin-2-yl)propane-1,3-diamine and 1.85 ml (0.02 mol) of dimethylsulphate were dropwise added at 50° C. to a 100-ml three-necked flask equipped with a bulb condenser, a thermometer and a magnetic stirrer.

The reaction was monitored by TLC (eluent: 95:5 dichloromethane/methanol).

The reaction mixture was allowed to return to room temperature and the yellow solid that formed was drained on a No. 3 frit, washed with 2×100 ml of THF and then with 3×100 ml of isopropyl ether, and then dried at 35° C. under vacuum in the presence of $P_2O_5$ for 12 hours. 3.84 g of a yellow solid corresponding to the expected structure was recovered.

NMR analyses ($^1$H 400 MHz and $^{13}$C 100.61 MHz DMSO $d_6$) and mass spectrometry complied.

Synthesis of 3-[(3-aminopyrazolo[1,5-a]pyridin-2-yl)amino]-N,N,N-trimethylpropan-1-aminium chloride dihydrochloride

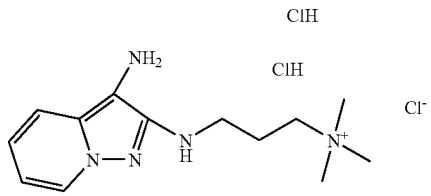

190 ml of ethanol and 9 g of zinc powder were put in a 250-ml three-necked flask equipped with a bulb condenser, a thermometer, a dropping funnel and a magnetic stirrer, and brought to reflux.

2 ml of 10 N hydrochloric acid and then a solution of 3 g of N,N,N-trimethyl-3-[(3-nitropyrazolo[1,5-a]pyridin-2-yl)amino]propan-1-aminium methylsulphate and 5 ml of water were dropwise added, respectively.

At the end of the addition, reflux was maintained for 45 minutes.

At the end of the reduction, the zinc was removed by filtration under argon on a bed of Celite and the filtrate was recovered in a flask containing 100 ml of previously cooled 6N hydrochloric isopropanol.

The very light blue solid that formed was drained on a No. 3 frit, washed with of 2×60 ml of isopropyl ether, and dried under vacuum in the presence of $P_2O_5$ and soda tablets. 2.37 g of a light blue solid corresponding to the expected compound was recovered.

NMR analyses ($^1$H 400 MHz and $^{13}$C 100.61 MHz DMSO $d_6$) and mass spectrometry were consistent with the expected structure.

The ions $[C_{13}H_{22}N_5]^+$, $[M+H]^{2+}$ as well as the fragment ion $[C_{10}H_{12}N_4]^+$ relating to the expected cation were mainly detected.

Example 14

Synthesis of N,N-dimethyl-1-(3-nitropyrazolo[1,5-a]pyridin-2-yl)pyrrolidin-3-amine

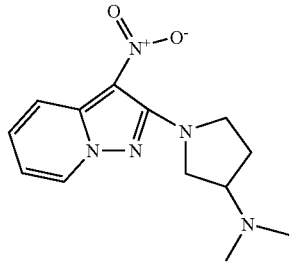

5 ml of NMP, 3 g of 2-(methylsulphonyl)-3-nitropyrazolo[1,5-a]pyridine and 3.77 ml of 3-(dimethylamino)pyrrolidine were put in a 100-ml three-necked flask equipped with a bulb condenser, a thermometer and a magnetic stirrer, and heated to 80° C. for one hour.

The reaction mixture was poured onto 200 g of an ice-water mixture. The yellow compound which crystallized was drained on a No. 3 frit, washed with water 2×100 ml and then with 3×100 ml of isopropyl ether, and then dried at 35° C. under vacuum in the presence of $P_2O_5$ for 12 hours. 3.26 g of a yellow solid corresponding to the expected compound was recovered.

NMR analyses ($^1$H 400 MHz and $^{13}$C 100.61 MHz DMSO $d_6$) and mass spectrometry were consistent with the expected structure.

The quasi-molecular ion $(MH)^+$ of the expected molecule, $C_{13}H_{17}N_5O_2$, was mainly detected.

Synthesis of N,N,N-trimethyl-1-(3-nitropyrazolo[1,5-a]pyridin-2-yl)pyrrolidin-3-aminium methylsulphate

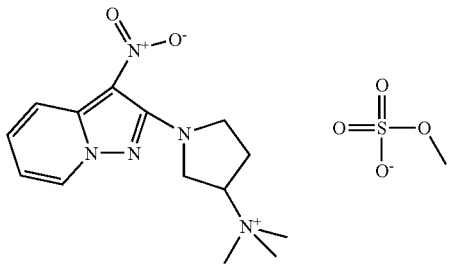

25 ml of THF, 3.26 g (0.01 mol) of N,N-dimethyl-1-(3-nitropyrazolo[1,5-a]pyridin-2-yl)pyrrolidin-3-amine and 1.89 ml (0.02 mol) of dimethylsulphate were dropwise added at 50° C. to a 100-ml three-necked flask equipped with a bulb condenser, a thermometer and a magnetic stirrer.

The reaction was monitored by TLC (eluent: 95:5 dichloromethane/methanol).

The reaction mixture was allowed to return to room temperature, and the yellow solid that formed was drained on a No. 3 frit, washed with 2×100 ml of THF and then 3×100 ml of isopropyl ether, and then dried at 35° C. under vacuum in the presence of $P_2O_5$ for 12 hours. 3.2 g of a yellow solid corresponding to the expected structure was recovered.

NMR analyses ($^1$H 400 MHz and $^{13}$C 100.61 MHz DMSO $d_6$) and mass spectrometry complied.

Synthesis of 1-(3-aminopyrazolo[1,5-a]pyridin-2-yl)-N,N,N-trimethylpyrrolidin-3-aminium chloride dihydrochloride

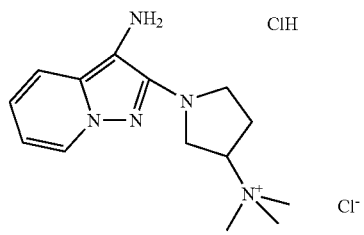

190 ml of ethanol and 9 g of zinc powder were put in a 250-ml three-necked flask equipped with a bulb condenser, a thermometer, a dropping funnel and a magnetic stirrer, and brought to reflux.

2 ml of 10 N hydrochloric acid and a solution of 3 g of N,N,N-trimethyl-3-[(3-nitropyrazolo[1,5-a]pyridin-2-yl)amino]propan-1-aminium methylsulphate and 5 ml of water were then added dropwise, respectively.

At the end of addition, reflux was maintained for 45 minutes.

At the end of reduction, zinc was removed by filtration under argon on a bed of Celite and the filtrate was recovered in a flask containing 100 ml of previously cooled 6N hydrochloric isopropanol.

The beige solid that formed was drained on a No. 3 frit, washed with 2×60 ml of isopropyl ether, and dried under vacuum in the presence of $P_2O_5$ and soda tablets. 2.83 g of a cream-colored solid corresponding to the expected compound was recovered.

NMR analyses ($^1$H 400 MHz and $^{13}$C 100.61 MHz DMSO $d_6$) and mass spectrometry were consistent with the expected structure.

The ions [C14H22N5]+, [M+H]2+ as well as the fragment ion [C11H13N4]+ relating to the expected cation were mainly detected.

Example 15

Synthesis of 2-(4-methylpiperazin-1-yl)-3-nitropyrazolo[1,5-a]pyridine

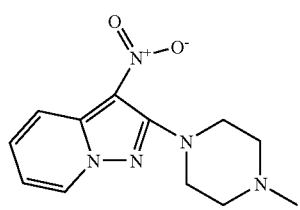

5 ml of NMP, 3 g of 2-(methylsulphonyl)-3-nitropyrazolo[1,5-a]pyridine and 3.3 ml of 1-methylpiperazine were put in a 100-ml three-necked flask equipped with a bulb condenser, a thermometer and a magnetic stirrer, and heated to 80° C. for 3 hours.

The reaction mixture was poured onto 200 g of an ice-water mixture. The yellow compound which crystallized was drained on a No. 3 frit, washed with water 2×100 ml and then with 3×100 ml of isopropyl ether, and then dried at 35° C. under vacuum in the presence of $P_2O_5$ for 12 hours. 2.35 g of a yellow solid corresponding to the expected compound was recovered.

NMR analyses ($^1$H 400 MHz and $^{13}$C 100.61 MHz DMSO $d_6$) and mass spectrometry were consistent with the expected structure.

$^1$H-NMR (DMSO-$d_6$): 2.23 (s, 3H), 2.5 (m, 4H), 3.41 (m, 4H), 7.31 (m, 1H), 7.82 (m, 1H), 8.19 (m, 1H), 8.82 (m, 1H)

The quasi-molecular ions [M+H]+, [M+H+CH$_3$CN]+, [2M+H]+ as well as the ion of the expected molecule $C_{12}H_{15}N_5O_2$ were mainly detected.

Synthesis of 1,1-dimethyl-4-(3-nitropyrazolo[1,5-a]pyridin-2-yl)piperazin-1-ium methylsulphate

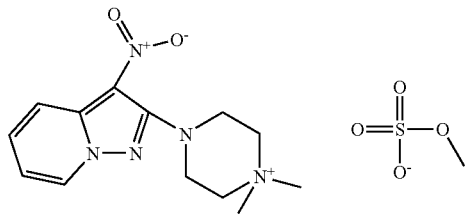

25 ml of THF, 2.35 g ( 0.01 mol) of 2-(4-methylpiperazin-1-yl)-3-nitropyrazolo[1,5-a]pyridine and 1.85 ml (0.02 mol) of dimethylsulphate were added dropwise at 50° C. to a 100-ml three-necked flask equipped with a bulb condenser, a thermometer and a magnetic stirrer.

The reaction was monitored by TLC (eluent: 95:5 dichloromethane/methanol).

The reaction mixture was allowed to return to room temperature and the yellow solid that formed was drained on a No. 3 frit, washed with 2×100 ml of THF and then with 3×100 ml of isopropyl ether, and then dried at 35° C. under vacuum in the presence of $P_2O_5$ for 12 hours. 3.2 g of a yellow solid corresponding to the expected structure was recovered.

NMR analyses ($^1$H 400 MHz and $^{13}$C 100.61 MHz DMSO $d_6$) and mass spectrometry complied.

Synthesis of 4-(3-aminopyrazolo[1,5-a]pyridin-2-yl)-1,1-dimethylpiperazin-1-ium chloride dihydrochloride

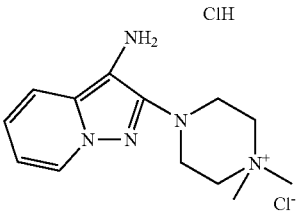

190 ml of ethanol and 9 g of zinc powder were put in a 250-ml three-necked flask equipped with a bulb condenser, a thermometer, a dropping funnel and a magnetic stirrer, and brought to reflux.

2 ml of 10 N hydrochloric acid and a solution of 3 g of 1,1-dimethyl-4-(3-nitropyrazolo[1,5-a]pyridin-2-yl)piperazin-1-ium methylsulphate and 5 ml of water were then added dropwise, respectively.

At the end of addition, reflux was maintained for 45 minutes.

At the end of reduction, the zinc was removed by filtration under argon on a bed of Celite and the filtrate was recovered in a flask containing 100 ml of previously cooled 6N hydrochloric isopropanol.

The beige solid that formed was drained on a No. 3 frit, washed with of 2×60 ml of isopropyl ether, and dried under vacuum in the presence of $P_2O_5$ and soda tablets. 3.31 g of a cream-colored solid corresponding to the expected compound was recovered.

NMR analyses ($^1$H 400 MHz and $^{13}$C 100.61 MHz DMSO $d_6$) and mass spectrometry were consistent with the expected structure.

The expected cation $[C_{13}H_{20}N_5]^+$ was mainly detected at m/z,ESP+=246.

Example 16

Synthesis of the chlorine chlorhydrate of 1-{2-[(3-aminopyrazolo[1,5-a]pyridin-2-yl)oxy]ethyl}-1-methylpiperidinium

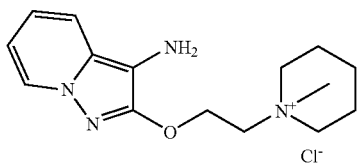

General Synthesis:

Synthesis of 3-nitro-2-(2-piperidin-1-ylethoxy)pyrazolo[1,5-a]pyridine 10 ml of water and 13.8 ml(0.103 mole) of N-(2-hydroxyethyl)piperidine were introduced into a 250 ml three necked flask equipped with a bulb condensor, a thermometer and a magnetic stirrer. The solution was cooled to zero ° C. A solution of 8.29 g (0.207 mole) of sodium carbonate and 20 ml water was then added over 15 minutes. The resulting solution was then agitated for 15 minutes and cooled to zero ° C.

A 100 ml solution of n-methylpyrrolidinone and 10 g (0,04145 mole) 2-(methylsulfonyl)-3-nitropyrazolo[1,5-a] pyridine was then added drop by drop over 20 minutes. A heterogenous purple solution was obtained, and was agitated for 4 hours and allowed to return to room temperature. The solid that formed was washed with water until the pH was neutral, and then with 4×50 ml of isopropyl ether. The solid was then dried at 35° C. under vacuum in the presence of $P_2O_5$ for 12 hours. 3.70 g of a beige solid corresponding to the expected compound was recovered.

NMR analyses ($^1$H 400 MHz and $^{13}$C 100.61 MHz DMSO $d_6$) and mass spectrometry are in accordance with the expected structure.

The expected cations $[M^+H]^+$, $[M^+Na]^+$, $[M^+Na^+CH_3OH]^+$, $[2M^+Na]$ were principally detected.

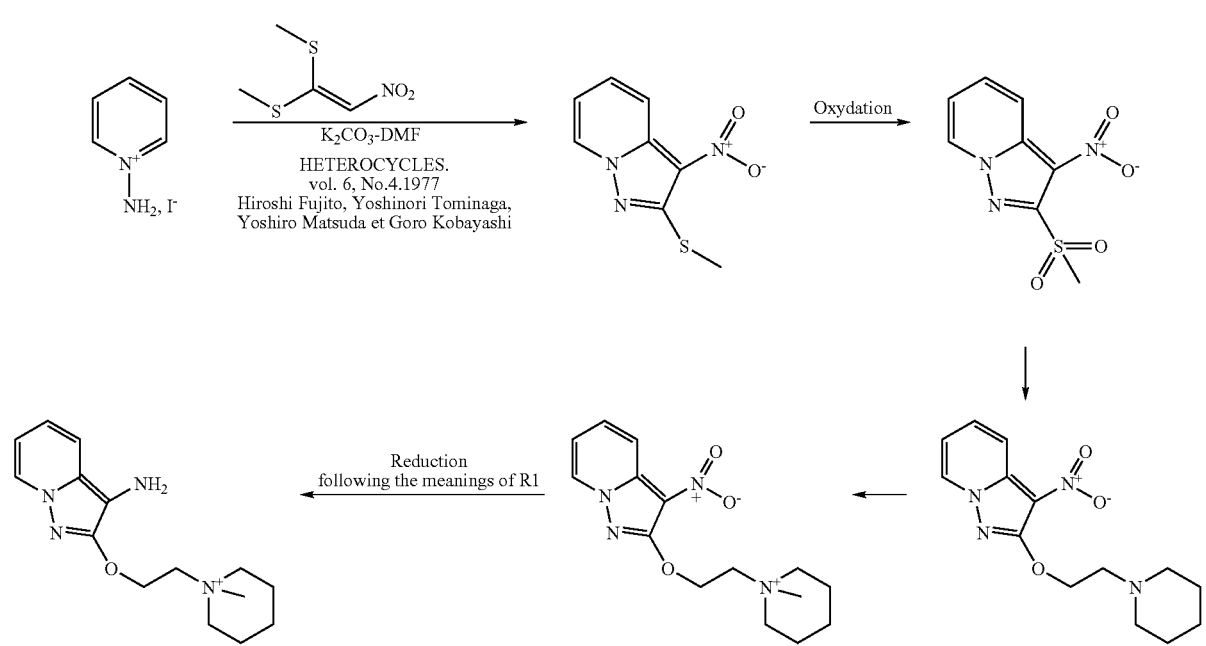

Synthesis of 1 methyl-1-{2-[(3-nitropyrazolo[1,5-a]pyridin-2-yl)oxy]ethyl}piperidinium methyl sulfate

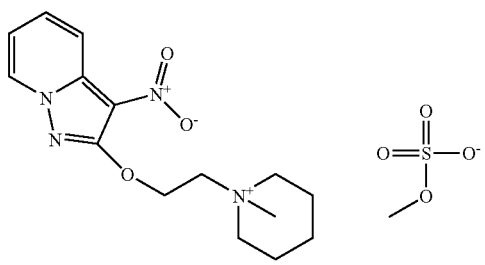

60 ml of THF, 6 g (0,0206 mole) of 3-nitro-2-(2-piperidin-1-ylethoxy)pyrazolo[1,5-a]pyridine were introduced into a 100 ml three necked flask equipped with a bulb condenser, a thermometer and a magnetic stirrer. 3.9 ml (0.0413 mole) of dimethylsulfate were added drop by drop at 20° C. The reaction was monitored by TLC (eluant: 95:5 Dichloromethane/Methanol). The solid that formed was drained on a number 3 frit, washed with 3×100 ml of THF and then with 3×100 ml of isopropyl ether. The solid was then dried under vacuum at 35° C. in the presence of $P_2O_5$, for 12 hours. 8.09 g of a beige solid corresponding to the structure was recovered.

The NMR analyses ($^1$H 400 MHz and $^{13}$C 100.61 MHz DMSO $d_6$) and mass spectrometry were in accordance with the expected structure.

50 ml of ethanol and 5 g of zinc powder were introduced into a 100 ml three necked flask equipped with a bulb condenser, a thermometer, and a magnetic stirrer and refluxed. 550 μl of acetic acid and a solution of 5 ml water and 5 g of methyl-1-{2-[(3-nitropyrazolo[1,5-a]pyridin-2-yl)oxy]ethyl}piperidinium methyl sulfate were then added drop by drop, respectively. The reaction was then refluxed for 18 hours. When the reduction was finished, zinc was removed by filtration in the presence of argon on a bed of Celite and the filtrate was collected in a flask containing 120 ml of previously cooled 6N hydrochloric isopropanol. The filtrate was evaporated then recrystallized several times with 60 ml of isopropanol. Slow crystallization of a purple solid was observed. The solid was drained on a number 3 frit and washed with 3×30 ml of ether. The solid was then dried under vacuum in the presence of $P_2O_5$ and soda tablets. 3.5 g of a pink powder corresponding to the expected compound was obtained.

The NMR analyses ($^1$H 400 MHz and $^{13}$C 100.61 MHz DMSO $d_6$) and mass spectrometry were in accordance with the expected structure.

The quasi molecular ions $[M^+H]^+$, $[M^+Na]^+$, $[M^+H^+ CH_3OH]$ and the expected molecule $C_{14}H_{20}N_4O$ were detected.

Synthesis of the chlorhydrate of 2-(2-piperidin-1-ylethoxy)pyrazolo[1,5-a]pyridin-3-amine

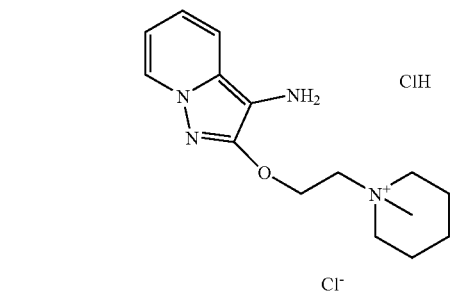

Example 17

Chlorine chlorhydrate of 2-[(3-aminopyrazolo[1,5-a]pyridin-2-yl)oxy]N,N,Ntrimethylethanaminium

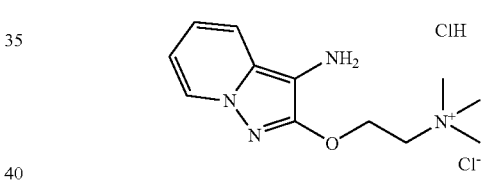

General Synthesis:

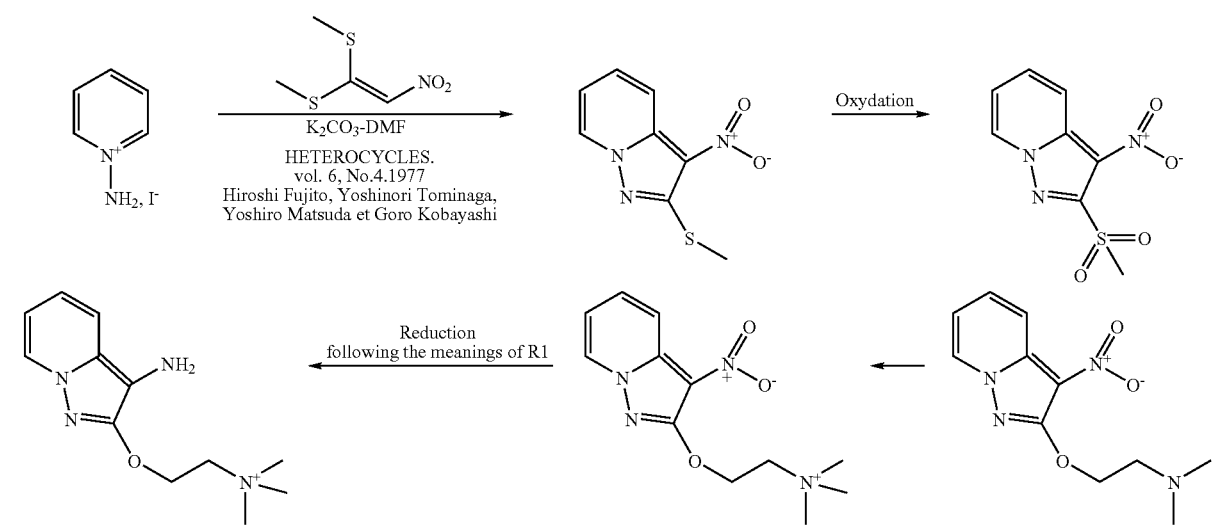

Synthesis of N,N-dimethyl-2-[(3-nitropyrazolo[1,5-a]pyridin-2-yl)oxy]ethanamine 10 ml of water and 10.3 ml (0.103 mol) of N,n-dimethyl-ethanolamine were introduced into a 250 ml three necked flask equipped with a bulb condenser, a thermometer and a magnetic stirrer and cooled to zero ° C. A solution of 8.29 g (0.207 mole) of sodium carbonate and 20 ml water was then added over 15 minutes. The resulting solution was then agitated for 15 minutes and cooled to zero ° C. A solution of 100 ml n-methylpyrrolidinone and 10 g (0.04145 mole) 2-(methylsulfonyl)-3-nitropyrazolo[1,5-a]pyridine was then added drop by drop over 20 minutes. A heterogenous purple solution resulted, which was agitated for 6 hours and allowed to return to room temperature. The solid that formed was washed with 500 ml of water. The resulting beige solid was washed with water until the pH was neutral, and then with 4×50 ml of isopropyl ether. The solid was then dried at 35° C. under vacuum in the presence of $P_2O_5$ for 12 hours. 5.01 g of a beige solid corresponding to the expected compound was obtained.

The NMR analyses ($^1$H 400 MHz and $^{13}$C 100.61 MHz DMSO $d_6$) and mass spectrometry were in accordance with the expected structure.

The quasi molecular ions [M$^+$H]$^+$, [M$^+$Na]$^+$, [M$^+$Na$^+$CH$_3$OH]$^+$, [2M$^+$Na]$^+$ were principally detected.

Sythesis of du N,N,N-trimethyl-2-[(3-nitropyrazolo[1,5-a]pyridin-2-yl)oxy]ethanaminium methyl sulfate

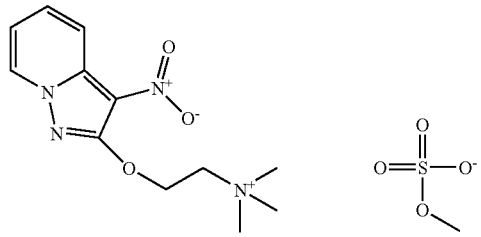

30 ml of THF, 3 g (0.01198 mole) of N,N-dimethyl-2-[(3-nitropyrazolo[1,5-a]pyridin-2-yl)oxy]ethanamine were introduced in a 100 ml three-necked flask equipped with a bulb condenser, a thermometer and a magnetic stirrer. 2.27 ml (0.02397 mole) of dimethylsulfate was then added drop by drop at 20° C. The reaction was monitored by TLC (eluant: 95:5 Dichloromethane/Methanol). The solid that formed was drained on a number 3 frit and washed with 2×50 ml of THF and 2×50 ml of isopropyl ether, respectively. The solid was then dried at 35° C. under vacuum in the presence of $P_2O_5$ for 12 hours. 4.50 g of a white solid corresponding to the expected compound was obtained.

The NMR analyses ($^1$H 400 MHz and $^{13}$C 100.61 MHz DMSO $d_6$) and mass spectrometry were in accordance with the expected structure.

Synthesis of the chlorine chlorhydrate of 2-[(3-aminopyrazolo[1,5-a]pyridin-2-yl)oxy]-N,N,N-trimethylethanaminium

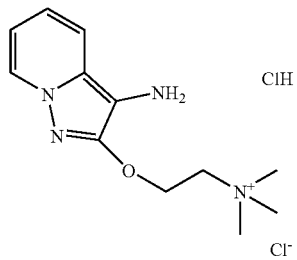

40 ml of ethanol and 4.5 g of zinc powder were introduced into a 100 ml three-necked flask equipped with a bulb condenser, a thermometer, and a magnetic stirrer and refluxed. Two drops of acetic acid were and then a solution of 4.5 ml water and 4.5 g N,N,N-trimethyl-2-[(3-nitropyrazolo[1,5-a]pyridin-2-yl)oxy]ethanaminium methyl sulfate were added, respectively. After this addition, 2 drops of acetic acid was added and the resultant mixture was refluxed for 18 hours. When the reduction was finished, zinc was filtered under argon on a bed of Celite. The filtrate was collected in a flask containing 100 ml of previously cooled 6N hydrochloric isopropanol. The filtrate was concentrated to ⅓ and then refreshed several times with ether. Slow crystallization of a purple solid was observed. This solid was drained on a number 3 frit, washed with the isopropanol and 3×30 ml of ether, respectively. The resultant solid was dried under vacuum in the presence of $P_2O_5$ and soda tablets. 2.85 g of a purple powder corresponding to the expected compound was obtained.

The NMR analyses ($^1$H 400 MHz and $^{13}$C 100.61 MHz DMSO $d_6$) and mass spectrometry were in accordance with the expected structure.

The quasi molecular ions [M$^+$H]$^+$, [M$^+$Na]$^+$, [M$^+$H$^+$CH$_3$OH] and the expected molecule $C_{11}H_{16}N_4O$ were princpally detected.

Example 18

Chlorine chlorhydrate of 1-{2-[(3-aminopyrazolo[1,5-a]pyridin-2-yl)amino]ethyl}-1,2,6-trimethylpiperidinium

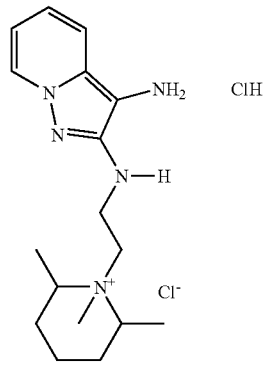

Synthesis of N-[2-(2,6-dimethylpiperidin-1-yl)ethyl]-3-nitropyrazolo[1,5-a]pyridin-2-amine.

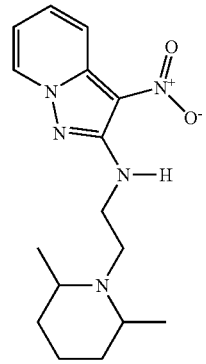

10 ml of NMP, 5 g (0.0207 moles) of 2-methanesulfanyl-3-nitro-pyrazol[1,5-a]pyridine and 5 g (0.032 mol) of 3-aminopropyidimethylpiperidin-1-yl)ethanamine were introduced into a 30 ml three necked flask equipped with a bulb condenser, a thermometer and a magnetic stirrer. While stirring, the mixture was heated to 70° C. with an oil bath for 4 hours. The reaction was monitored by TLC (eluant: 98:2 Dichloromethane/Methanol). The resultant mixture was cooled to room temperature. The mixture was then poured onto 150 g of ice, and a solid precipitated. The yellow precipitate was drained on a number 3 frit and then washed several times with water. The solid was then dried at 40° C. under vacuum in the presence of $P_2O_5$. 3.49 g of a yellow solid corresponding to the expected compound was obtained.

The NMR analyses ($^1H$ 400 MHz and $^{13}C$ 100.61 MHz DMSO $d_6$) were in accordance with the expected structure.

The mass of the composite $C_{16}H_{23}N_5O_2$ was detected by mass spectrometry.

Synthesis of 2,6-trimethyl-1-{2-[(3-nitropyrazolo[1,5-a]pyridin-2-yl)amino]ethyl}piperidinium methyl sulfate

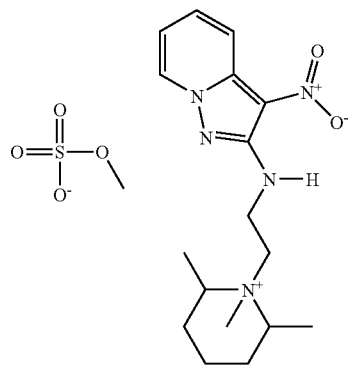

15 ml of THF was introduced into a 30 ml three necked flask equipped with a bulb condensor, a thermometer, a magnetic stirrer, and a 50 ml flow bulb. While stirring, 3.25 g (0.0107 moles) of N-[2-(2,6-dimethylpiperidin-1-yl)ethyl]-3-nitropyrazolo[1,5-a]pyridin-2-amine was introduced. 2.13 ml (0.02250 mole) of dimethylsulfate was then added drop by drop, resulting in the formation of a yellow precipitate. The reaction was monitored by TLC (eluant: dichloromethane/methanol 98: 2) for 24 hours. The solid formed was drained and washed several times with THF. The solid was then dried drying under vacuum in the presence of $P_2O_5$. 4.37 g of a yellow powder corresponding to the expectite compound was obtained.

The NMR analyses ($^1H$ 400 MHz and $^{13}C$ 100.61 MHz DMSO $d_6$) were in accordance with the expected structure.

The expected molecular ions $M^+$ $[C_{17}H_{25}N_5O]^+$ and the ion $[CH_3O_4S]^-$ were principally detected.

Synthesis of the chlorine chlorhydrate of 1-{2-[(3-aminopyrazolo[1,5-a]pyridin-2-yl)amino]ethyl}-1,2,6-trimethylpiperidinium

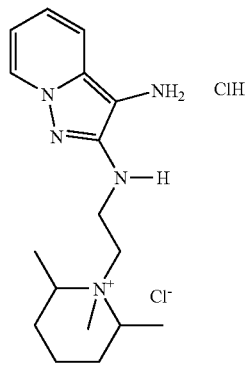

100 ml of ethanol and 3.75 g of zinc were introduced in a 250 ml three necked flask equipped with a bulb condensor, a thermometer, and a magnetic stirrer and refluxed. 5 drops of acetic acid was then added. A solution of 3.75 g of 1,2,6-trimethyl-1-{2-[(3-nitropyrazolo[1,5-a]pyridin-2yl)amino]ethyl}piperidinium methyl sulfate, 20 ml ethanol and 4 ml water was then added drop by drop over 30 minutes and refluxed for 24 hours. When the reduction was finished, zinc was filtered from the solution on a bed of Celite and the remaining solution was recovered with 70 ml of hydrochloric isopropanol that was previously cooled in a bath of dry ice. The zinc was washed with ethanol. The remaining solution was concentrated to 1/3 and cooled to zero ° C. Crystallization of a blue gray solid resulted. The blue gray solid was drained on a number 3 frit and dried under vacuum in the presence of $P_2O_5$. 1.09 g of a blue gray powder corresponding to the expected compound was obtained.

The NMR analyses ($^1H$ 400 MHz and $^{13}C$ 100.61 MHz DMSO $d_6$) were in accordance with the expected structure.

The expected molecular ion $M^+$ $[C_{17}H_{28}N_5]^+$ was principally detected.

Example 19

Chlorine chlorhydrate of 1-{3-[(3-aminopyrazolo[1,5-a]pyridin-2-yl)amino]propyl}-1-methylpiperidinium

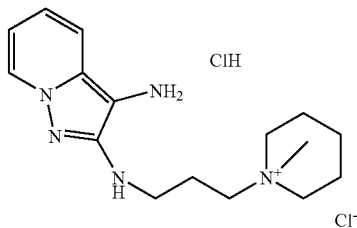

Synthesis of 3-nitro-N-(3-piperidin-1-ylpropyl)pyrazolo[1,5-a]pyridin-2-amine

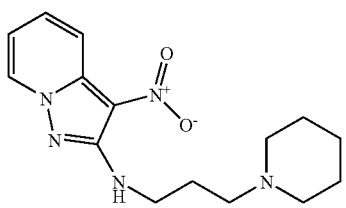

10 ml of NMP, 4.5 g (0.0159 moles) of 2-methanesulfanyl-3-nitro-pyrazol[1,5-a]pyridine and 5 g (0.032 mol) of 2-(2,6-dimethylpiperidin-1-yl)ethanamine were introduced into a 30 ml three necked flask equipped with a bulb condensor, a thermometer and a magnetic stirrer. While stirring, the mixture was heated to 70° C. for 4 hours in an oil bath. The reaction was monitored by TLC (eluant: 98:2 Dichloromethane/Methanol). The mixture was then cooled to room temperature, and poured over 150 g of ice. A yellow precipitate formed. The precipitate was drained on a number 4 frit and then washed with water several times. The solid was then dried at 40° C. under vacuum in the presence of $P_2O_5$. 3.49 g of a yellow solid corresponding to the expected compound was obtained.

The NMR analyses ($^1$H 400 MHz and $^{13}$C 100.61 MHz DMSO $d_6$) were in accordance with the expected structure.

The mass of the expected composite $C_{16}H_{23}N_5O_2$ was detected by mass spectrometry.

Synthesis of methyl-1-{3-[(3-nitropyrazolo[1,5-a]pyridin-2-yl)amino]propyl}piperidinium methyl sulfate

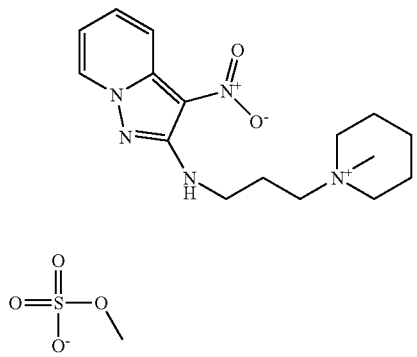

15 mL of THF was introduced into a 30 ml three necked flask equipped with a bulb condenser, a thermometer, a 50 ml flow, and a magnetic stirrer. While stirring, 3.25 g (0.0107 moles) of 3-nitro-N-(3-piperidin-1-ylpropyl)pyrazolo[1,5-a]pyridin-2-amine were added. 2.13 ml (0.0225 mole) of dimethylsulfate was then added drop by drop, resulting in the formation of a yellow precipitate. The reaction was monitored by TLC (eluant: dichloromethane/methanol 98:2) for 24 hours. The formed solid is drained and then washed several times with THF. The solid is then dried under vacuum in the presence of $P_2O_5$. 4.37 g of yellow powder corresponding to the expected compound was obtained.

The NMR analyses ($^1$H 400 MHz and $^{13}$C 100.61 MHz DMSO $d_6$) were in accordance with the expected structure.

The expected molecular ion M$^+$ $[C_{17}H_{24}N_5O_2]^+$ was principally detected, as well as the ion $[CH_3O_4S]$.

Synthesis of the chlorine chlorhydrate of 1-{3-[(3-aminopyrazolo[1,5-a]pyridin-2-yl)amino]propyl}-1-methylpiperidinium

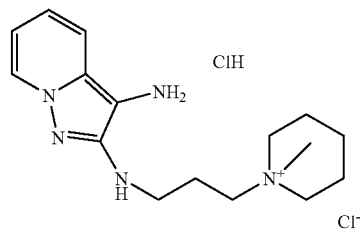

100 ml of ethanol and 4.37 g of zinc were introduced into a 250 ml three necked flask equipped with a bulb condensor, a thermometer and a magnetic stirrer and refluxed. 5 drops of acetic acid was then added. A solution of 4.37 g of 1-methyl-1-{3-[(3-nitropyrazolo[1,5-a]pyridin-2-yl)amino]propyl}piperidiniummethyl sulfate, 15 ml ethanol and 5 ml of water was then added drop by drop over 30 minutes, and the reflux was maintained for 24 hours.

When the reduction was finished, zinc was filtered from the solution on a bed of Celite and the remaining solution was recovered in 70 ml of hydrochloric isopropanol that was previously cooled in a bath of dry ice. The zinc was washed with ethanol. The remaining solution was concentrated to 1/3 and cooled to zero ° C., resulting in the crystallization of a clear blue solid. The clear blue solid was drained on a number 3 frit and dried under vacuum in the presence of $P_2O_5$. 3.41 g of a clear blue powder corresponding to the expected compound was obtained.

The NMR analyses ($^1$H 400 MHz and $^{13}$C 100.61 MHz DMSO $d_6$) were in accordance with the expected structure.

The expected molecular ion M$^+$ $[C_{16}H_{26}N_5]^+$ was principally detected.

Example 20

Chlorine Chlorhydrate of 1-{4-[(3-aminopyrazolo[1,5-a]pyridin-2-yl)amino]butyl}-1-methylpiperidinium

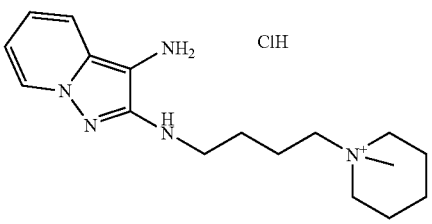

General Synthesis:

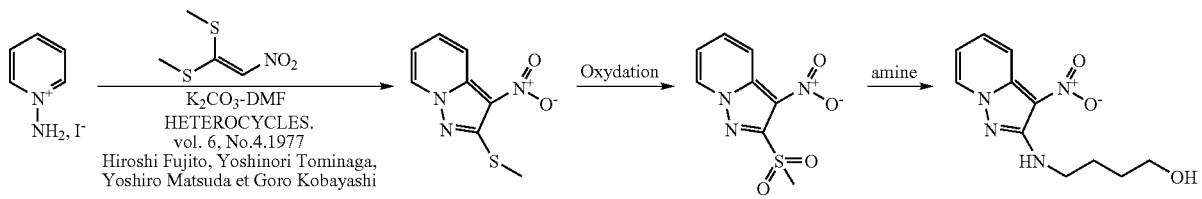

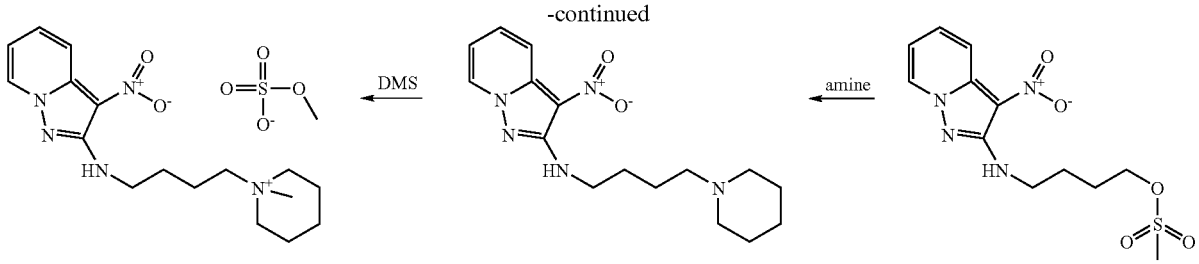

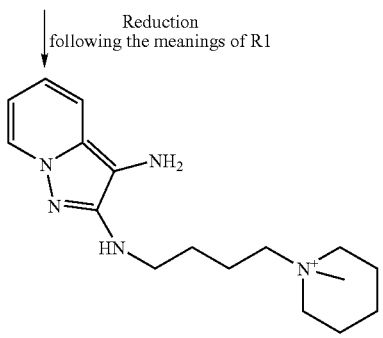

Synthese du 4-[(3-nitropyrazolo[1,5-a]pyridin-2-yl)amino]butan-1-ol

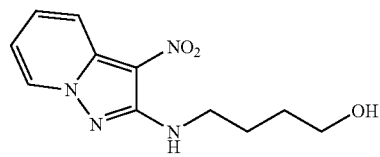

10 ml of NMP, 5 g (0.0207 moles) 2-methanesulfanyl-3-nitro-pyrazol[1,5-a]pyridine and 5 g (0.032 mol) of 4-amino-1-butanol were introduced into a 30 ml three necked flask equipped with a bulb condenser, a thermometer and a magnetic stirrer. While stirring, the mixture was heated to 70° C. in an oil bath for 4 hours. The reaction was monitored by TLC (eluant: 98:2 Dichloromethane/Methanol). The mixture was then cooled to room temperature, and poured over 150 g of ice. A yellow solid precipitated. The yellow solid was drained on a number 3 frit and washed several times with water. The solid was then dried under vacuum at 40° C. in the presence of $P_2O_5$. 4.4 g of a yellow solid corresponding to the expected composition was obtained.

The NMR analyses ($^1$H 400 MHz and $^{13}$C 100.61 MHz DMSO $d_6$) were in accordance with the expected structure.

The mass of the expected composite $C_{11}H_{14}N_4O_2$ was detected via mass spectrometry.

Synthesis of 4-[(3-nitropyrazolo[1,5-a]pyridin-2-yl)amino]butyl methanesulfonate

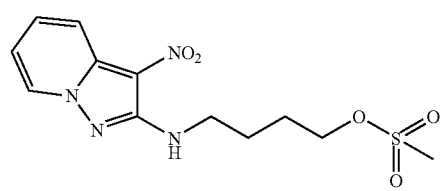

40 ml of THF, 3.4 g (0.01358 moles) 4-[(3-nitropyrazolo[1,5-a]pyridin-2-yl)amino]butan-1-ol were introduced into a 100 ml three necked flask equipped with a bulb condenser, a thermometer and a magnetic stirrer. The solution was cooled to zero ° C. 5.67 ml (0.0407 mole) of triethylamine was then added. 3.27 ml(0.04075 mole) of methyl chloride was then added drop by drop over 30 minutes. The solution was stirred for 30 minutes at zero ° C. and then for 2 hours at ambient temperature. The reaction was monitored by TLC (eluant: 98:2 Dichloromethane/Methanol). A yellow solid formed, and was drained on a number 4 frit and washed several times with THF, 2×30 ml water, and 2×20 ml of THF. The solid was then dried under vacuum at 40° C. in the presence of $P_2O_5$. 3.87 g of a yellow solid corresponding to the expected composition was obtained.

The NMR analyses ($^1$H 400 MHz and $^{13}$C 100.61 MHz DMSO $d_6$) were in accordance with the expected structure.

The mass of the expected composite $C_{12}H_{16}N_4O_5S$ was detected by mass spectrometry. The quasi molecular ions MH$^+$; [M$^+$Na]$^+$; [2M$^+$Na]$^+$ and the expected molecule $C_{12}H_{16}N_4O_5S$ were principally detected.

Example 21

Chorine chlorhydrate of 1-{4-[(3-aminopyrazolo[1,5-a]pyridin-2-yl)amino]butyl}-1-methylpiperidinium

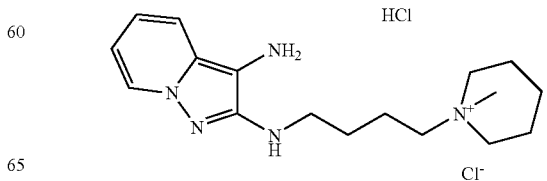

Synthesis of 3-nitro-N-(4-piperidin-1-ylbutyl)pyrazolo[1,5-a]pyridin-2-amine

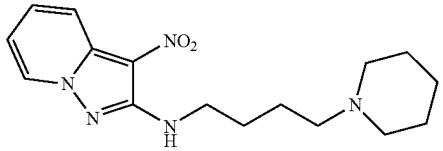

20 ml of butanol, 3.87 g (0.01178 moles) of 4-[(3-nitropyrazolo[1,5-a]pyridin-2-yl)amino]butyl methanesulfonate and 3.09 ml (0.0353 mol) of piperidine were introduced in a 30 ml three necked flask equipped with a bulb condensor, a thermometer and a magnetic stirrer. While stirring, the solution was heated to 100° C. in an oil bath for 4 hours. The reaction was monitored by TLC (eluant: 98:2 Dichloromethane/Methanol). The solution was then cooled to zero ° C., resulting in the crysallization of the expected composite. The compoiste was drained on a number 4 frit and then washed with isopropanol several times. The composite was then dried under vacuum at 40° C. in the presence of $P_2O_5$. 2.21 g of a yellow solid corresponding to the expected composition was obtained.

The NMR analyses ($^1$H 400 MHz and $^{13}$C 100.61 MHz DMSO $d_6$) were in accordance with the expected structure.

The quasi molecular ions $MH^+$;$[M^+Na]^+$,$[M^+K^+ CH_3COOH]^+$,$[2M^+H]^+$ and the expected molecule $C_{16}H_{23}N_5O_2$ were principally detected

Synthesis of 1-methyl-1-{4-[(3-nitropyrazolo[1,5-a]pyridin-2-yl)amino]butyl}piperidiniummethylsulfate

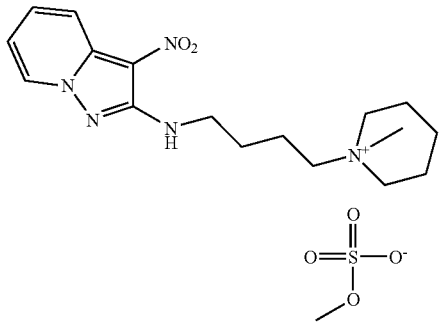

15 ml THF was introduced into a 30 ml equipped with a bulb condensor, a thermometer and a magnetic stirrer. 2.21 g (0.00696 moles) of 3-nitro-N-(4-piperidin-1-ylbutyl)pyrazolo[1,5-a]pyridin-2-amine were then added. 1.38 ml (0.0146 mole) of dimethylsulfate was then added droop by drop, resulting in the formation of a yellow precipitate. The reaction was monitored by TLC (eluant: dichloromethane/methanol 98:2) for 24 hours. The solid was drained and then washed several times with THF. The solid was then dried under vacuum in the presence of $P_2O_5$. 2.80 g of a yellow powder corresponding to the expected composition was obtained.

The NMR analyses ($^1$H 400 MHz and $^{13}$C 100.61 MHz DMSO $d_6$) were in accordance with the expected structure.

The expected molecular ion $M^+$ $[C_{17}H_{26}N_5O_2]^+$ was principally detected, as well as the ion $[CH_3O_4S]$.

Synthesis of the chlorine chlorhydrate of 1-{4-[(3-aminopyrazolo[1,5-a]pyridin-2-yl)amino]butyl}-1-methylpiperidinium

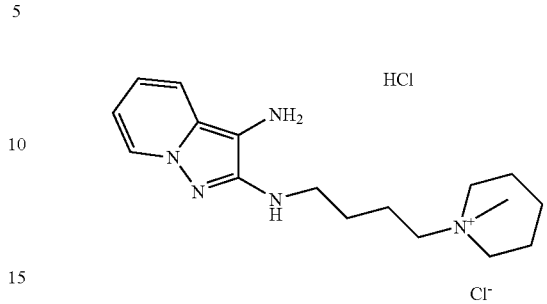

70 ml of ethanol and 2.80 g of zinc were introduced into a 250 ml three necked flask equipped with a bulb condensor, a thermometer and a magnetic stirrer and refluxed. 5 drops of acetic acid was then added. A solution of 2.80 g of 1-methyl-1-{4-[(3-nitropyrazolo[1,5-a]pyridin-2-yl)amino]butyl}piperidinium methyl sulfate, 15 ml ethanol and 3 ml water was then added drop by drop over 30 minutes and the reflux was maintained for 24 hours.

When the reduction was finished, zinc was filtered from the solution on a bed of Celite and the remaining solution was recovered 70 ml of hydrochloric isopropanol previously cooled with bath of dry ice. The zinc was washed ethanol. The remaining solution was concentrated to 1/3 and cooled to zero degrees, resulting in the crystallization of a clear blue solid. The clear blue solid was drained on a number 3 frit and dried under vacuum in the presence of $P_2O_5$. 2.16 g of a clear blue powder corresponding to the expected composition was obtained.

The NMR analyses ($^1$H 400 MHz and $^{13}$C 100.61 MHz DMSO $d_6$) were in accordance with the expected structure.

The expected molecular ion $M^+$ $[C_{17}H_{28}N_5]^+$ was principally detected.

Example 22

Chlorine chlorhydrate of 1-{5-[(3-aminopyrazolo[1,5-a]pyridin-2-yl)amino]pentyl}-1-methylpiperidinium

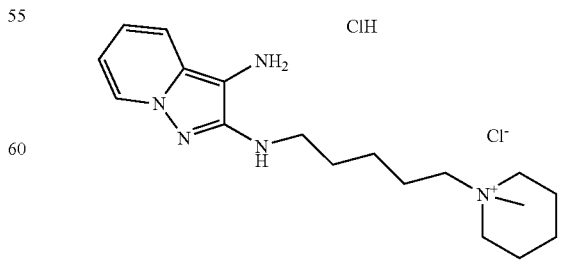

General Synthesis:

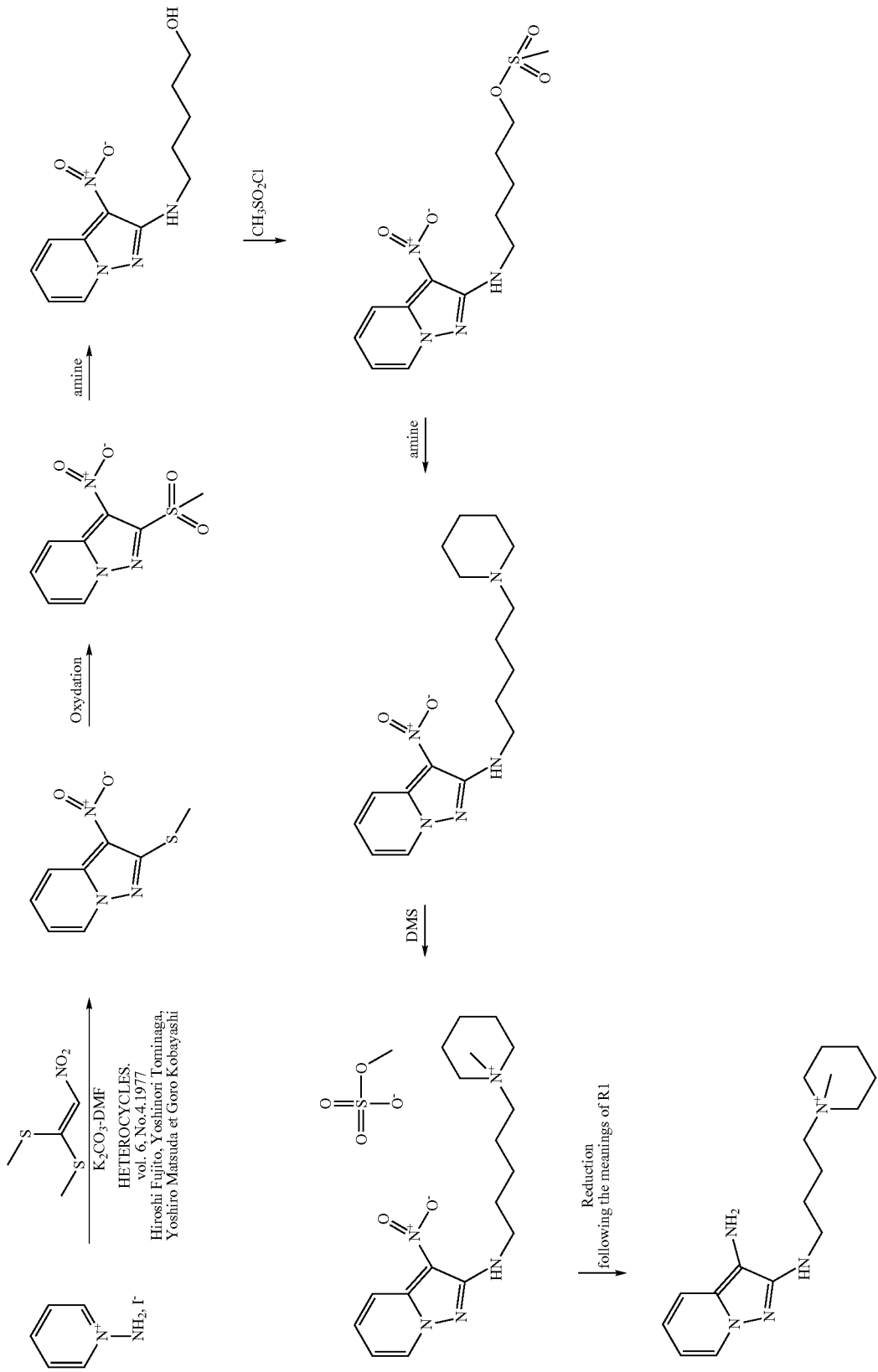

Synthesis of 5-[(3-nitropyrazolo[1,5-a]pyridin-2-yl)amino]pentan-1-ol

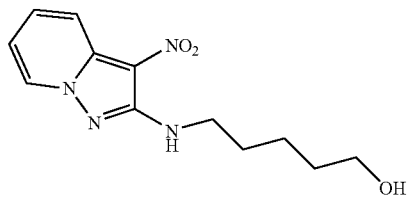

10 ml of NMP, 5 g (0.0207 moles) of 2-methanesulfanyl-3-nitro-pyrazol[1,5-a]pyridine and 5.34 g (0.0518 mol) of 5-amino-1-pentanol were introduced in a 30 ml three necked flask equipped with a bulb condenser, a thermometer and a magnetic stirrer. While stirring, the mixture was heated to 70° C. in an oil bath for 4 hours. The reaction was monitored by TLC (eluant: 98:2 Dichloromethane/Methanol). The solution was then cooled to room temperature and poured over 150 g of ice, resulting in the precipitation of yellow composite. The yellow composite was drained on a number 4 frit and washed with water several times. The composited was then dried under vacuum at 40° C. and in the presence of $P_2O_5$. 4.48G of a yellow solid corresponding to the expected composition was obtained.

The NMR analyses ($^1H$ 400 MHz and $^{13}C$ 100.61 MHz DMSO $d_6$) were in accordance with the expected structure.

The mass of the expected composite $C_{11}H_{14}N_4O_2$ was detected by mass spectrometry. The quasi molecular ions $MH^+$; $[M^+Na]^+$; $[2M^+Na]^+$ and the expected molecule $C_{12}H_{16}N_4O_3$ were principally detected.

Synthesis of 5-[(3-nitropyrazolo[1,5-a]pyridin-2-yl)amino]pentyl methanesulfonate

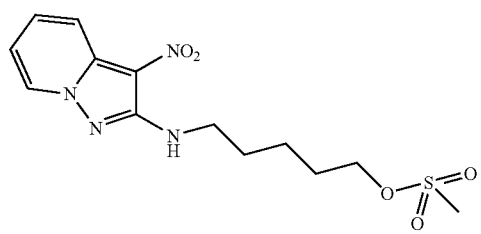

40 ml of THF, 3.48 g (0.01316 moles) 5-[(3-nitropyrazolo[1,5-a]pyridin-2-yl)amino]pentan-1-oil were introduced into a 100 ml three necked flask equipped with a bulb condenser, a thermometer and a magnetic stirrer. The mixture was cooled to zero ° C. 5.5 ml (0.0395 mole) of triethylamine was then added. 3.17 ml (0.03950 mole) of methyl chloride was added drop by drop over 30 minutes. Stirring was maintained at 0° C. for 30 minutes and then for 2 hours at ambient temperature. The reaction was monitored by TLC (eluant: 98:2 Dichloromethane/Methanol). A yellow solid formed. The solid was drained on a number 4 frit and then washed several times with THF, 2×30 ml water and 2×20 ml THF. The solid was then dried under vacuum at 40° C. in the presence of $P_2O_5$. 3.66 g of a yellow solid corresponding to the expected composition was obtained.

The NMR analyses ($^1H$ 400 MHz and $^{13}C$ 100.61 MHz DMSO $d_6$) were in accordance with the expected structure.

The mass of the expected composite $C_{13}H_{18}N_4O_5S$ was detected via mass spectrometry. The quasi molecular ions $MH^+$; $[M^+Na]^+$, $[2M^+Na]^+$ and the expected molecule $C_{13}H_{18}N_4O_5S$ were principally detected

Synthesis of 3-nitro-N-(5-piperidin-1-ylpentyl)pyrazolo[1,5-a]pyridin-2-amine

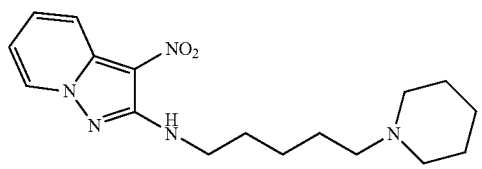

20 ml of butanol, 3.66 g (0.0069 moles) of 5-[(3-nitropyrazolo[1,5-a]pyridin-2-yl)amino]pentyl methanesulfonate and 2.80 ml (0.03207 mol) of piperidine were introduced into a 30 ml three necked flask equipeped with a bulb condensor, a thermometer and magnetic stirrer. While stirring, the mixture was heated to 100° C. in an oil bath for 4 hours. The reaction was monitored by TLC (eluant: 98:2 Dichloromethane/Methanol). The mixture was then cooled to zero ° C., resulting in the crystallization of a solid. The solid was drained on a number 4 frit and then washed with isopropanol several times. The solid was then dried under vacuum at 40° C. in the presence of $P_2O_5$. 2.19 g of a beige solid corresponding to the expected composition was obtained.

The NMR analyses ($^1H$ 400 MHz and $^{13}C$ 100.61 MHz DMSO $d_6$) were in accordance with the expected structure.

The quasi molecular ions $MH^+$;$[M^+Na]^+$,$[M^+K^+CH3COOH]^+$,$[2M^+H]$ and the expected molecule $C_{17}H_{25}N_5O_2$ were principally detected

Synthesis of 1-methyl-1-{5-[(3-nitropyrazolo[1,5-a]pyridin-2-yl)amino]pentyl}piperidiniummethyl sulfate

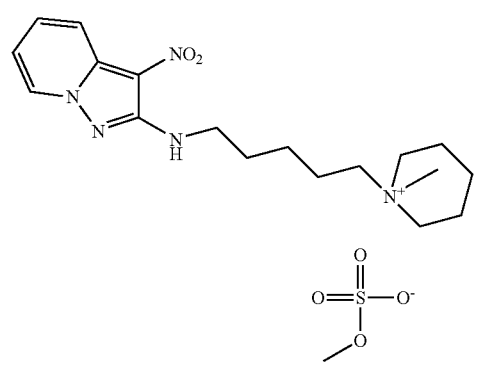

15 ml of THF was introduced into a 30 ml three necked flask equipped with a bulb condensor, a thermometer, a 50 ml flow bulb and a magnetic stirrer. 2.19 g (0.0066 moles) of 3-nitro-N-(5-piperidin-1-ylpentyl)pyrazolo[1,5-a]pyridin-2- amine was then added. 1.31 ml (0.01387 mole) of dimethylsulfate was then added drop by drop, resulting in the formation of a yellow precipitate. The reaction was monitored by TLC (eluant: dichloromethane/methanol 98:2) for 24 hours. The solid was drained and then washed several times with THF. The solid was then dried under vacuum in the presence of $P_2O_5$. 2.82 g of a clear yellow powder corresponding to the expected composition was obtained.

The NMR analyses ($^1$H 400 MHz and $^{13}$C 100.61 MHz DMSO $d_6$) were in accordance with the expected structure.

The expected molecular ion $M^+$ $[C_{18}H_{28}N_5O_2]^+$ and the ion $[CH_3O_4S]$ were principally detected.

Synthesis of the chlorine chlorhydrate of 1-{5-[(3-aminopyrazolo[1,5-a]pyridin-2-yl)amino]pentyl}-1-methylpiperidinium

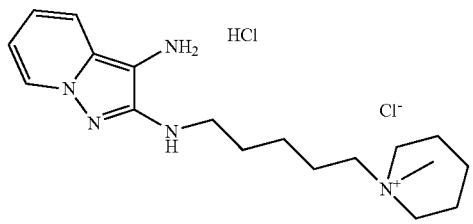

70 ml of ethanol and 2.80 g of zinc were introduced into a 250 ml three necked flask equipped with a bulb condenser, a thermometer and a magnetic stirrer and refluxed. 5 drops of acetic acid was then added. A solution of 2.80 g of 1-methyl-1-{4-[(3-nitropyrazolo[1,5-a]pyridin-2-yl)amino]butyl}piperidinium methyl sulfate, 15 ml ethanol and 3 ml water was then added drop by drop over 30 minutes and the reflux was maintained for 24 hours. When the reduction was finished, zinc was removed from the solution by filtration on a bed of Celite. The remaining solution was recovered in 70 ml of hydrochloric isopropanol that was previously cooled by a bath of dry ice. The zinc was washed with ethanol. The remaining solution was concentrated to 1/3 and cooled to zero degrees, resulting in the crystallization of a clear blue solid. The clear blue solid was drained on a number 3 frit and dried under vacuum in the presence of $P_2O_5$. 2.16 g of a clear blue powder corresponding to the expected composition was obtained.

The NMR analyses ($^1$H 400 MHz and $^{13}$C 100.61 MHz DMSO $d_6$) were in accordance with the expected structure.

The expected cation $[C_{18}H_{30}N_5]^+$ was principally detected at m/z,ESP+=316, 158,174 (corresponding respectively to $[M]^+$, $[M^+H]_2^+$, $[M^+H^+CH_3OH]_2^+$.

Example 23

Chlorine Chlorhydrate of 1-{2-[(3-aminopyrazolo[1,5-a]pyridin-2-yl)amino]ethyl}-3-methyl-1H-imidazol-3-ium

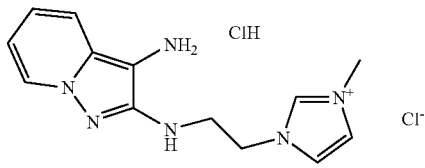

General Synthesis:

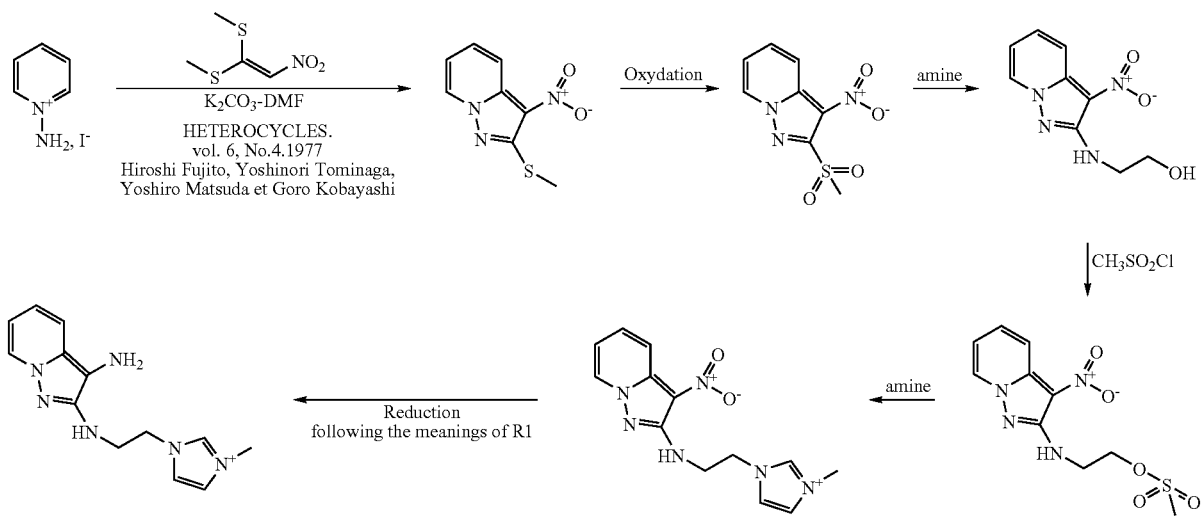

Synthesis of 2-[(3-nitropyrazolo[1,5-a]pyridin-2-yl)amino]ethanol

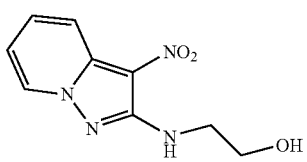

50 ml of NMP, 5 g (0.0207 moles) of 2-methanesulfanyl-3-nitro-pyrazol[1,5-a]pyridine and 6.25 ml (0.0103 mol) of ethanolamine were introduced in a 100 ml three necked flask equipped with a bulb condenser, a thermometer and a magnetic stirrer. While stirring, the mixture was heated to 80° C. in an oil bath for 2 hours. The reaction was monitored by TLC (eluant: 98:2 Dichloromethane/Methanol). The mixture was then cooled to ambient temperature and poured over 300 g of ice. A yellow precipitate formed. The precipitate was drained on a number 4 frit and then washed to water several times. The precipitate was then dried under vacuum at 40° C. in the presence of $P_2O_5$. 4.20 g of a yellow solid corresponding to the expected composition was obtained.

The NMR analyses ($^1H$ 400 MHz and $^{13}C$ 100.61 MHz DMSO $d_6$) were in accordance with the expected structure.

The mass of the expected composition $C_9H_{10}N_4O_3$ was detected by mass spectrometry.

Synthesis of
2-[(3-nitropyrazolo[1,5-a]pyridin-2-yl)amino]ethyl methanesulfonate

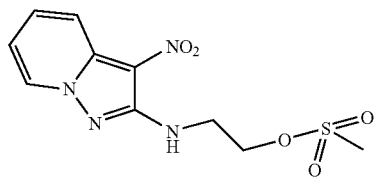

40 ml of THF and 4.2 g (0.01316 moles) of 2-[(3-nitropyrazolo[1,5-a]pyridin-2-yl)amino]ethanol were introduced into a 100 ml three necked flask equipped with a bulb condenser, a thermometer and a magnetic stirrer. The mixture was cooled to zero ° C. 3.16 ml (0.02268 mole) of triethylamine was then added. 1.66 ml (0,02079 mole) of methyl chloride was then added drop by drop over 30 minutes. Stirring was maintained for 30 minutes to zero ° C. and then for 2 hours at ambient temperature. The reaction was monitored by TLC (eluant: 98:2 Dichloromethane/Methanol). A yellow solid formed. The yellow solid was drained on a number 4 frit and then several times with THF, 2×30 ml water and 2×20 ml THF. The solid was then dried under vacuum at 40° C. in the presence of $P_2O_5$. 4.03 g of a yellow solid corresponding to the expected composition was obtained.

The NMR analyses ($^1H$ 400 MHz and $^{13}C$ 100.61 MHz DMSO $d_6$) were in accordance with the expected structure.

The mass of the expected composite $C_{10}H_{12}N_4O_5S$ was detected by mass spectrometry. The quasi molecular ions $MH^+$; $[M^+Na]^+,[2M^+Na]^+,[M^-H]^-$ and the expected molecule $C_{10}H_{12}N_4O_5S$ were principally detected.

Synthesis of the chloride of 3-methyl-1-{2-[(3-nitropyrazolo[1,5-a]pyridin-2-yl)amino]ethyl}-1H-imidazol-3-ium

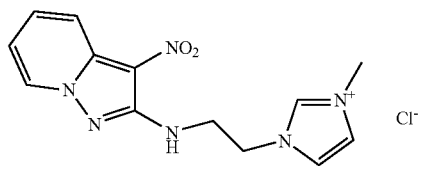

3 ml of butanol, 1.0 g (0.0033 moles) of 2-[(3-nitropyrazolo[1,5-a]pyridin-2-yl)amino]ethyl methanesulfonate and (0.0099 mol) of 1-methyimidazole were introduced into a 30 ml three necked flask equipped with a bulb condenser, a thermometer and a magnetic stirrer. While stirring, the solution was heated to 100° C. in an oil bath for 4 hours. The reaction was monitored by TLC (eluant: 98:2 Dichloromethane/Methanol). The mixture was then cooled to zero ° C. and 5 ml of hydrochloric isopropanol was added, resulting in the crystallization of a composite. The composite was drained on a number 4 frit and then washed with isopropanol several times. The composite was then dried under vacuum at 40° C. in the presence of $P_2O_5$. 0.714 g of beige solid corresponding to the expected composition was obtained.

The NMR analyses ($^1H$ 400 MHz and $^{13}C$ 100.61 MHz DMSO $d_6$) were in accordance with the expected structure.

The expected molecular ion $M^+$ $[C_{13}H_{15}N_6O_2]^+$ was principally detected.

Synthesis of the chlorine chlorhydrate of 1-{2-[(3-aminopyrazolo[1,5-a]pyridin-2-yl)amino]ethyl}-3-methyl-1H-imidazol-3-ium

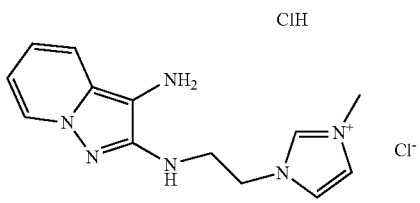

100 ml of ethanol and 3.25 g of zinc were introduced into a 250 ml three necked flask equipped with a bulb condensor, a thermometer and a magnetic stirrer and refluxed. 5 drops of acetic acid were then added. A solution of 3.25 g of the chloride of 3-methyl-1-{2-[(3-nitropyrazolo[1,5-a]pyridin-2-yl)amino]ethyl}-1H-imidazol-3-ium, 10 ml ethanol ml, and 4 ml water was added drop by drop over 30 minutes and the reflux was maintained for 24 hours. When the reduction was finished, zinc was filtered from the solution on a bed of Celite. The remaining solution was recovered in 70 ml of hydrochloric isopropanol that was previously cooled by a bath dry ice. The zinc was washed with ethanol. The remaining solution was concentrated to 1/3 and cooled to zero ° C., resulting in the crystallization of a clear gray solid. The clear gray solid was drained on a number 3 frit and dried under vacuum in the presence of $P_2O_5$. 2.85 g of a clear gray powder corresponding to the expected composition was obtained.

The NMR analyses ($^1H$ 400 MHz and $^{13}C$ 100.61 MHz DMSO $d_6$) were in accordance with the expected structure.

The expected molecular ion $M^+$ $[C_{13}H_{17}N_6]$ was principally detected.

Examples of Dyeing

The following dyeing compositions were prepared:

|  | Example | | |
|---|---|---|---|
|  | 1' | 2' | 3' |
| 2-[(3-aminopyrazolo[1,5-a]pyridin-2-yl)amino]-N,N,N-trimethylethanaminium chloride hydrochloride | $10^{-3}$ mol | $10^{-3}$ mol | $10^{-3}$ mol |
| 5-Amino-2-methyl-phenol | $10^{-3}$ mol |  |  |
| 2-(2,4-Diamino-phenoxy)-ethanol, hydrochloride |  | $10^{-3}$ mol |  |
| 3-Amino-2-chloro-6-methyl-phenol, hydrochloride |  |  | $10^{-3}$ mol |
| Dyeing support (2)** | (*) | (*) | (*) |
| Demineralized water q.s.f. | 100 g | 100 g | 100 g |
| Shade observed | reddish brown | greyish green-blue | greyish violet |

|  | Example | | | |
|---|---|---|---|---|
|  | 1" | 2" | 3" | 4" |
| 2-[(3-aminopyrazolo[1,5-a]pyridin-2-yl)amino]-N,N,N-trimethylethanaminium chloride hydrochloride | $10^{-3}$ mol | $10^{-3}$ mol | $10^{-3}$ mol | $10^{-3}$ mol |
| 5-Amino-2-methyl-phenol | $10^{-3}$ mol |  |  |  |
| 1H-Indol-6-ol |  | $10^{-3}$ mol |  |  |
| 2-(2,4-Diamino-phenoxy)-ethanol, hydrochloride |  |  | $10^{-3}$ mol |  |
| 3-Amino-2-chloro-6-methyl-phenol, hydrochloride |  |  |  | $10^{-3}$ mol |
| Dyeing support (1)* | (*) | (*) | (*) | (*) |
| Demineralized water q.s.f. | 100 g | 100 g | 100 g | 100 g |
| Shade observed | bright violet | orange-brown | bright blue | bright violet-blue |

|  | Example | | |
|---|---|---|---|
|  | A | B | C |
| 1-{3-[(3-aminopyrazolo[1,5-a]pyridin-2-yl)amino]propyl}-3-methyl-1H-imidazol-3-ium chloride hydrochloride | $10^{-3}$ mol | $10^{-3}$ mol | $10^{-3}$ mol |
| 5-Amino-2-methyl-phenol | $10^{-3}$ mol |  |  |
| 2-(2,4-Diamino-phenoxy)-ethanol, hydrochloride |  | $10^{-3}$ mol |  |
| 3-Amino-2-chloro-6-methyl-phenol, hydrochloride |  |  | $10^{-3}$ mol |
| Dyeing support (2)** | (*) | (*) | (*) |
| Demineralized water q.s.f. | 100 g | 100 g | 100 g |
| Shade observed | greyish green-blue | bright blue-green | chromatic blue-green |

|  | Example | | |
|---|---|---|---|
|  | A' | B' | C' |
| 1-{3-[(3-aminopyrazolo[1,5-a]pyridin-2-yl)amino]propyl}-3-methyl-1H-imidazol-3-ium chloride hydrochloride | $10^{-3}$ mol | $10^{-3}$ mol | $10^{-3}$ mol |
| 5-Amino-2-methyl-phenol | $10^{-3}$ mol |  |  |
| 2-(2,4-Diamino-phenoxy)-ethanol, hydrochloride |  | $10^{-3}$ mol |  |
| 3-Amino-2-chloro-6-methyl-phenol, hydrochloride |  |  | $10^{-3}$ mol |
| Dyeing support (1)* | (*) | (*) | (*) |
| Demineralized water q.s.f. | 100 g | 100 g | 100 g |
| Shade observed | chromatic blue | blue-green | chromatic blue |

-continued

| | Example | | |
|---|---|---|---|
| | D | E | F |
| 3-[(3-aminopyrazolo[1,5-a]pyridin-2-yl)amino]-N,N,N-trimethylpropan-1-aminium chloride hydrochloride | $10^{-3}$ mol | $10^{-3}$ mol | $10^{-3}$ mol |
| 5-Amino-2-methyl-phenol | $10^{-3}$ mol | | |
| 2-(2,4-Diamino-phenoxy)-ethanol, hydrochloride | | $10^{-3}$ mol | |
| 3-Amino-2-chloro-6-methyl-phenol, hydrochloride | | | $10^{-3}$ mol |
| Dyeing support (2)** | (*) | (*) | (*) |
| Demineralized water q.s.f. | 100 g | 100 g | 100 g |
| Shade observed | greyish blue | bright blue-green | chromatic blue |

| | Example | | |
|---|---|---|---|
| | A″ | B″ | C″ |
| 1-{3-[(3-aminopyrazolo[1,5-a]pyridin-2-yl)amino]propyl}-3-methyl-1H-imidazol-3-ium chloride hydrochloride | $10^{-3}$ mol | $10^{-3}$ mol | $10^{-3}$ mol |
| 5-Amino-2-methyl-phenol | $10^{-3}$ mol | | |
| 2-(2,4-Diamino-phenoxy)-ethanol, hydrochloride | | $10^{-3}$ mol | |
| 3-Amino-2-chloro-6-methyl-phenol, hydrochloride | | | $10^{-3}$ mol |
| Dyeing support (1)* | (*) | (*) | (*) |
| Demineralized water q.s.f. | 100 g | 100 g | 100 g |
| Shade observed | blue | blue-green | chromatic blue |

| | Example | | | |
|---|---|---|---|---|
| | G | H | J | K |
| 1-{2-[(3-aminopyrazolo[1,5-a]pyridin-2-yl)amino]ethyl}-1-methylpiperidinium chloride hydrochloride | $10^{-3}$ mol | $10^{-3}$ mol | $10^{-3}$ mol | $10^{-3}$ mol |
| 5-Amino-2-methyl-phenol | $10^{-3}$ mol | | | |
| 1H-Indol-6-ol | | $10^{-3}$ mol | | |
| 2-(2,4-Diamino-phenoxy)-ethanol, hydrochloride | | | $10^{-3}$ mol | |
| 3-Amino-2-chloro-6-methyl-phenol, hydrochloride | | | | $10^{-3}$ mol |
| Dyeing support (2)** | (*) | (*) | (*) | (*) |
| Demineralized water q.s.f. | 100 g | 100 g | 100 g | 100 g |
| Shade observed | bright violet-blue | yellow | bright chromatic blue | bright chromatic violet-blue |

-continued

|  | Example | | |
|---|---|---|---|
|  | G' | H' | J' |
| 1-{2-[(3-aminopyrazolo[1,5-a]pyridin-2-yl)amino]ethyl}-1-methylpiperidinium chloride hydrochloride | $10^{-3}$ mol | $10^{-3}$ mol | $10^{-3}$ mol |
| 5-Amino-2-methyl-phenol | $10^{-3}$ mol |  |  |
| 2-(2,4-Diamino-phenoxy)-ethanol, hydrochloride |  | $10^{-3}$ mol |  |
| 3-Amino-2-chloro-6-methyl-phenol, hydrochloride |  |  | $10^{-3}$ mol |
| Dyeing support (1)* | (*) | (*) | (*) |
| Demineralized water q.s.f. | 100 g | 100 g | 100 g |
| Shade observed | bright chromatic violet-blue | bright chromatic blue | bright chromatic violet-blue |

(*): dyeing support (1) pH 7
[A.S. = active substance]

| Ethanol, 96° | 20.8 g |
|---|---|
| Sodium metabisulphite, 35% aqueous solution | 0.23 g A.S. |
| Pentasodium salt of diethylenetriamine-pentaacetic acid, 40% aqueous solution | 0.48 g A.S. |
| $C_8$–$C_{10}$ alkyl polyglucoside, 60% aqueous solution | 3.6 g A.S. |
| Benzyl alcohol | 2.0 g |
| Polyethylene glycol with 8 units of ethylene oxide | 3.0 g |
| $Na_2HPO_4$ | 0.28 g |
| $KH_2PO_4$ | 0.46 g |

(**): dyeing support (2) pH 9.5

| Ethanol, 96° | 20.8 g |
|---|---|
| Sodium metabisulphite, 35% aqueous solution | 0.23 g A.S. |
| Pentasodium salt of diethylenetriamine-pentaacetic acid, 40% aqueous solution | 0.48 g A.S. |
| $C_8$–$C_{10}$ alkyl polyglucoside, 60% aqueous solution | 3.6 g A.S. |
| Benzyl alcohol | 2.0 g |
| Polyethylene glycol with 8 units of ethylene oxide | 3.0 g |
| $NH_4Cl$ | 4.32 g |
| Ammonia, 20% $NH_3$ | 2.94 g |

At the moment of use, each composition was mixed with an equal weight of hydrogen peroxide solution at 20 volumes (6 wt. %). A final pH of 7, or of 9.5, respectively, was obtained.

Each mixture obtained was applied to locks of grey hair with 90% white. After a waiting time of 30 minutes, the locks of hair were rinsed, washed with a standard shampoo, rinsed again and then dried. The results obtained are presented in the tables given above.

What is claimed is:

1. A composition for dyeing keratin fibers comprising, in a suitable dyeing medium, at least one oxidation dyeing base chosen from 3-amino pyrazolo-[1,5-a]-pyridine derivatives of formula (I) as well as its salts and solvates:

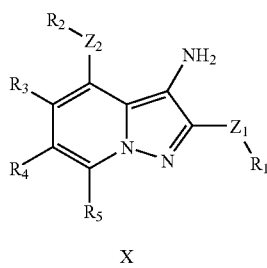

in which
$Z_1$ and $Z_2$, which may be the same or different, are independently chosen from:
a single covalent bond,
a divalent radical chosen from:
an oxygen atom,
a radical —$NR_6(R_7)_p$—, where p is 0 or 1; wherein
when p is equal to 0, $R_6$ is chosen from a hydrogen atom and $C_1$-$C_6$ alkyl radicals, or $R_6$ together with at least one of $R_1$ and $R_2$ form, together with the nitrogen atom to which they are attached, a substituted or unsubstituted, saturated or unsaturated, aromatic or non-aromatic heterocycle comprising 5 to 8 ring members, wherein said heterocycle may optionally comprise at least one heteroatom or group chosen from N, O, S, $SO_2$, —CO—, and may be cationic and/or substituted with a cationic or non-cationic radical;
when p is equal to 1, —$NR_6R_7$— is a cationic radical in which $R_6$ and $R_7$ may be the same or different, and are independently chosen from alkyl radicals; and
when $R_1$ is a methyl radical, $Z_1$ may also be chosen from a divalent radical —S—, —SO— and —$SO_2$—;
with the proviso that at least one of $Z_1$ and $Z_2$ is not a single covalent bond;
$R_1$ and $R_2$, which may be the same or different, are independently chosen from:
a hydrogen atom
$C_1$-$C_{10}$ alkyl radicals, optionally substituted and optionally interrupted by at least one heteroatom or group chosen from O, N, Si, S, SO, $SO_2$,
$C_1$-$C_{10}$ alkyl radicals substituted and/or interrupted by a cationic radical, a halogen atom,
an SO₃H radical,
a ring with 5 to 8 ring members, wherein said ring may be substituted or unsubstituted, saturated, unsaturated or aromatic, and may contain at least one heteroatom or group chosen from N, O, S, SO₂, —CO—, and said ring can be cationic and/or substituted with a cationic radical; and when $Z_1$ or $Z_2$ is a covalent bond, $R_1$ or $R_2$ respectively may also be a radical chosen from:
optionally substituted $C_1$-$C_6$ alkylcarbonyls; and
—O—CO—R, —CO—O—R, NR—CO—R' or —CO—NRR' in which R and R' may be the same or different, and are independently chosen from a hydrogen atom and optionally substituted $C_1$-$C_6$ alkyl radicals;

$R_3$, $R_4$ and $R_5$, which may be the same or different, are independently chosen from:
a hydrogen atom;
a hydroxyl radical;
a $C_1$-$C_6$ alkoxy radical;
a $C_1$-$C_6$ alkylthio radical;
an amino radical;
a monoalkylamino radical;
a $C_1$-$C_6$ dialkylamino radical, in which the alkyl radicals can form, together with the nitrogen atom to which they are attached, a heterocycle comprising 5 to 8 ring members, wherein said heterocycle may be saturated or unsaturated, aromatic or non-aromatic, and may contain at least one heteroatom or group chosen from N, O, S, SO₂, CO, and said heterocycle may be cationic, and/or substituted with a cationic radical;
an optionally substituted $C_1$-$C_6$ alkylcarbonyl radical;
a radical —O—CO—R, —CO—O—R, NR—CO—R' or —CO—NRR', in which R and R' may be the same or different, and are independently chosen from a hydrogen atom and optionally substituted $C_1$-$C_6$ alkyl radicals;
a halogen atom;
a radical —NHSO₃H,
an optionally substituted $C_1$-$C_4$ alkyl radical;
an optionally substituted, saturated, unsaturated or aromatic carbon ring; and
any two of $R_3$, $R_4$ and $R_5$, can form a saturated or unsaturated ring;
X is chosen from at least one anion that can ensure the electronegativity of the derivative of formula (I),
with the proviso that at least one of the groups $Z_1$, $R_1$, $Z_2$, $R_2$ is a cationic radical.

2. The composition of claim 1, in which $Z_1$ and/or $Z_2$ are chosen from a single bond, a radical —O—, a radical —NR₆— in which $R_6$ is chosen from a hydrogen atom, an alkyl radical, or $R_6$ forms, together with at least one of $R_1$ and $R_2$, a heterocycle that is cationic and/or is substituted with a cationic radical.

3. The composition of claim 1, wherein $R_6$ forms, together with at least one of $R_1$ and $R_2$, a cationic heterocycle or a heterocycle substituted with a cationic radical.

4. The composition of claim 2, where $R_6$ forms, together with at least one of $R_1$ and $R_2$, an imidazole substituted with a quaternary ammonium radical or an imidazolium, a piperazine substituted with a quaternary ammonium radical or a piperazinium, a pyrrolidine substituted with a quaternary ammonium radical or a pyrrolidinium, a diazepane substituted with a quaternary ammonium radical or a diazepanium.

5. The composition of claim 1, wherein $R_1$ and $R_2$, which may be the same or different, are indpendently chosen from a hydrogen atom and alkyl radicals which can be interrupted or substituted with a cationic radical.

6. The composition of claim 1, wherein the radicals $R_3$, $R_4$ and $R_5$, which may be the same or different, are independently chosen from a hydrogen atom and optionally substituted $C_1$-$C_4$ alkyl radicals.

7. The composition of claim 1 wherein the at least one compound of formula (I) is chosen from those of formula (I'):

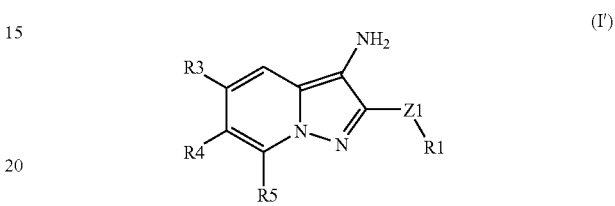

in which $Z_1$, $R_1$, $R_3$, $R_4$ and $R_5$ are as defined in claim 1.

8. The composition of claim 7, wherein $Z_1$ is chosen from —NH— or NR₆, where $R_6$ forms, together with $R_1$, a cationic heterocycle or a heterocycle substituted with a cationic radical.

9. The composition of claim 1, where the at least one compound of formula (I) is chosen from:

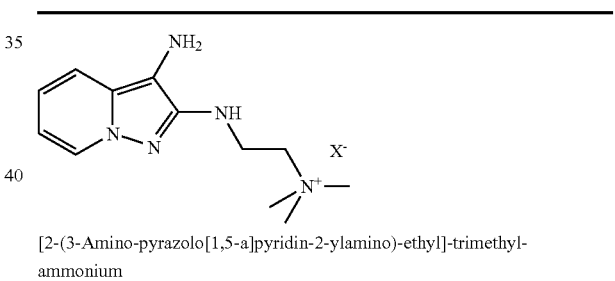

[2-(3-Amino-pyrazolo[1,5-a]pyridin-2-ylamino)-ethyl]-trimethyl-ammonium

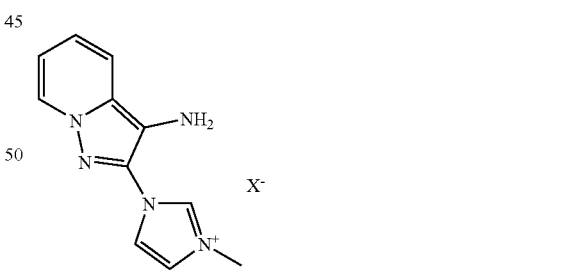

3-(3-Amino-pyrazolo[1,5-a]pyridin-2-yl)-1-methyl-3H-imidazol-1-ium

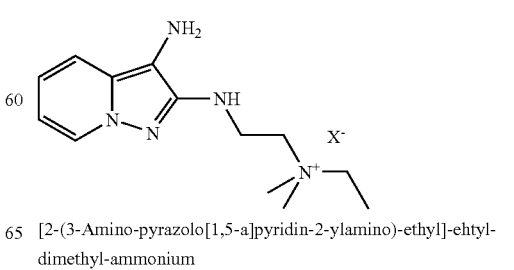

[2-(3-Amino-pyrazolo[1,5-a]pyridin-2-ylamino)-ethyl]-ehtyl-dimethyl-ammonium

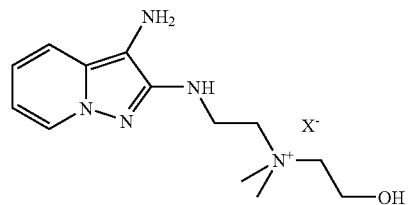

[2-(3-Amino-pyrazolo[1,5-a]pyridin-2-ylamino)-ethyl]-(2-hydroxy-ethyl)-dimethyl-ammonium

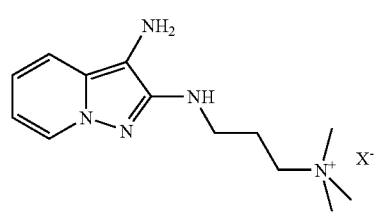

[3-(3-Amino-pyrazolo[1,5-a]pyridin-2-ylamino)-propyl]-trimethyl-ammonium

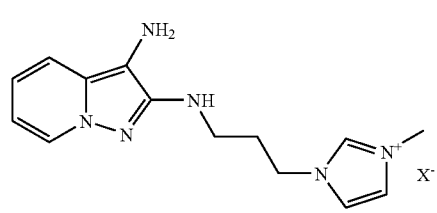

3-[3-(3-Amino-pyrazolo[1,5-a]pyridin-2-ylamino)-propyl]-1-methyl-3H-imidazol-1-ium

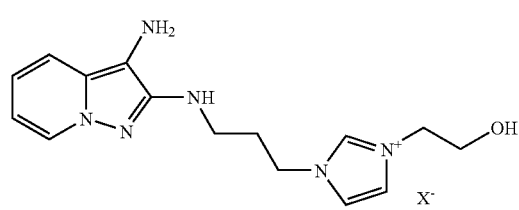

3-[3-(3-Amino-pyrazolo[1,5-a]pyridin-2-ylamino)-propyl]-1-(2-hydroxy-ethyl)-3H-imidazol-1-ium

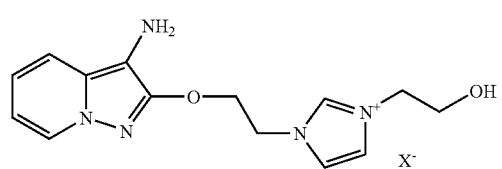

3-[2-(3-Amino-pyrazolo[1,5-a]pyridin-2-yloxy)-ethyl]-1-(2-hydroxy-ethyl)-3H-imidazol-1-ium

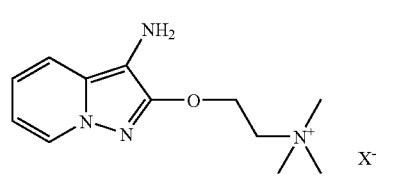

2-[(3-aminopyrazolo[1,5-a]pyridin-2-yl)oxy]-N,N,N-trimethylethanaminium

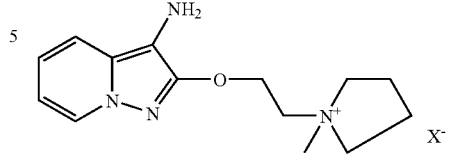

1-{2-[(3-aminopyrazolo[1,5-a]pyridin-2-yl)oxy]ethyl}-1-methylpyrrolidinium

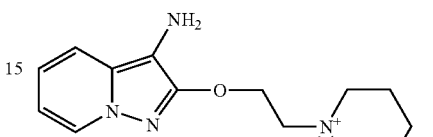

1-{2-[(3-aminopyrazolo[1,5-a]pyridin-2-yl)oxy]ethyl}-1-methylpiperidinium

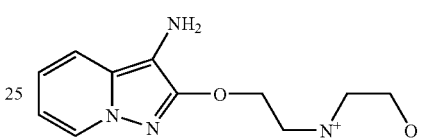

4-{2-[(3-aminopyrazolo[1,5-a]pyridin-2-yl)oxy]ethyl}-4-methylmorpholin-4-ium

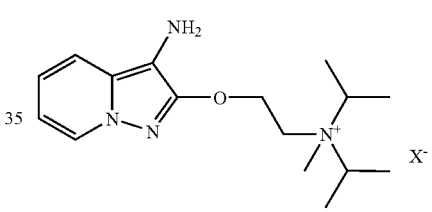

N-{2-[(3-aminopyrazolo[1,5-a]pyridin-2-yl)oxy]ethyl}-N-isopropyl-N-methylpropan-2-aminium

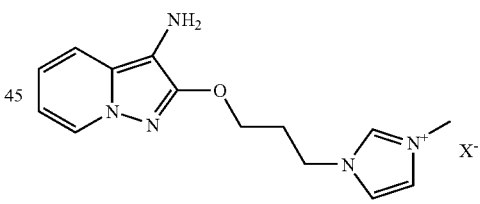

3-[3-(3-Amino-pyrazolo[1,5-a]pyridin-2-yloxy)-propyl]-1-methyl-3H-imidazol-1-ium

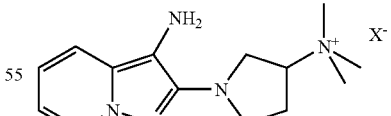

[1-(3-Amino-pyrazolo[1,5-a]pyridin-2-yl)-pyrrolidin-3-yl]trimethyl-ammonium

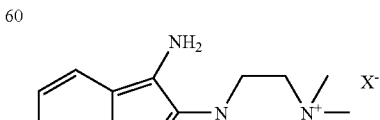

4-(3-Amino-pyrazolo[1,5-a]pyridin-2-yl)-1,1-dimethyl-piperazin-1-ium

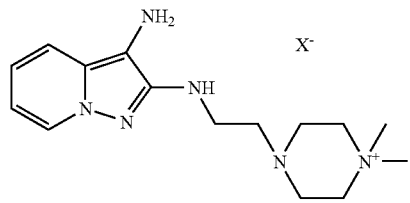

4-[2-(3-Amino-pyrazolo[1,5-a]pyridin-2-ylamino)-ethyl]-1,1-dimethyl-piperazin-1-ium

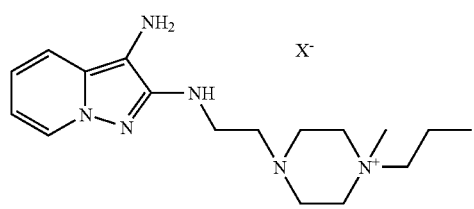

4-[2-(3-Amino-pyrazolo[1,5-a]pyridin-2-ylamino)-ethyl]-1-methyl-1-propyl-piperazin-1-ium

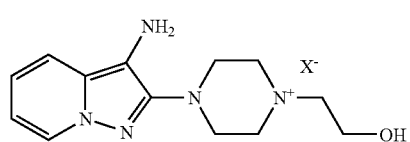

4-(3-Amino-pyrazolo[1,5-a]pyridin-2-yl)-1-(2-hydroxy-ethyl)-piperazin-1-ium

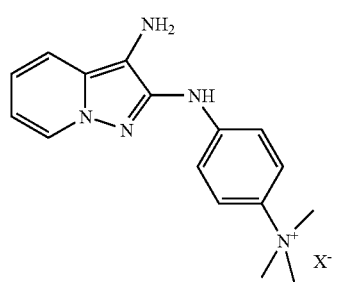

[4-(3-Amino-pyrazolo[1,5-a]pyridin-2-ylamino)-phenyl]-trimethyl-ammonium

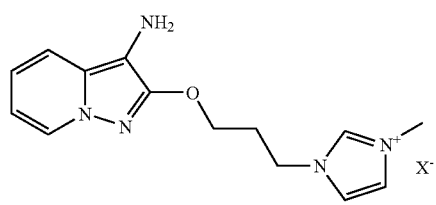

3-[3-(3-Amino-pyrazolo[1,5-a]pyridin-2-yloxy)-propyl]-1-methyl-3H-imidazol-1-ium

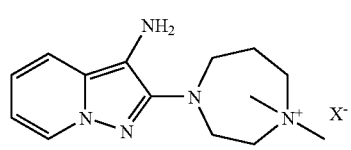

4-(3-Amino-pyrazolo[1,5-a]pyridin-2-yl)-1,1-dimethyl-[1,4]diazepan-1-ium

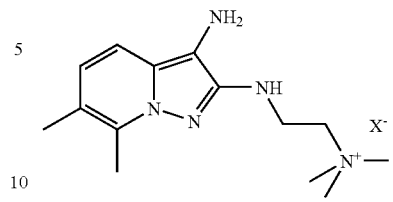

[2-(3-Amino-6,7-dimethyl-pyrazolo[1,5-a]pyridin-2-ylamino)-ethyl]-trimethyl-ammonium

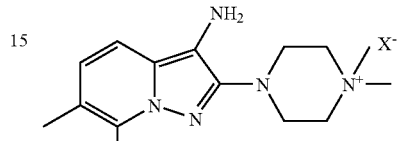

4-(3-Amino-6,7-dimethyl-pyrazolo[1,5-a]pyridin-2-yl)-1,1-dimethyl-piperazin-1-ium

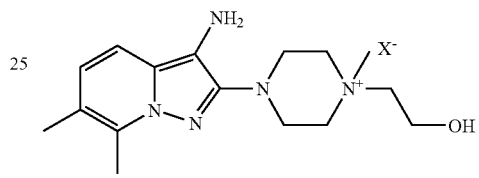

4-(3-Amino-6,7-dimethyl-pyrazolo[1,5-a]pyridin-2-yl)-1-(2-hydroxy-ethyl)-1-methyl-piperazin-1-ium

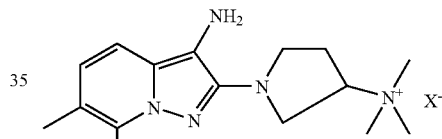

[1-(3-Amino-6,7-dimethyl-pyrazolo[1,5-a]pyridin-2-yl)-pyrrolidin-3-yl]-trimethyl-ammonium

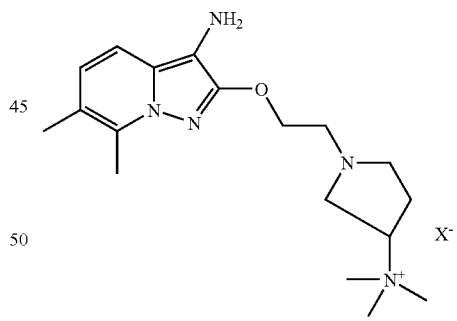

{1-[2-(3-Amino-6,7-dimethyl-pyrazolo[1,5-a]pyridin-2-yloxy)-ethyl]-pyrrolidin-3-yl}-trimethyl-ammonium

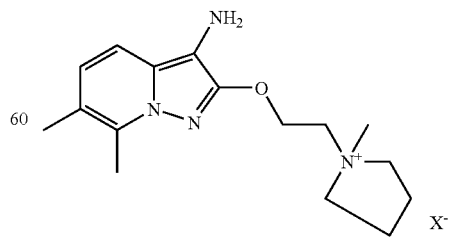

1-{2-[(3-amino-6,7-dimethylpyrazolo[1,5-a]pyridin-2-yl)oxy]ethyl}-1-methylpyrrolidinium

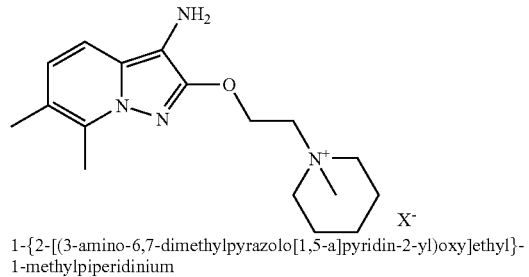

1-{2-[(3-amino-6,7-dimethylpyrazolo[1,5-a]pyridin-2-yl)oxy]ethyl}-1-methylpiperidinium

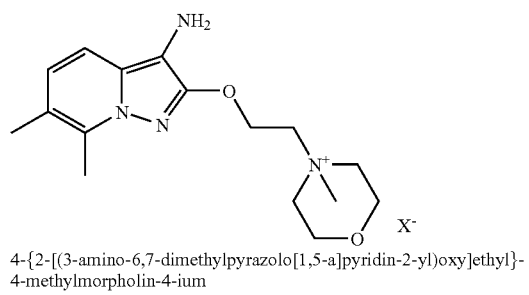

4-{2-[(3-amino-6,7-dimethylpyrazolo[1,5-a]pyridin-2-yl)oxy]ethyl}-4-methylmorpholin-4-ium

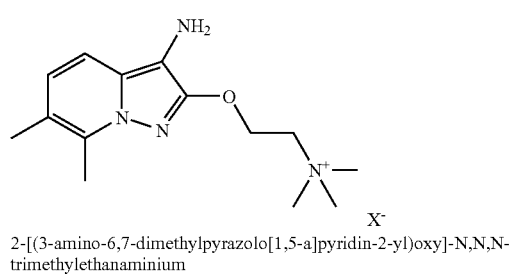

2-[(3-amino-6,7-dimethylpyrazolo[1,5-a]pyridin-2-yl)oxy]-N,N,N-trimethylethanaminium

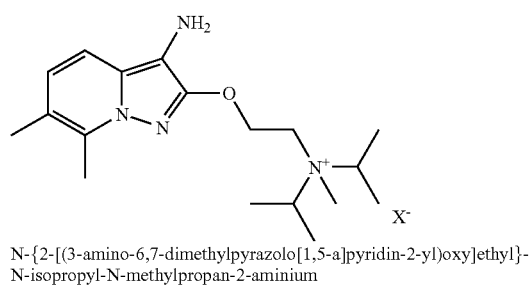

N-{2-[(3-amino-6,7-dimethylpyrazolo[1,5-a]pyridin-2-yl)oxy]ethyl}-N-isopropyl-N-methylpropan-2-aminium

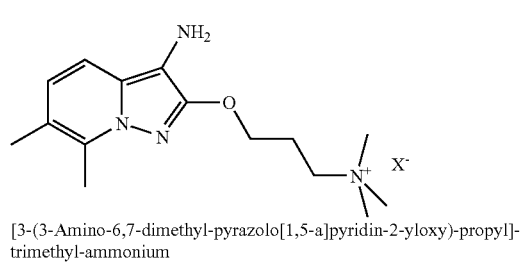

[3-(3-Amino-6,7-dimethyl-pyrazolo[1,5-a]pyridin-2-yloxy)-propyl]-trimethyl-ammonium

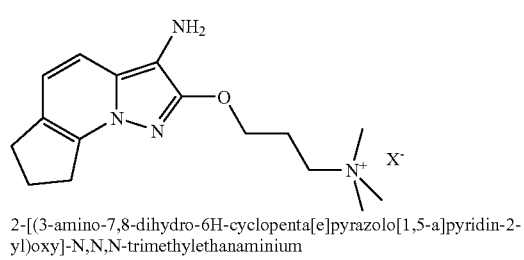

2-[(3-amino-7,8-dihydro-6H-cyclopenta[e]pyrazolo[1,5-a]pyridin-2-yl)oxy]-N,N,N-trimethylethanaminium

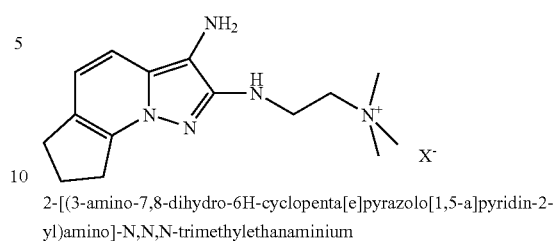

2-[(3-amino-7,8-dihydro-6H-cyclopenta[e]pyrazolo[1,5-a]pyridin-2-yl)amino]-N,N,N-trimethylethanaminium

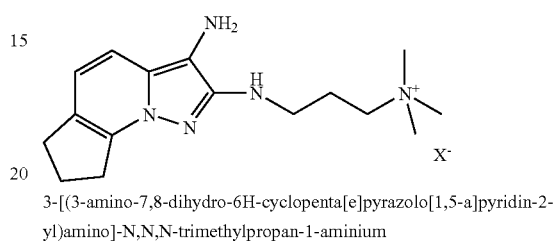

3-[(3-amino-7,8-dihydro-6H-cyclopenta[e]pyrazolo[1,5-a]pyridin-2-yl)amino]-N,N,N-trimethylpropan-1-aminium

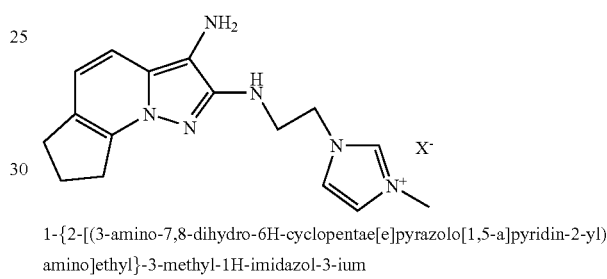

1-{2-[(3-amino-7,8-dihydro-6H-cyclopentae[e]pyrazolo[1,5-a]pyridin-2-yl)amino]ethyl}-3-methyl-1H-imidazol-3-ium

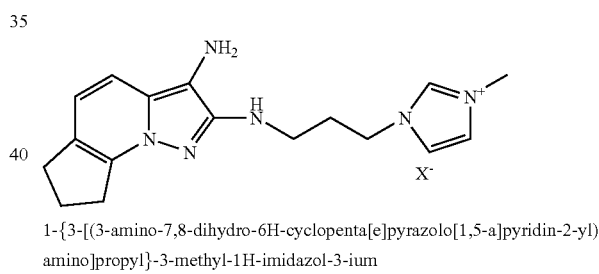

1-{3-[(3-amino-7,8-dihydro-6H-cyclopenta[e]pyrazolo[1,5-a]pyridin-2-yl)amino]propyl}-3-methyl-1H-imidazol-3-ium

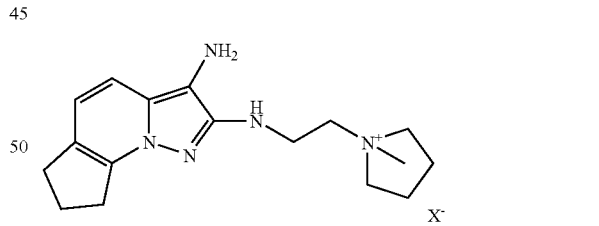

1-{2-[(3-amino-7,8-dihydro-6H-cyclopenta[e]pyrazolo[1,5-a]pyridin-2-yl)amino]ethyl}-1-methylpyrrolidinium

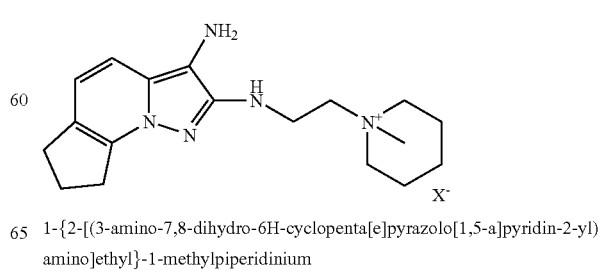

1-{2-[(3-amino-7,8-dihydro-6H-cyclopenta[e]pyrazolo[1,5-a]pyridin-2-yl)amino]ethyl}-1-methylpiperidinium -continued

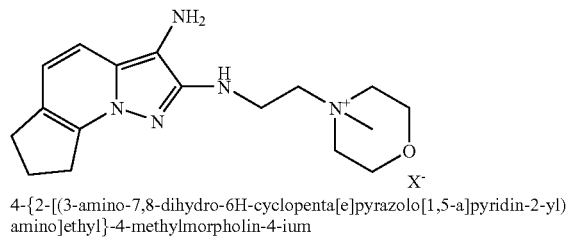

4-{2-[(3-amino-7,8-dihydro-6H-cyclopenta[e]pyrazolo[1,5-a]pyridin-2-yl)amino]ethyl}-4-methylmorpholin-4-ium

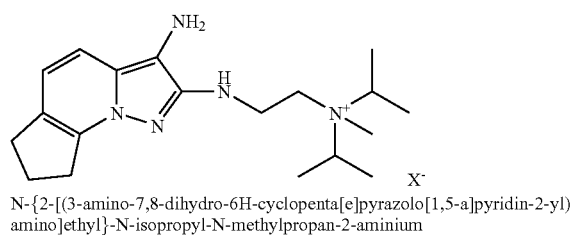

N-{2-[(3-amino-7,8-dihydro-6H-cyclopenta[e]pyrazolo[1,5-a]pyridin-2-yl)amino]ethyl}-N-isopropyl-N-methylpropan-2-aminium

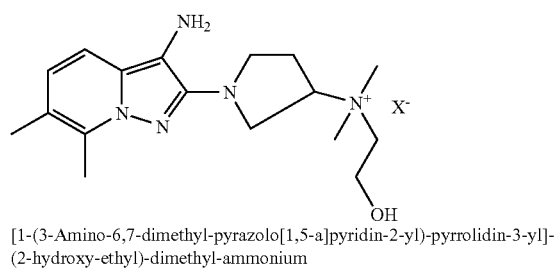

[1-(3-Amino-6,7-dimethyl-pyrazolo[1,5-a]pyridin-2-yl)-pyrrolidin-3-yl]-(2-hydroxy-ethyl)-dimethyl-ammonium

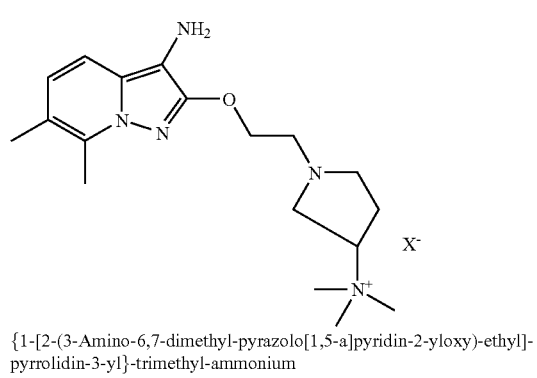

{1-[2-(3-Amino-6,7-dimethyl-pyrazolo[1,5-a]pyridin-2-yloxy)-ethyl]-pyrrolidin-3-yl}-trimethyl-ammonium

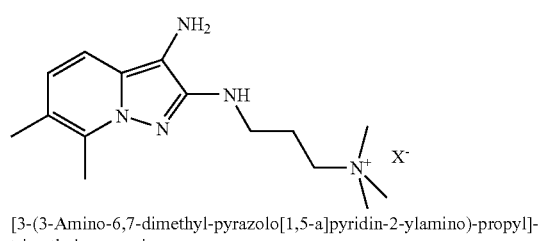

[3-(3-Amino-6,7-dimethyl-pyrazolo[1,5-a]pyridin-2-ylamino)-propyl]-trimethyl-ammonium

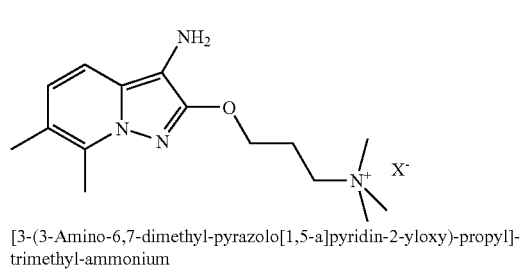

[3-(3-Amino-6,7-dimethyl-pyrazolo[1,5-a]pyridin-2-yloxy)-propyl]-trimethyl-ammonium -continued

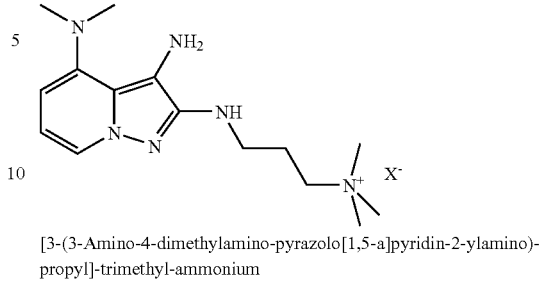

[3-(3-Amino-4-dimethylamino-pyrazolo[1,5-a]pyridin-2-ylamino)-propyl]-trimethyl-ammonium

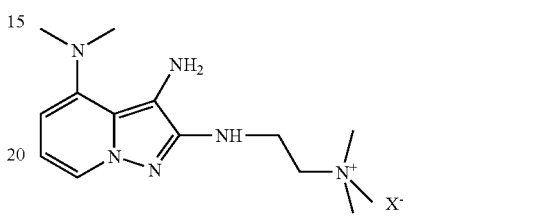

[2-(3-Amino-4-dimethylamino-pyrazolo[1,5-a]pyridin-2-ylamino)-ethyl]-trimethyl-ammonium

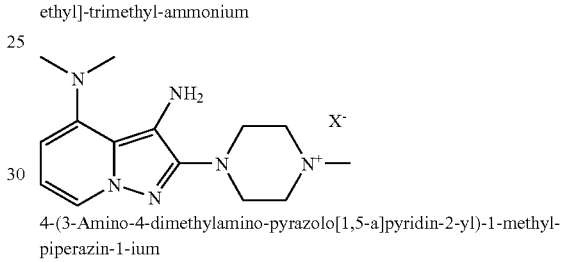

4-(3-Amino-4-dimethylamino-pyrazolo[1,5-a]pyridin-2-yl)-1-methyl-piperazin-1-ium

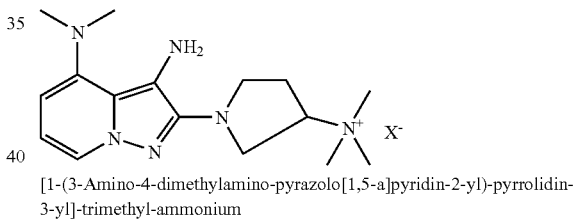

[1-(3-Amino-4-dimethylamino-pyrazolo[1,5-a]pyridin-2-yl)-pyrrolidin-3-yl]-trimethyl-ammonium

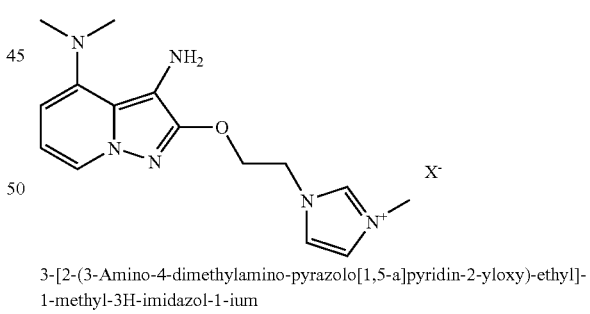

3-[2-(3-Amino-4-dimethylamino-pyrazolo[1,5-a]pyridin-2-yloxy)-ethyl]-1-methyl-3H-imidazol-1-ium

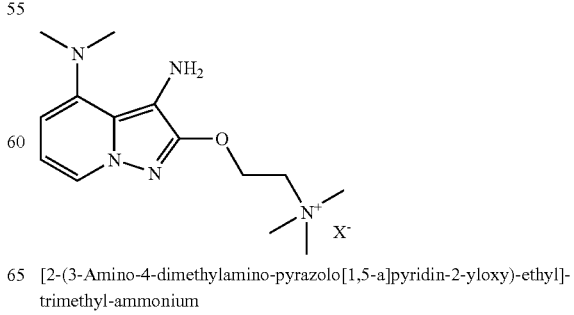

[2-(3-Amino-4-dimethylamino-pyrazolo[1,5-a]pyridin-2-yloxy)-ethyl]-trimethyl-ammonium -continued

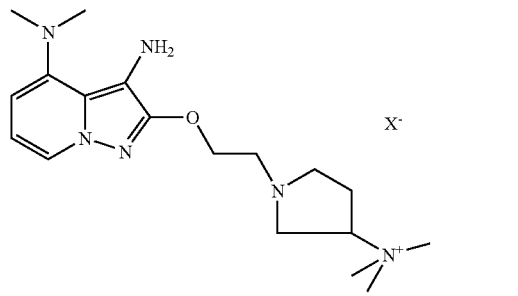

{1-[2-(3-Amino-4-dimethylamino-pyrazolo[1,5-a]pyridin-2-yloxy)-ethyl]-pyrrolidin-3-yl}-trimethyl-ammonium

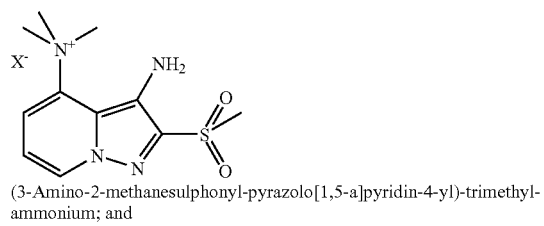

(3-Amino-2-methanesulphonyl-pyrazolo[1,5-a]pyridin-4-yl)-trimethyl-ammonium; and

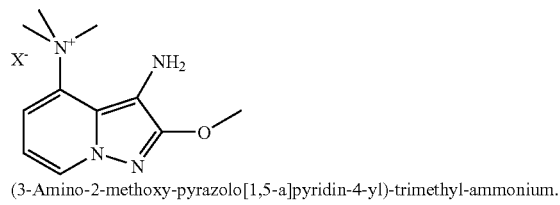

(3-Amino-2-methoxy-pyrazolo[1,5-a]pyridin-4-yl)-trimethyl-ammonium.

10. The composition of claim 8, wherein $Z_1$ is equal to —NH— and $R_1$ is a cationic radical, or $Z_1$ is equal to —O— and $R_1$ is a cationic radical.

11. The composition of claim 1, wherein the at least one oxidation base of formula (I) is present in the composition, in an amount for each base, ranging from 0.001% to 10% by weight, relative to the total weight of the dyeing composition.

12. The composition of claim 1, further comprising at least one coupler chosen from meta-phenylenediamines, meta-aminophenols, meta-diphenols, naphthalenic couplers, heterocyclic couplers, and the addition salts thereof.

13. The composition of claim 12, wherein the at least one coupler is present in the composition, in an amount for each coupler, ranging from 0.001% to 10% by weight, relative to the total weight of the dyeing composition.

14. A method for dyeing keratin fibers, comprising
applying to the keratin fibers a dye composition comprising, in a suitable dyeing medium, at least one oxidation dyeing base chosen from 3-amino pyrazolo-[1,5-a]-pyridine derivatives of formula (I) as well as its salts and solvates:

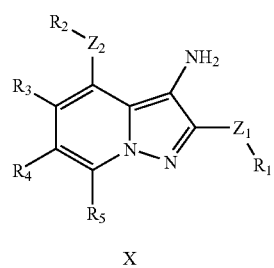

(I)

in which
$Z_1$ and $Z_2$, which may be the same or different, are independently chosen from:
a single-covalent bond,
a divalent radical chosen from:
an oxygen atom,
a radical —$NR_6(R_7)_p$—, where p is 0 or 1; wherein
when p is equal to 0, $R_6$ is chosen from a hydrogen atom and $C_1$-$C_6$ alkyl radicals, or $R_6$ together with at least one of $R_1$ and $R_2$ form, together with the nitrogen atom to which they are attached, a substituted or unsubstituted, saturated or unsaturated, aromatic or non-aromatic heterocycle comprising 5 to 8 ring members, wherein said heterocycle can optionally comprise at least one heteroatom or group chosen from N, O, S, $SO_2$, —CO—, and may be cationic and/or substituted with a cationic or non-cationic radical;
when p is equal to 1, —$NR_6R_7$— is a cationic radical in which $R_6$ and $R_7$ may be the same or different, and are independently chosen from alkyl radicals; and
when $R_1$ is a methyl radical, $Z_1$ can also be chosen from a divalent radical —S—, —SO— and —$SO_2$—;
with the proviso that at least one of $Z_1$ and $Z_2$ is not a single covalent bond;
$R_1$ and $R_2$, which may be the same or different, are independently chosen from:
a hydrogen atom
$C_1$-$C_{10}$ alkyl radicals, optionally substituted and optionally interrupted by at least one heteroatom or a group chosen from O, N, Si, S, SO, $SO_2$,
$C_1$-$C_{10}$ alkyl radicals substituted and/or interrupted by a cationic radical,
a halogen atom,
an $SO_3H$ radical,
a ring with 5 to 8 ring members, wherein said ring may be substituted or unsubstituted, saturated, unsaturated or aromatic, and can contain at least one heteroatom or group chosen from N, O, S, $SO_2$, —CO—, and said ring can be cationic and/or substituted with a cationic radical; and
when $Z_1$ or $Z_2$ is a covalent bond, $R_1$ or $R_2$ respectively may also be a radical chosen from:
optionally substituted $C_1$-$C_6$ alkylcarbonyls; and
—O—CO—R, —CO—O—R, NR—CO—R' or —CO—NRR' in which R and R' may be the same or different, and are independently chosen from a hydrogen atom and optionally substituted $C_1$-$C_6$ alkyl radicals;
$R_3$, $R_4$ and $R_5$, which may be the same or different, are independently chosen from:
a hydrogen atom;
a hydroxyl radical;
a $C_1$-$C_6$ alkoxy radical;
a $C_1$-$C_6$ alkylthio radical;
an amino radical;
a monoalkylamino radical;
a $C_1$-$C_6$ dialkylamino radical, in which the alkyl radicals can form, together with the nitrogen atom to which they are attached, a heterocycle comprising 5 to 8 ring members, wherein said heterocycle may be saturated or unsaturated, aromatic or non-aromatic, and may contain at least one heteroatom or group chosen from N, O, S, $SO_2$, CO, and said heterocycle can be cationic, and/or substituted with a cationic radical;
an optionally substituted $C_1$-$C_6$ alkylcarbonyl radical;

a radical —O—CO—R, —CO—O—R, NR—CO—R' or —CO—NRR', in which R and R' may be the same or different, and are independently chosen from a hydrogen atom and optionally substituted $C_1$-$C_6$ alkyl radicals;

a halogen atom;

a radical —NHSO$_3$H, an optionally substituted $C_1$-$C_4$ alkyl radical;

an optionally substituted, saturated, unsaturated or aromatic carbon ring; and any two of $R_3$, $R_4$ and $R_5$, may form a saturated or unsaturated ring;

X is chosen from at least one anion that can ensure the electronegativity of the derivative of formula (I), with the proviso that at least one of the groups $Z_1$, $R_1$, $Z_2$, $R_2$ is a cationic radical; and wherein said composition is applied to the keratin fibers in the presence of at least one oxidizing agent for a period of time that is sufficient to develop the desired coloration.

15. The method of claim 14, wherein the at least one oxidizing agent is chosen from hydrogen peroxide, urea peroxide, alkali metal bromates, per-salts, per-acids and oxidase enzymes.

16. A multi-compartment kit comprising at least one first compartment containing a composition for dyeing keratin fibers comprising, in a suitable dyeing medium, at least one oxidation dyeing base chosen from 3-amino pyrazolo-[1,5-a]-pyridine derivatives of formula (I) as well as its salts and solvates:

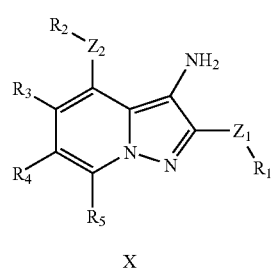

(I)

in which $Z_1$ and $Z_2$, which may be the same or different, are independently chosen from:

a single covalent bond, a divalent radical chosen from:

an oxygen atom, a radical —NR$_6$(R$_7$)$_p$—, where p is 0 or 1; wherein when p is equal to 0, $R_6$ is chosen from a hydrogen atom and $C_1$-$C_6$ alkyl radicals, or $R_6$ together with at least one of $R_1$ and $R_2$ form, together with the nitrogen atom to which they are attached, a substituted or unsubstituted, saturated or unsaturated, aromatic or non-aromatic heterocycle comprising 5 to 8 ring members, wherein said heterocyle may optionally comprise at least one heteroatom or group chosen from N, O, S, SO$_2$, —CO—, and may be cationic and/or substituted with a cationic or non-cationic radical;

when p is equal to 1, —NR$_6$R$_7$— is a cationic radical in which $R_6$ and $R_7$ may be the same or different, and are independently chosen from alkyl radicals; and when $R_1$ is a methyl radical, $Z_1$ can also be chosen from a divalent radical —S—, —SO— and —SO$_2$—;

with the proviso that at least one of $Z_1$ and $Z_2$ is not a single covalent bond;

$R_1$ and $R_2$, which may be the same or different, are independently chosen from:

a hydrogen atom a $C_1$-$C_{10}$ alkyl radical, optionally substituted and optionally interrupted by at least one heteroatom or group chosen from O, N, Si, S, SO, SO$_2$, a $C_1$-$C_{10}$ alkyl radical substituted and/or interrupted by a cationic radical, a halogen atom, an SO$_3$H radical, a ring with 5 to 8 ring members, wherein said ring may be substituted or unsubstituted, saturated, unsaturated or aromatic, and can contain at least one heteroatom or group chosen from N, O, S, SO$_2$, —CO—, and said ring can be cationic and/or substituted with a cationic radical; and when $Z_1$ or $Z_2$ is a covalent bond, $R_1$ or $R_2$ respectively may also be a radical chosen from:

optionally substituted $C_1$-$C_6$ alkylcarbonyls; and

—O—CO—R, —CO—O—R, NR—CO—R' or —CO—NRR' in which R and R' may be the same or different, and are independently chosen from a hydrogen atom and optionally substituted $C_1$-$C_6$ alkyl radicals;

$R_3$, $R_4$ and $R_5$, which may be the same or different, are independently chosen from:

a hydrogen atom;

a hydroxyl radical;

a $C_1$-$C_6$ alkoxy radical;

a $C_1$-$C_6$ alkylthio radical;

an amino radical;

a monoalkylamino radical;

a $C_1$-$C_6$ dialkylamino radical, in which the alkyl radicals can form, together with the nitrogen atom to which they are attached, a heterocycle comprising 5 to 8 ring members, wherein said heterocycle may be saturated or unsaturated, aromatic or non-aromatic, and can contain at least one heteroatom or group chosen from N, O, S, SO$_2$, CO, and said heterocycle may be cationic, and/or substituted with a cationic radical;

an optionally substituted $C_1$-$C_6$ alkylcarbonyl radical;

a radical —O—CO—R, —CO—O—R, NR—CO—R' or —CO—NRR', in which R and R' may be the same or different, and are independently chosen from a hydrogen atom and optionally substituted $C_1$-$C_6$ alkyl radicals;

a halogen atom;

a radical —NHSO$_3$H, an optionally substituted $C_1$-$C_4$ alkyl radical;

an optionally substituted, saturated, unsaturated or aromatic carbon ring; and any two of $R_3$, $R_4$ and $R_5$ may form a saturated or unsaturated ring;

X is chosen from at least one anion that can ensure the electronegativity of the derivative of formula (I), with the proviso that at least one of the groups $Z_1$, $R_1$, $Z_2$, $R_2$ is a cationic radical; and at least one second compartment contains at least one oxidizing agent.

17. A dye compound of formula (I):

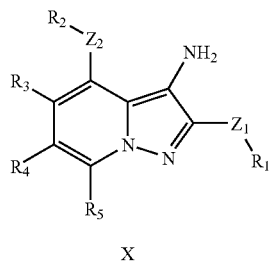

(I)

in which

Z₁ and Z₂, which may be the same or different, are independently chosen from:
a single covalent bond,
a divalent radical chosen from:
an oxygen atom,
a radical —NR₆(R₇)ₚ—, where p is 0 or 1; wherein
when p is equal to 0, R₆ is chosen from a hydrogen atom and C₁-C₆ alkyl radicals, or R₆ together with at least one of R₁ and R₂ form, together with the nitrogen atom to which they are attached, a substituted or unsubstituted, saturated or unsaturated, aromatic or non-aromatic heterocycle comprising 5 to 8 ring members, wherein said heterocyle can optionally comprise at least one heteroatom or group chosen from N, O, S, SO₂, —CO—, and may be cationic and/or substituted with a cationic or non-cationic radical;
when p is equal to 1, —NR₆R₇— is a cationic radical in which R₆ and R₇ may be the same or different, and are independently chosen from alkyl radicals; and
when R₁ is a methyl radical, Z₁ can also be chosen from a divalent radical —S—, —SO— and —SO₂—;
with the proviso that at least one of Z₁ and Z₂ is not a single covalent bond;
R₁ and R₂, which may be the same or different, are independently chosen from:
a hydrogen atom
a C₁-C₁₀ alkyl radical, optionally substituted and optionally interrupted by at least one heteroatom or group chosen from O, N, Si, S, SO, SO₂,
a C₁-C₁₀ alkyl radical substituted and/or interrupted by a cationic radical,
a halogen atom,
an SO₃H radical,
a ring with 5 to 8 ring members, wherein said ring may be substituted or unsubstituted, saturated, unsaturated or aromatic, and may contain at least one heteroatom or group chosen from N, O, S, SO₂, —CO—, and said ring can be cationic and/or substituted with a cationic radical; and
when Z₁ or Z₂ is a covalent bond, R₁ or R₂ respectively may also be a radical chosen from:
optionally substituted C₁-C₆ alkylcarbonyls; and
—O—CO—R, —CO—O—R, NR—CO—R' or —CO—NRR' in which R and R' may be the same or different, and are independently chosen from a hydrogen atom and optionally substituted C₁-C₆ alkyl radicals;

R₃, R₄ and R₅, which may be the same or different, are independently chosen from:
a hydrogen atom;
a hydroxyl radical;
a C₁-C₆ alkoxy radical;
a C₁-C₆ alkylthio radical;
an amino radical;
a monoalkylamino radical;
a C₁-C₆ dialkylamino radical, in which the alkyl radicals can form, together with the nitrogen atom to which they are attached, a heterocycle comprising 5 to 8 ring members, wherein said heterocycle may be saturated or unsaturated, aromatic or non-aromatic, and may contain at least one heteroatom or group chosen from N, O, S, SO₂, CO, and said heterocycle may be cationic, and/or substituted with a cationic radical;
an optionally substituted C₁-C₆ alkylcarbonyl radical;
a radical —O—CO—R, —CO—O—R, NR—CO—R' or —CO—NRR', in which R and R' may be the same or different, and are independently chosen from a hydrogen atom and optionally substituted C₁-C₆ alkyl radicals;
a halogen atom;
a radical —NHSO₃H,
an optionally substituted C₁-C₄ alkyl radical;
an optionally substituted, saturated, unsaturated or aromatic carbon ring; and
any two of R₃, R₄ and R₅, may form a saturated or unsaturated ring;
X is chosen from at least one anion that can ensure the electronegativity of the derivative of formula (I),
with the proviso that at least one of the groups Z₁, R₁, Z₂, R₂ is a cationic radical.

18. A method for the preparation of a dye compound of formula (I):

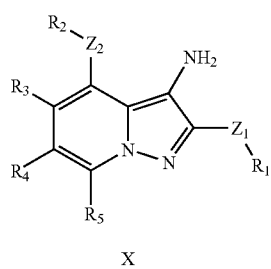

(I)

in which

Z₁ and Z₂, which may be the same or different, are independently chosen from:
a single covalent bond,
a divalent radical chosen from:
an oxygen atom,
a radical —NR₆(R₇)ₚ—, where p is 0 or 1; wherein
when p is equal to 0, R₆ is chosen from a hydrogen atom and C₁-C₆ alkyl radicals, or R₆ together with at least one of R₁ and R₂ form, together with the nitrogen atom to which they are attached, a substituted or unsubstituted, saturated or unsaturated, aromatic or non-aromatic heterocycle comprising 5 to 8 ring members, wherein said heterocyle can optionally comprise at least one heteroatom or group chosen from N, O, S, SO₂, —CO—, and may be cationic and/or substituted with a cationic or non-cationic radical;

when p is equal to 1, —NR$_6$R$_7$— is a cationic radical in which R$_6$ and R$_7$ may be the same or different, and are independently chosen from alkyl radicals; and when R$_1$ is a methyl radical, Z$_1$ may also be chosen from a divalent radical —S—, —SO— and —SO$_2$—;

with the proviso that at least one of Z$_1$ and Z$_2$ is not a single covalent bond;

R$_1$ and R$_2$, which may be the same or different, are independently chosen from:
a hydrogen atom
a C$_1$-C$_{10}$ alkyl radical, optionally substituted and optionally interrupted by at least one heteroatom or group chosen from O, N, Si, S, SO, SO$_2$,
a C$_1$-C$_{10}$ alkyl radical substituted and/or interrupted by a cationic radical,
a halogen atom,
an SO$_3$H radical,
a ring with 5 to 8 ring members, wherein said ring may be substituted or unsubstituted, saturated, unsaturated or aromatic, and may contain at least one heteroatom or group chosen from N, O, S, SO$_2$, —CO—, and said ring can be cationic and/or substituted with a cationic radical; and when Z$_1$ or Z$_2$ is a covalent bond, R$_1$ or R$_2$ respectively can also be a radical chosen from:
optionally substituted C$_1$-C$_6$ alkylcarbonyls; and
—O—CO—R, —CO—O—R, NR—CO—R' or —CO—NRR' in which R and R' may be the same or different, and are independently chosen from a hydrogen atom and optionally substituted C$_1$-C$_6$ alkyl radicals;

R$_3$, R$_4$ and R$_5$, which may be the same or different, are independently chosen from:

a hydrogen atom;
a hydroxyl radical;
a C$_1$-C$_6$ alkoxy radical;
a C$_1$-C$_6$ alkylthio radical;
an amino radical;
a monoalkylamino radical;
a C$_1$-C$_6$ dialkylamino radical, in which the alkyl radicals can form, together with the nitrogen atom to which they are attached, a heterocycle comprising 5 to 8 ring members, wherein said heterocycle may be saturated or unsaturated, aromatic or non-aromatic, and can contain at least one heteroatom or group chosen from N, O, S, SO$_2$, CO, and said heterocycle may be cationic, and/or substituted with a cationic radical;
an optionally substituted C$_1$-C$_6$ alkylcarbonyl radical;
a radical —O—CO—R, —CO—O—R, NR—CO—R' or —CO—NRR', in which R and R' may be the same or different, and are independently chosen from a hydrogen atom and optionally substituted C$_1$-C$_6$ alkyl radicals;
a halogen atom;
a radical —NHSO$_3$H,
an optionally substituted C$_1$-C$_4$ alkyl radical;
an optionally substituted, saturated, unsaturated or aromatic carbon ring; and
any two of R$_3$, R$_4$ and R$_5$, may form a saturated or unsaturated ring;

X is chosen from at least one anion that can ensure the electronegativity of the derivative of formula (I),
with the proviso that at least one of the groups Z$_1$, R$_1$, Z$_2$, R$_2$ is a cationic radical;
wherein said method comprises the following:

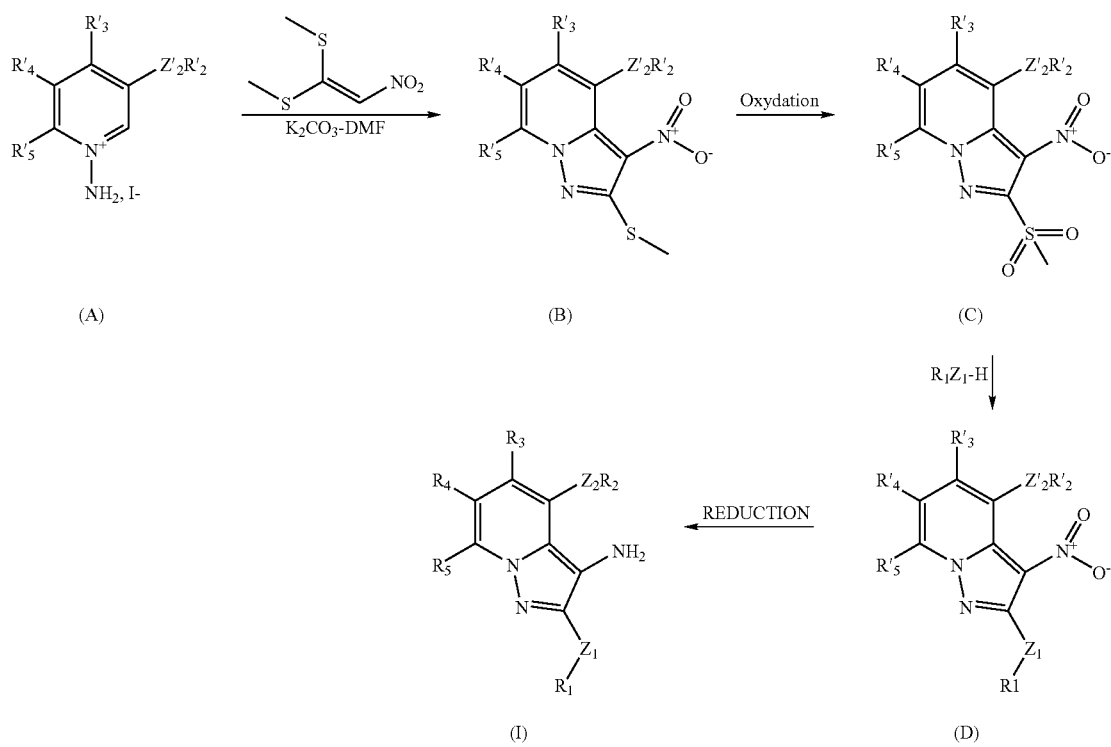

in which $Z'_2$, $R'_2$, $R'_3$, $R'_4$ and $R'_5$ have the same meanings as $Z_2$, $R_2$, $R_3$, $R_4$ and $R_5$, defined above, or are precursors thereof.

19. A dye intermediate compound of formula (A), salts thereof, solvates thereof, and derivatives thereof:

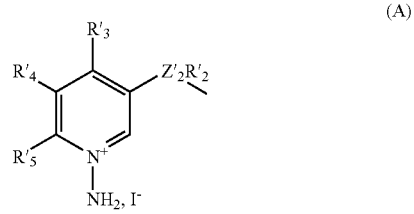

in which,
$Z'_2$ is chosen from:
  a single covalent bond,
  a divalent radical chosen from:
    an oxygen atom,
    a radical $-NR_6(R_7)_p-$, where p is 0 or 1; wherein
      when p is equal to 0, $R_6$ is chosen from a hydrogen atom and $C_1$-$C_6$ alkyl radicals, or $R_6$ together with $R'_2$ form, together with the nitrogen atom to which they are attached, a substituted or unsubstituted, saturated or unsaturated, aromatic or non-aromatic heterocycle comprising 5 to 8 ring members, wherein said heterocyle can optionally comprise at least one heteroatom or group chosen from N, O, S, $SO_2$, $-CO-$, and may be cationic and/or substituted with a cationic or non-cationic radical;
      when p is equal to 1, $-NR_6R_7-$ is a cationic radical in which $R_6$ and $R_7$ may be the same or different, and are independently chosen from alkyl radicals; and $R'_2$ is chosen from:
  a hydrogen atom
  a $C_1$-$C_{10}$ alkyl radical, optionally substituted and optionally interrupted by at least one heteroatom or group chosen from O, N, Si, S, SO, $SO_2$,
  a $C_1$-$C_{10}$ alkyl radical substituted and/or interrupted by a cationic radical,
  a halogen atom,
  an $SO_3H$ radical,
  a ring with 5 to 8 ring members, wherein said ring may be substituted or unsubstituted, saturated, unsaturated or aromatic, and can contain at least one heteroatom or group chosen from N, O, S, $SO_2$, $-CO-$, and said ring can be cationic and/or substituted with a cationic radical; and when $Z'_2$ is a covalent bond, $R'_2$ respectively can also be a radical chosen from:
  optionally substituted $C_1$-$C_6$ alkylcarbonyl; and
  $-O-CO-R$, $-CO-O-R$, $NR-CO-R'$ or $-CO-NRR'$ in which R and R' may be the same or different, and are independently chosen from a hydrogen atom and optionally substituted $C_1$-$C_6$ alkyl radicals;

$R'_3$, $R'_4$ and $R'_5$ which may be the same or different, are independently chosen from:
  a hydrogen atom;
  a hydroxyl radical;
  a $C_1$-$C_6$ alkoxy radical;
  a $C_1$-$C_6$ alkylthio radical;
  an amino radical;
  a monoalkylamino radical;
  a $C_1$-$C_6$ dialkylamino radical, in which the alkyl radicals can form, together with the nitrogen atom to which they are attached, a heterocycle comprising 5 to 8 ring members, wherein said heterocycle may be saturated or unsaturated, aromatic or non-aromatic, and may contain at least one heteroatom or group chosen from N, O, S, $SO_2$, CO, and said heterocycle may be cationic, and/or substituted with a cationic radical;
  an optionally substituted $C_1$-$C_6$ alkylcarbonyl radical;
  a radical $-O-CO-R$, $-CO-O-R$, $NR-CO-R'$ or $-CO-NRR'$, in which R and R' may be the same or different, and are independently chosen from a hydrogen atom and optionally substituted $C_1$-$C_6$ alkyl radicals;
  a halogen atom;
  a radical $-NHSO_3H$,
  an optionally substituted $C_1$-$C_4$ alkyl radical;
  an optionally substituted, saturated, unsaturated or aromatic carbon ring; and
  any two of $R'_3$, $R'_4$ and $R'_5$ may form a saturated or unsaturated ring;
  and wherein $Z'_2$ and $R'_2$ can be a cationic radical;
  with the exception of the compounds 1-amino-3-methylpyridinium iodide and 4-methyl-2-(methylsulphanyl)-3-nitropyrazolo[1,5-a]pyridine.

20. A dye intermediate compound of formula (B), salts thereof, solvates thereof, and derivatives thereof:

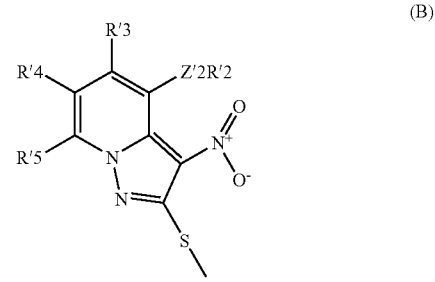

in which,
$Z'_2$ is chosen from:
  a single covalent bond,
  a divalent radical chosen from:
    an oxygen atom,
    a radical $-NR_6(R_7)_p-$, where p is 0 or 1; wherein
      when p is equal to 0, $R_6$ is chosen from a hydrogen atom and $C_1$-$C_6$ alkyl radicals, or $R_6$ together with $R'_2$ form, together with the nitrogen atom to which they are attached, a substituted or unsubstituted, saturated or unsaturated, aromatic or non-aromatic heterocycle comprising 5 to 8 ring members, wherein said heterocyle may optionally comprise at least one heteroatom or group chosen from N, O, S, $SO_2$, $-CO-$, and may be cationic and/or substituted with a cationic or non-cationic radical;
      when p is equal to 1, $-NR_6R_7-$ is a cationic radical in which $R_6$ and $R_7$ may be the same or different, and are independently chosen from alkyl radicals; and $R'_2$ is chosen from:
- a hydrogen atom
- a $C_1$-$C_{10}$ alkyl radical, optionally substituted and optionally interrupted by at least one heteroatom or group chosen from O, N, Si, S, SO, $SO_2$,
- a $C_1$-$C_{10}$ alkyl radical substituted and/or interrupted by a cationic radical,
- a halogen atom,
- an $SO_3H$ radical,
- a ring with 5 to 8 ring members, wherein said ring may be substituted or unsubstituted, saturated, unsaturated or aromatic, and may contain at least one heteroatom or group chosen from N, O, S, $SO_2$, —CO—, and said ring can be cationic and/or substituted with a cationic radical; and when $Z'_2$ is a covalent bond, $R'_2$ can also be a radical chosen from:
- optionally substituted $C_1$-$C_6$ alkylcarbonyl; and
- —O—CO—R, —CO—O—R, NR—CO—R' or —CO—NRR' in which R and R' may be the same or different, and are independently chosen from a hydrogen atom and optionally substituted $C_1$-$C_6$ alkyl radicals;

$R'_3$, $R'_4$ and $R'_5$ which may be the same or different, are independently chosen from:
- a hydrogen atom;
- a hydroxyl radical;
- a $C_1$-$C_6$ alkoxy radical;
- a $C_1$-$C_6$ alkylthio radical;
- an amino radical;
- a monoalkylamino radical;
- a $C_1$-$C_6$ dialkylamino radical, in which the alkyl radicals can form, together with the nitrogen atom to which they are attached, a heterocycle comprising 5 to 8 ring members, wherein said heterocycle may be saturated or unsaturated, aromatic or non-aromatic, and can contain at least one heteroatom or group chosen from N, O, S, $SO_2$, CO, and said heterocycle may be cationic, and/or substituted with a cationic radical;
- an optionally substituted $C_1$-$C_6$ alkylcarbonyl radical;
- a radical —O—CO—R, —CO—O—R, NR—CO—R' or —CO—NRR', in which R and R' may be the same or different, and are independently chosen from a hydrogen atom and optionally substituted $C_1$-$C_6$ alkyl radicals;
- a halogen atom;
- a radical —$NHSO_3H$,
- an optionally substituted $C_1$-$C_4$ alkyl radical;
- an optionally substituted, saturated, unsaturated or aromatic carbon ring; and
- any two of $R'_3$, $R'_4$ and $R'_5$ can form a saturated or unsaturated ring;
  and wherein $Z'_2$ and $R'_2$ can be a cationic radical,
  with the exception of the compounnds 1-amino-3-methylpyridinium iodide and 4-methyl-2-(methylsulphanyl)-3-nitropyrazolo[1,5-a]pyridine.

21. A dye intermediate compound of formula C, salts thereof, solvates thereof, and derivatives thereof:

(C)

in which,
$Z'_2$ is chosen from:
- a single covalent bond,
- a divalent radical chosen from:
  - an oxygen atom,
  - a radical —$NR_6(R_7)_p$—, where p is 0 or 1; wherein
    when p is equal to 0, $R_6$ is chosen from a hydrogen atom and $C_1$-$C_6$ alkyl radicals, or $R_6$ together with $R'_2$ form, together with the nitrogen atom to which they are attached, a substituted or unsubstituted, saturated or unsaturated, aromatic or non-aromatic heterocycle comprising 5 to 8 ring members, wherein said heterocyle may optionally comprise at least one heteroatom or group chosen from N, O, S, $SO_2$, —CO—, and may be cationic and/or substituted with a cationic or non-cationic radical;
    when p is equal to 1, —$NR_6R_7$— is a cationic radical in which $R_6$ and $R_7$ may be the same or different, and are independently chosen from alkyl radicals; and $R'_2$ is chosen from:
- a hydrogen atom
- a $C_1$-$C_{10}$ alkyl radical, optionally substituted and optionally interrupted by at least one heteroatom or group chosen from O, N, Si, S, SO, $SO_2$,
- a $C_1$-$C_{10}$ alkyl radical substituted and/or interrupted by a cationic radical,
- a halogen atom,
- an $SO_3H$ radical,
- a ring with 5 to 8 ring members, wherein said ring may be substituted or unsubstituted, saturated, unsaturated or aromatic, and may contain at least one heteroatom or group chosen from N, O, S, $SO_2$, —CO—, and said ring can be cationic and/or substituted with a cationic radical; and when at least one of $Z'_2$ is a covalent bond, $R'_2$ can also be a radical chosen from:
- optionally substituted $C_1$-$C_6$ alkylcarbonyls; and
- —O—CO—R, —CO—O—R, NR—CO—R' or —CO—NRR' in which R and R' may be the same or different, and are independently chosen from a hydrogen atom and optionally substituted $C_1$-$C_6$ alkyl radicals;

$R'_3$, $R'_4$ and $R'_5$, which may be the same or different, are independently chosen from:
- a hydrogen atom;
- a hydroxyl radical;
- a $C_1$-$C_6$ alkoxy radical;
- a $C_1$-$C_6$ alkylthio radical;
- an amino radical;
- a monoalkylamino radical;

a $C_1$-$C_6$ dialkylamino radical, in which the alkyl radicals can form, together with the nitrogen atom to which they are attached, a heterocycle comprising 5 to 8 ring members, wherein said heterocycle may be saturated or unsaturated, aromatic or non-aromatic, and can contain at least one heteroatom or group chosen from N, O, S, $SO_2$, CO, and said heterocycle may be cationic, and/or substituted with a cationic radical;

an optionally substituted $C_1$-$C_6$ alkylcarbonyl radical;

a radical —O—CO—R, —CO—O—R, NR—CO—R' or —CO—NRR', in which R and R' may be the same or different, and are independently chosen from a hydrogen atom and optionally substituted $C_1$-$C_6$ alkyl radicals;

a halogen atom;

a radical —$NHSO_3H$, an optionally substituted $C_1$-$C_4$ alkyl radical;

an optionally substituted, saturated, unsaturated or aromatic carbon ring; and any two of $R'_3$, $R'_4$ and $R'_5$ can form a saturated or unsaturated ring;

and wherein $Z'_2$ and $R'_2$ can be a cationic radical,

22. A dye intermediate compound of formula (D), salts thereof, solvates thereof, and derivatives thereof:

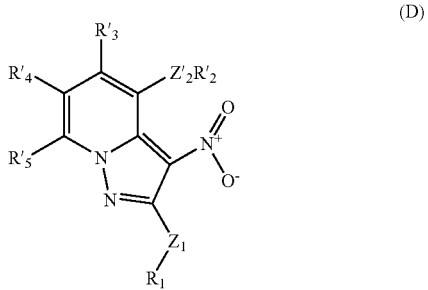

in which, $Z'_2$ is chosen from:
  a single covalent bond,
  a divalent radical chosen from:
    an oxygen atom,
    a radical —$NR_6(R_7)_p$- , where p is 0 or 1; wherein
      when p is equal to 0, $R_6$ is chosen from a hydrogen atom and $C_1$-$C_6$ alkyl radicals, or $R_6$ together with $R'_2$ form, together with the nitrogen atom to which they are attached, a substituted or unsubstituted, saturated or unsaturated, aromatic or non-aromatic heterocycle comprising 5 to 8 ring members, wherein said heterocyle may optionally comprise at least one heteroatom or group chosen from N, O, S, $SO_2$, —CO—, and may be cationic and/or substituted with a cationic or non-cationic radical;
      when p is equal to 1, —$NR_6R_7$— is a cationic radical in which $R_6$ and $R_7$ may be the same or different, and are independently chosen from alkyl radicals; and
  with the proviso that at least one of $Z_1$ and $Z'_2$ is not a single covalent bond;

$R'_2$ is chosen from:
  a hydrogen atom
  a $C_1$-$C_{10}$ alkyl radical, optionally substituted and optionally interrupted by at least one heteroatom or group chosen from O, N, Si, S, SO, $SO_2$,
  a $C_1$-$C_{10}$ alkyl radical substituted and/or interrupted by a cationic radical,
  a halogen atom,
  an $SO_3H$ radical,
  a ring with 5 to 8 ring members, wherein said ring may be substituted or unsubstituted, saturated, unsaturated or aromatic, and can contain at least one heteroatom or group chosen from N, O, S, $SO_2$, —CO—, and said ring can be cationic and/or substituted with a cationic radical; and when at least one of $Z_1$ and $Z'_2$ is a covalent bond, $R_1$ or $R'_2$ respectively can also be a radical chosen from:
  optionally substituted $C_1$-$C_6$ alkylcarbonyl; and
  —O—CO—R, —CO—O—R, NR—CO—R' or —CO—NRR' in which R and R' may be the same or different, and are independently chosen from a hydrogen atom and optionally substituted $C_1$-$C_6$ alkyl radicals;

$R'_3$, $R'_4$ and $R'_5$, which may be the same or different, are independently chosen from:
  a hydrogen atom;
  a hydroxyl radical;
  a $C_1$-$C_6$ alkoxy radical;
  a $C_1$-$C_6$ alkylthio radical;
  an amino radical;
  a monoalkylamino radical;
  a $C_1$-$C_6$ dialkylamino radical, in which the alkyl radicals can form, together with the nitrogen atom to which they are attached, a heterocycle comprising 5 to 8 ring members, wherein said heterocycle may be saturated or unsaturated, aromatic or non-aromatic, and can contain at least one heteroatom or group chosen from N, O, S, $SO_2$, CO, and said heterocycle may be cationic, and/or substituted with a cationic radical;
  an optionally substituted $C_1$-$C_6$ alkylcarbonyl radical;
  a radical —O—CO—R, —CO—O—R, NR—CO—R' or —CO—NRR', in which R and R' may be the same or different, and are independently chosen from a hydrogen atom and optionally substituted $C_1$-$C_6$ alkyl radicals;
  a halogen atom;
  a radical —$NHSO_3H$,
  an optionally substituted $C_1$-$C_4$ alkyl radical;
  an optionally substituted, saturated, unsaturated or aromatic carbon ring; and
  any two of $R'_3$, $R'_4$ and $R'_5$ can form a saturated or unsaturated ring;
  and wherein $Z'_2$ and $R'_2$ can be a cationic radical.

* * * * *